United States Patent
Gauvry et al.

(10) Patent No.: US 7,642,379 B2
(45) Date of Patent: Jan. 5, 2010

(54) AMINOACETONITRILE DERIVATIVES AND THEIR USE FOR CONTROLLING PARASITES ON WARM-BLOODED ANIMALS

(75) Inventors: Noëlle Gauvry, Kembs-Loechle (FR); Pierre Ducray, Village-Neuf (FR); Thomas Goebel, Lörrach (DE); Ronald Kaminsky, Lugnorre (CH)

(73) Assignee: Novartis AG, Basel (CH)

( * ) Notice: Subject to any disclaimer, the term of this patent is extended or adjusted under 35 U.S.C. 154(b) by 236 days.

(21) Appl. No.: 11/596,961

(22) PCT Filed: Jun. 9, 2005

(86) PCT No.: PCT/EP2005/006207

§ 371 (c)(1),
(2), (4) Date: Nov. 17, 2006

(87) PCT Pub. No.: WO2005/121075

PCT Pub. Date: Dec. 22, 2005

(65) Prior Publication Data

US 2008/0194693 A1    Aug. 14, 2008

(30) Foreign Application Priority Data

Jun. 10, 2004    (EP) ................... 04013690

(51) Int. Cl.
*C07C 237/32* (2006.01)
*A61K 31/166* (2006.01)
(52) U.S. Cl. ...................... 564/185; 514/617
(58) Field of Classification Search ................. 564/185
See application file for complete search history.

(56) References Cited

FOREIGN PATENT DOCUMENTS

| | | | |
|---|---|---|---|
| EP | 0 227 274 A | 7/1987 | |
| EP | 0 953 565 A | 3/1999 | |
| EP | 0953565 A2 * | 11/1999 | ................. 564/185 |
| GB | 1 148 332 A | 4/1969 | |
| WO | WO 02/49641 A | 6/2002 | |
| WO | WO 02/060257 A | 8/2002 | |
| WO | WO 03/080577 A | 10/2003 | |
| WO | WO 03/097585 A | 11/2003 | |
| WO | WO04/000793 | 12/2003 | |

* cited by examiner

*Primary Examiner*—Rebecca L Anderson
*Assistant Examiner*—Shawquia Young
(74) *Attorney, Agent, or Firm*—Womble Carlyle Sandridge & Rice, PLLC; Amy H. Fix

(57) ABSTRACT

The invention relates to compounds of the general formula (I) wherein Ar, $R_1$, $R_2$, $R_3$, $R_4$, $R_5$, $R_6$, $R_7$, $R_8$, $R_9$, $R_{10}$, W, a, b, m, n, o and p are as defined in claim 1, and to any enantiomers thereof. The active ingredients have advantageous pesticidal properties. They are particularly suitable for controlling parasites in warm-blooded animals.

7 Claims, No Drawings

AMINOACETONITRILE DERIVATIVES AND THEIR USE FOR CONTROLLING PARASITES ON WARM-BLOODED ANIMALS

This application is a National Phase Application under § 371 of International Application Number PCT/EP 2005/1006207 filed on Jun. 9, 2005, herein incorporated by reference in its entirety The present invention relates to new amidoacetonitrile compounds of the formula

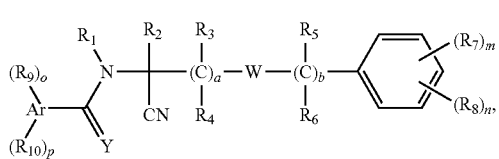

wherein

Ar is unsubstituted or one- or poly-substituted aryl or hetaryl;

$R_1$ is hydrogen, $C_1$-$C_6$alkyl, halo-$C_1$-$C_6$alkyl, $C_1$-$C_6$-alkylcarbonyl, $C_1$-$C_6$alkoxycarbonyl, allyl, $C_1$-$C_6$alkoxymethyl, unsubstituted or one- or poly-substituted phenylcarbonyl, $C_1$-$C_6$alkylsulfonyl or unsubstituted or one- or poly-substituted phenylsulfonyl;

$R_2$, $R_3$, $R_1$, $R_5$ and $R_6$ are either, independently of one another, hydrogen, halogen, unsubstituted or one- or poly-substituted $C_1$-$C_6$alkyl, unsubstituted or one- or poly-substituted $C_2$-$C_6$alkenyl, unsubstituted or one- or poly-substituted $C_2$-$C_6$alkinyl, unsubstituted or one- or poly-substituted $C_1$-$C_6$alkoxy, whereby the substituents in each case can be independent of one another and are chosen from the group consisting of halogen, $C_1$-$C_6$alkoxy and halo-$C_1$-$C_6$alkoxy; unsubstituted or one- or poly-substituted $C_3$-$C_6$cycloalkyl, whereby the substituents in each case can be independent of one another and are chosen from the group consisting of halogen and $C_1$-$C_6$alkyl; or unsubstituted or one- or poly-substituted phenyl, whereby the substituents in each case can be independent of one another and are chosen from the group consisting of halogen, nitro, cyano, $C_1$-$C_6$alkyl, halo-$C_1$-$C_6$alkyl, $C_1$-$C_6$alkoxy, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_1$-$C_6$alkylamino and di-$C_1$-$C_6$alkylamino;

or $R_2$ and $R_3$ are together $C_2$-$C_6$alkylene;

$R_7$ and $R_{10}$ are, independently of each other, $NH_2$, OH, SH, carboxy, aminocarbonyl, aminothiocarbonyl, aminothiocarbonyloxy, ureyl, thioureyl, unsubstituted or one- or poly-substituted phenylthiocarbamido, unsubstituted or one- or poly-substituted $C_1$-$C_6$alkylthiocarbamido, unsubstituted or one- or poly-substituted $C_1$-$C_6$alkoxythiocarbamido, unsubstituted or one- or poly-substituted phenyloxythiocarbamido, unsubstituted or one- or poly-substituted phenylaminothiocarboxy, unsubstituted or one- or poly-substituted phenyloxythiocarboxy, unsubstituted or one- or poly-substituted phenylaminothiocarboxamido, unsubstituted or one- or poly-substituted $C_1$-$C_6$alkylaminothiocarbonyl, ($C_1$-$C_6$-alkyl)$_2$aminothiocarbonyl, phenylaminothiocarbonyl, unsubstituted or one- or poly-substituted phenylsulfanylcarbonyl, unsubstituted or one- or poly-substituted benzylsulfanylcarbonyl, unsubstituted or one- or poly-substituted phenylsulfanyl-$C_1$-$C_6$alkyl, unsubstituted or one- or poly-substituted phenyl-$C_1$-$C_6$alkylsulfanyl, $C_1$-$C_6$alkylsulfanylcarbonyl, $C_1$-$C_6$alkylcarbonylsulfanyl, unsubstituted or one- or poly-substituted phenylcarbonylsulfanyl, halo-$C_2$-$C_6$alkynyl, $C_1$-$C_6$alkylaminothiocarboxy, $C_1$-$C_6$alkyloxythiocarboxy, $C_1$-$C_6$alkylaminothiocarboxamido, (1,3)-oxathiolyl, 2-halo-(1,3)-oxathiolyl, (1,3)-dioxolyl, 2-halo-(1,3)-dioxolyl, sulfonyl, aminosulfonyl, $C_1$-$C_6$alkylaminosulfonyl, di-$C_1$-$C_6$alkylaminosulfonyl, unsubstituted or one- or poly-substituted arylaminosulfonyl, unsubstituted or one- or poly-substituted arylsulfonyloxy, unsubstituted or one- or poly-substituted arylsulfonylamino, unsubstituted or one- or poly-substituted aryloxysulfonyl, $C_1$-$C_6$alkyloxysulfonyl, $C_1$-$C_6$alkylaminocarbonylsulfanyl, unsubstituted or one- or poly-substituted phenylaminocarbonylsulfanyl, unsubstituted or one- or poly-substituted phenoxythiocarbonyl, unsubstituted or one- or poly-substituted phenylsulfanylthiocarbonyl, or $C_1$-$C_6$alkyloxythiocarbonyl, whereby the substituents in each case can be independent of one another and are chosen from the group consisting of $R_1$ and halogen;

$R_8$ is halogen, nitro, cyano, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, halo-$C_2$-$C_6$alkenyl, $C_2$-$C_6$alkynyl, $C_3$-$C_6$cycloalkyl, $C_3$-$C_6$cycloalkoxy, $C_3$-$C_6$cycloalkylamino, $C_3$-$C_6$cycloalkylthio, $C_2$-$C_6$alkenyloxy, halo-$C_2$-$C_6$alkenyloxy, $C_1$-$C_6$alkylthio, halo-$C_1$-$C_6$alkylthio, $C_1$-$C_6$alkylsulfonyloxy, halo-$C_1$-$C_6$alkylsulfonyloxy, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_2$-$C_6$alkenylthio, halo-$C_2$-$C_6$alkenylthio, $C_2$-$C_6$alkenylsulfinyl, halo-$C_2$-$C_6$alkenylsulfinyl, $C_2$-$C_6$alkenylsulfonyl, halo-$C_2$-$C_6$alkenylsulfonyl, $C_1$-$C_6$alkylamino, di-$C_1$-$C_6$alkylamino, $C_1$-$C_6$alkylsulfonylamino, halo-$C_1$-$C_6$alkylsulfonylamino, $C_1$-$C_6$alkylcarbonyl, halo-$C_1$-$C_6$alkylcarbonyl, $C_1$-$C_6$alkoxycarbonyl, $C_1$-$C_6$alkylaminocarbonyl, di-$C_1$-$C_6$alkylaminocarbonyl, unsubstituted or one- or poly-substituted phenylamino, unsubstituted or one- or poly-substituted phenylcarbonyl, unsubstituted or one- or poly-substituted phenylmethoximino, unsubstituted or one- or poly-substituted phenylhydroxymethyl, unsubstituted or one- or poly-substituted 1-phenyl-1-hydroxyethyl, unsubstituted or one- or poly-substituted phenylchloromethyl, unsubstituted or one- or poly-substituted phenylcyanomethyl, unsubstituted or one- or poly-substituted phenyl, unsubstituted or one- or poly-substituted phenoxy, unsubstituted or one- or poly-substituted phenylacetylenyl, unsubstituted or one- or poly-substituted pyridyloxy, or unsubstituted or one- or poly-substituted phenylsulfanyl, whereby the substituents in each case can be independent of one another and are chosen from the group consisting of $R_1$ and halogen;

$R_9$ is halogen, nitro, cyano, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, halo-$C_2$-$C_6$alkenyl, $C_2$-$C_6$alkynyl, $C_3$-$C_6$cycloalkyl, $C_3$-$C_6$cycloalkoxy, $C_3$-$C_6$cycloalkylamino, $C_3$-$C_6$cycloalkylthio, $C_2$-$C_6$alkenyloxy, halo-$C_2$-$C_6$alkenyloxy, $C_1$-$C_6$alkylthio, halo-$C_1$-$C_6$alkylthio, $C_1$-$C_6$alkylsulfonyloxy, halo-$C_1$-$C_6$alkylsulfonyloxy, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_2$-$C_6$alkenylthio, halo-$C_2$-$C_6$alkenylthio, $C_2$-$C_6$alkenylsulfinyl, halo-$C_2$-$C_6$alkenylsulfinyl, $C_2$-$C_6$alkenylsulfonyl, halo-$C_2$-$C_6$alkenylsulfonyl, $C_1$-$C_6$alkylamino, di-$C_1$-$C_6$alkylamino, $C_1$-$C_6$alkylsulfonylamino, halo-$C_1$-$C_6$alkylsulfonylamino, $C_1$-$C_6$alkylcarbonyl, halo-$C_1$-$C_6$alkylcarbonyl, $C_1$-$C_6$alkoxycarbonyl, $C_1$-$C_6$alkylaminocarbonyl, di-$C_1$-$C_6$alkylaminocarbonyl, unsubstituted or one- or poly-substituted phenylamino, unsubstituted or one- or poly-substituted arylsulfonyl, unsubstituted or one- or poly-substituted phenylcarbonyl, unsubstituted or one- or poly-substituted phenylmethoximino, unsubstituted or one- or poly-substituted phenylhydroxymethyl, unsubstituted or one- or poly-substituted 1-p-phenyl-1-hydroxyethyl, unsubstituted or one- or poly-substituted phenylchlormethyl, unsubstituted or one- or poly-substituted phenylcyanomethyl, unsubstituted or one- or poly-substituted phenyl, unsubstituted or one- or poly-substituted phenoxy, unsubstituted or one- or poly-substituted phenylacetylenyl, unsubstituted or one- or poly-substituted phenoxy, or pyridyloxy, whereby the substituents in each case can be independent of one another and are chosen from the group consisting of $R_1$ and halogen;

a is 1, 2, 3 or 4;

b is 0, 1, 2, 3 or 4;

m, n, o and p are, independent of each other, 0, 1, 2, 3, 4 or 5;

W is O, S, S($O_2$), N($R_1$), $C_1$-$C_6$alkyl or halo-$C_1$-$C_6$alkyl;

Y is O, S or N($R_{11}$); and $R_{11}$ is $C_1$-$C_6$alkyl or unsubstituted or one- or poly-substituted phenyl;

with the proviso that m and p are not equal to 0 at the same time; to their preparation and use in the control of endo- and ectoparasites, especially helminths, in and on warm-blooded productive livestock, domestic animals and plants, and also to pesticides which comprise at least one of these compounds.

Substituted amidoacetonitrile compounds with pesticidal action are disclosed in EP-0 953 565 A2, for example. The active ingredients specifically revealed therein may not, however, always meet the requirements concerning strength and activity spectrum. There consequently exists a need for active ingredients with improved pesticidal properties. It has now been found that the amidoacetonitrile compounds of the formula I have outstanding pesticidal properties, in particular against endo- and ectoparasites in and on productive livestock, domestic animals and plants.

Alkyl—as group per se and as structural component of other groups and compounds, for example of haloalkyl, alkoxy, alkylthio, alkylsulfinyl and alkylsulfonyl, —is, in each case giving due consideration to the number of carbon atoms which the relevant group or compound has in each individual case, either straight-chain, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl—as group per se and as structural component of other groups and compounds—is, in each case giving due consideration to the number of carbon atoms and conjugated or isolated double bonds which the relevant group or compound has in each individual case, either straight-chain, e.g. allyl, 2-butenyl, 3-pentenyl, 1-hexenyl or 1,3-hexadienyl, or branched, e.g. isopropenyl, isobutenyl, isoprenyl, tert-pentenyl or isohexenyl.

Alkynyl—as group per se and as structural component of other groups and compounds—is, in each case giving due consideration to the number of carbon atoms and conjugated or isolated double bonds which the relevant group or compound has in each individual case, either straight-chain, e.g. propargyl, 2-butynyl, 3-pentynyl, 1-hexynyl, 1-heptynyl or 3-hexen-1-ynyl, or branched, e.g. 3-methyl-but-1-ynyl, 4-ethylpent-1-ynyl or 4-methylhex-2-ynyl.

Cycloalkyl—as group per se and as structural component of other groups and compounds, for example of halocycloalkyl, cycloalkoxy or cycloalkylthio, —is, in each case giving due consideration to the number of carbon atoms which the relevant group or compound has in each individual case, cyclopropyl, cyclobutyl, cyclopentyl or cyclohexyl.

Aryl is phenyl or naphthyl, preferably phenyl.

Hetaryl is pyridyl, pyrimidyl, s-triazinyl, 1,2,4-triazinyl, thienyl, furanyl, pyrrolyl, pyrazolyl, imidazolyl, thiazolyl, triazolyl, oxazolyl, thiadiazolyl, oxadiazolyl, benzothienyl, benzofuranyl, benzothiazolyl, indolyl or indazolyl, preferably pyridyl, pyrimidyl, s-triazinyl or 1,2,4-triazinyl, in particular pyridyl or pyrimidyl.

Halogen—as group per se and as structural component of other groups and compounds, such as of haloalkyl, haloalkoxy, haloalkylthio, haloalkylsulfinyl and haloalkylsulfonyl, —is fluorine, chlorine, bromine or iodine, in particular fluorine, chlorine or bromine, especially fluorine or chlorine.

Halogen-substituted carbon-comprising groups and compounds, such as haloalkyl, halo-alkoxy, haloalkylthio, haloalkylsulfinyl and haloalkylsulfonyl, can be partially halogenated or perhalogenated, it being possible, in the case of polyhalogenation, for the halogen substituents to be identical or different. Examples of haloalkyl—as group per se and as structural component of other groups and compounds, such as of haloalkoxy or halo-alkylthio, —are methyl substituted up to three times by fluorine, chlorine and/or bromine, such as $CHF_2$ or $CF_3$; ethyl substituted up to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted up to seven times by fluorine, chlorine and/or bromine, such as $CH_2CHBrCH_2Br$, $CF_2CHFCF_3$, $CH_2CF_2CF_3$ or $CH(CF_3)_2$; butyl or one of its isomers substituted up to nine times by fluorine, chlorine and/or bromine, such as $CF(CF_3)CHFCF_3$ or $CH_2(CF_2)_2CF_3$; pentyl or one of its isomers substituted up to eleven times by fluorine, chlorine and/or bromine, such as $CF(CF_3)(CHF)_2CF_3$ or $CH_2(CF_2)_3CF_3$; and hexyl or one of its isomers substituted up to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. For example, alkoxy is methoxy, ethoxy, propoxy, isopropoxy, n-butoxy, isobutoxy, sec-butoxy and tert-butoxy, and also the pentyloxy and hexyloxy isomers; preferably methoxy and ethoxy. Haloalkoxy groups preferably have a chain length of 1 to 6 carbon atoms. Haloalkoxy is, e.g., fluoromethoxy, difluoromethoxy, trifluoromethoxy, 2,2,2-trifluoroethoxy, 1,1,2,2-tetrafluoroethoxy, 2-fluoro-ethoxy, 2-chloroethoxy, 2,2-difluoroethoxy and 2,2,2-trichloroethoxy; preferably difluoromethoxy, 2-chloroethoxy and trifluoromethoxy.

Preferred embodiments within the context of the invention are:

(1) A Compound of the Formula I, wherein

Ar is unsubstituted or one- or poly-substituted aryl;

preferably one- or di-substituted aryl;

(2) A Compound of the Formula I, wherein $R_1$ is hydrogen, $C_1$-$C_6$alkyl, halo-$C_1$-$C_6$alkyl, allyl or $C_1$-$C_6$alkoxymethyl;

preferably hydrogen, $C_1$-$C_4$alkyl or halo-$C_1$-$C_4$alkyl;

most preferably hydrogen or $C_1$-$C_2$alkyl;

(3) A Compound of the Formula I, wherein $R_2$, $R_3$, $R_4$, $R_5$ and $R_6$ are either, independently of one another, hydrogen, halogen, unsubstituted or one- or poly-substituted $C_1$-$C_4$alkyl, unsubstituted or one- or poly substituted $C_2$-$C_4$alkenyl, unsubstituted or one- or poly-substituted $C_2$-$C_4$alkinyl or unsubstituted or one- or poly-substituted $C_1$-$C_4$alkoxy, whereby the substituents in each case can be independent of one another and are chosen from the group consisting of halogen, $C_1$-$C_6$alkoxy and halo-$C_1$-$C_6$alkoxy; or $R_2$ and $R_3$ are together $C_2$-$C_4$alkylene;

preferably either, independently of one another, hydrogen, halogen or unsubstituted or one- or poly-substituted $C_1$-$C_4$alkyl, whereby the substituents in each case can be independent of one another and are chosen from the group consisting of halogen, $C_1$-$C_6$alkoxy and halo-$C_1$-$C_6$alkoxy; or $R_2$ and $R_5$ are together $C_2$-$C_4$alkylene;

most preferably, independently of one another, hydrogen or halogen;

(4) A compound of the formula I, wherein $R_7$ and $R_{10}$ are, independently of each other, $NH_2$, OH, SH, carboxy, aminocarbonyl, aminothiocarbonyl, aminothiocarbonyloxy, ureyl, thioureyl, $(C_1$-$C_6$-alkyl$)_2$aminothiocarbonyl, phenylaminothiocarbonyl, $C_1$-$C_6$alkylsulfanylcarbonyl, $C_1$-$C_6$alkylcarbonylsulfanyl, halo-$C_2$-$C_6$alkynyl, $C_1$-$C_6$alkylaminothiocarboxy, $C_1$-$C_6$alkyloxythiocarboxy, $C_1$-$C_6$alkylaminothiocarboxamido, (1,3)-oxathiolyl, 2-halo-(1,3)-oxathiolyl, (1,3)-dioxolyl, 2-halo-(1,3)-dioxolyl, sulfonyl, aminosulfonyl, $C_1$-$C_6$alkylaminosulfonyl, di-$C_1$-$C_6$alkylaminosulfonyl, $C_1$-$C_6$alkyloxysulfonyl, $C_1$-$C_6$alkylaminocarbonylsulfanyl, or $C_1$-$C_6$alkyloxythiocarbonyl;

preferably, independently of each other, carboxy, aminocarbonyl, (1,3)-dioxolyl or 2-halo-(1,3)-dioxolyl;

preferably, independently of each other, carboxy, aminocarbonyl, (1,3)-dioxolyl or 2-halo-(1,3)-dioxolyl;

most preferably, independently of each other, carboxy or aminocarbonyl;

(5) A compound of the formula I, wherein $R_8$ is halogen, nitro, cyano, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, halo-$C_2$-$C_6$alkenyl, $C_2$-$C_6$alkynyl, $C_3$-$C_6$cycloalkyl, $C_3$-$C_6$cycloalkoxy, $C_3$-$C_6$cycloalkylamino, $C_3$-$C_6$cycloalkylthio, $C_2$-$C_6$alkenyloxy, halo-$C_2$-$C_6$alkenyloxy, $C_1$-$C_6$alkylthio, halo-$C_1$-$C_6$alkylthio, $C_2$-$C_6$alkenylthio, halo-$C_2$-$C_6$alkenylthio, $C_1$-$C_6$alkylamino, di-$C_1$-$C_6$alkylamino, $C_1$-$C_6$alkylcarbonyl, halo-$C_1$-$C_6$alkylcarbonyl, $C_1$-$C_6$alkoxycarbonyl, $C_1$-$C_6$alkylaminocarbonyl, di-$C_1$-$C_6$alkylaminocarbonyl, unsubstituted or one- or poly-substituted phenylamino, unsubstituted or one- or poly-substituted phenylcarbonyl, unsubstituted or one- or poly-substituted phenyl, unsubstituted or one- or poly-substituted phenoxy, or unsubstituted or one- or poly-substituted pyridyloxy, whereby the substituents in each case can be independent of one another and are chosen from the group consisting of $R_1$ and halogen;

preferably halogen, cyano, $C_1$-$C_6$alkyl, halo-$C_1$-$C_6$alkyl, $C_1$-$C_6$alkoxy, halo-$C_1$-$C_6$alkoxy, unsubstituted or one- or poly-substituted phenyl, or unsubstituted or one- or poly-substituted phenoxy, whereby the substituents in each case can be independent of one another and are halogen;

most preferably halo-$C_1$-$C_6$alkyl, or unsubstituted or one- or di-substituted phenoxy, whereby the substituents can be independent of one another and are halogen;

(6) A compound of the formula I, wherein $R_9$ is halogen, nitro, cyano, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, halo-$C_2$-$C_6$alkenyl, $C_2$-$C_6$alkynyl, $C_3$-$C_6$cycloalkyl, $C_3$-$C_6$cycloalkoxy, $C_3$-$C_6$cycloalkylamino, $C_3$-$C_6$cycloalkylthio, $C_2$-$C_6$alkenyloxy, halo-$C_2$-$C_6$alkenyloxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_2$-$C_6$alkenylthio, halo-$C_2$-$C_6$alkenylthio, $C_2$-$C_6$alkenylsulfinyl, halo-$C_1$-$C_6$alkenylsulfinyl, $C_2$-$C_6$alkenylsulfonyl, halo-$C_2$-$C_6$alkenylsulfonyl, $C_1$-$C_6$alkylcarbonyl, halo-$C_1$-$C_6$alkylcarbonyl or $C_1$-$C_6$alkoxycarbonyl;

preferably halogen, cyano, $C_1$-$C_6$alkyl, halo-$C_1$-$C_6$alkyl, $C_1$-$C_6$alkoxy, halo-$C_1$-$C_6$alkoxy, $C_3$-$C_6$cycloalkylthio, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl or halo-$C_1$-$C_6$alkylsulfonyl;

most preferably halo-$C_1$-$C_6$alkyl, halo-$C_1$-$C_6$alkoxy, halo-$C_1$-$C_6$alkylthio, halo-$C_1$-$C_6$alkylsulfinyl or halo-$C_1$-$C_6$alkylsulfonyl;

(7) A compound of the formula I, wherein a is 1, 2 or 3;

preferably 1 or 2;

most preferably 1;

(8) A compound of the formula I, wherein b is 0, 1, 2 or 3;

preferably 0, 1 or 2;

most preferably 0;

(9) A compound of the formula I, wherein m, n, o and p are, independent of each other, 0, 1, 2, 3 or 4;

preferably, independent of each other, 0, 1, 2 or 3;

more preferably, independent of each other, 0, 1 or 2;

most preferably, independent of each other, 0 or 1;

with the proviso that m and p are not equal to 0 at the same time;

(10) A compound of the formula I, wherein

W is O, S, $S(O_2)$ or $N(R_1)$;

preferably O or S;

most preferably O;

(11) A compound of the formula I, wherein

Y is O or S;

preferably O;

(12) A compound of the formula I, wherein

Ar is unsubstituted or one- or poly-substituted aryl;

$R_1$ is hydrogen, $C_1$-$C_6$alkyl, halo-$C_1$-$C_6$alkyl, allyl or $C_1$-$C_6$alkoxymethyl;

$R_2$, $R_3$, $R_4$, $R_5$ and $R_6$ are either, independently of one another, hydrogen, halogen, unsubstituted or one- or poly -substituted $C_1C_4$alkyl, unsubstituted or one- or poly-substituted $C_2$-$C_4$alkenyl, unsubstituted or one- or poly-substituted $C_2$-$C_4$alkinyl or unsubstituted or one- or poly-substituted $C_1$-$C_4$alkoxy, whereby the substituents in each case can be independent of one another and are chosen from the group consisting of halogen, $C_1$-$C_6$alkoxy and halo-$C_1$-$C_6$alkoxy; or $R_2$ and $R_3$ are together $C_2$-$C_4$alkylene;

$R_7$ and $R_{10}$ are, independently of each other, $NH_2$, OH, SH, carboxy, aminocarbonyl, aminothiocarbonyl, aminothiocarbonyloxy, ureyl, thioureyl, $(C_1$-$C_6$-alkyl$)_2$aminothiocarbonyl, phenylaminothiocarbonyl, $C_1$-$C_6$alkylsulfanylcarbonyl, $C_1$-$C_6$alkylcarbonylsulfanyl, halo-$C_2$-$C_6$alkynyl, $C_1$-$C_6$alkylaminothiocarboxy, $C_1$-$C_6$alkyloxythiocarboxy, $C_1$-$C_6$alkylaminothiocarboxamido, (1,3)-oxathiolyl, 2-halo-(1,3)-oxathiolyl, (1,3)-dioxolyl, 2-halo-(1,3)-dioxolyl, sulfonyl, aminosulfonyl, $C_1$-$C_6$alkylaminosulfonyl, di-$C_1$-$C_6$alkylaminosulfonyl, $C_1$-$C_6$alkyloxysulfonyl, $C_1$-$C_6$alkylaminocarbonylsulfanyl, or $C_1$-$C_6$alkyloxythiocarbonyl;

$R_8$ is halogen, nitro, cyano, $C_1$-$C_6$alkyl, halo-$C_1$-$C_6$alkyl, $C_1$-$C_6$alkoxy, halo-$C_1$-$C_6$alkoxy, $C_2$-$C_6$alkenyl, halo-$C_2$-$C_6$alkenyl, $C_2$-$C_6$alkynyl, $C_3$-$C_6$cycloalkyl, C₃-C₆cycloalkoxy, C₃-C₆cycloalkylamino, C₃-C₆cycloalkylthio, C₂-C₆alkenyloxy, halo-C₂-C₆alkenyloxy, C₁-C₆alkylthio, halo-C₁-C₆alkylthio, C₂-C₆alkenylthio, halo-C₂-C₆alkenylthio, C₁-C₆alkylamino, di-C₁-C₆alkylamino, C₁-C₆alkylcarbonyl, halo-C₁-C₆alkylcarbonyl, C₁-C₆alkoxycarbonyl, C₁-C₆alkylaminocarbonyl, di-C₁-C₆alkylaminocarbonyl, unsubstituted or one- or poly-substituted phenylamino, unsubstituted or one- or poly-substituted phenylcarbonyl, unsubstituted or one- or poly-substituted phenyl, unsubstituted or one- or poly-substituted phenoxy, or unsubstituted or one- or poly-substituted pyridyloxy, whereby the substituents in each case can be independent of one another and are chosen from the group consisting of R₁ and halogen;

R₉ is halogen, nitro, cyano, C₁-C₆alkyl, halo-C₁-C₆alkyl, C₁-C₆alkoxy, halo-C₁-C₆alkoxy, C₂-C₆alkenyl, halo-C₂-C₆alkenyl, C₂-C₆alkynyl, C₃-C₆cycloalkyl, C₃-C₆cycloalkoxy, C₃-C₆cycloalkylamino, C₃-C₆cycloalkylthio, C₂-C₆alkenyloxy, halo-C₂-C₆alkenyloxy, C₁-C₆alkylthio, halo-C₁-C₆alkylthio, C₁-C₆alkylsulfinyl, halo-C₁-C₆alkylsulfinyl, C₁-C₆alkylsulfonyl, halo-C₁-C₆alkylsulfonyl, C₂-C₆alkenylthio, halo-C₂-C₆alkenylthio, C₂-C₆alkenylsulfinyl, halo-C₂-C₆alkenylsulfinyl, C₂-C₆alkenylsulfonyl, halo-C₂-C₆alkenylsulfonyl, C₁-C₆alkylcarbonyl, halo-C₁-C₆alkylcarbonyl or C₁-C₆alkoxycarbonyl;

a is 1, 2 or 3;
b is 0, 1, 2 or 3;
m, n, o and p are, independent of each other, 0, 1, 2, 3 or 4;
W is O, S, S(O₂) or N(R₁); and
Y is O or S;
with the proviso that m and p are not equal to 0 at the same time;

(13) A compound of the formula I, wherein
Ar is one- or di-substituted aryl;
R₁ is hydrogen, C₁-C₄alkyl or halo-C₁-C₄alkyl;
R₂, R₃, R₄, R₅ and R₆ are either, independently of one another, hydrogen, halogen, unsubstituted or one- or poly-substituted C₁C₄alkyl, whereby the substituents in each case can be independent of one another and are chosen from at the group consisting of halogen, C₁-C₆alkoxy and halo-C₁-C₆alkoxy; or R₂ and R₃ are together C₁-C₄alkylene;
R₇ and R₁₀ are, independently of each other, carboxy, aminocarbonyl, (1,3)-dioxolyl or 2-halo-(1,3)-dioxolyl;
R₈ is halogen, cyano, C₁-C₆alkyl, halo-C₁-C₆alkyl, C₁-C₆alkoxy, halo-C₁-C₆alkoxy, unsubstituted or one- or poly-substituted phenyl, or unsubstituted or one- or poly-substituted phenoxy, whereby the substituents in each case can be independent of one another and are halogen;
R₉ is halogen, cyano, C₁-C₆alkyl, halo-C₁-C₆alkyl, C₁-C₆alkoxy, halo-C₁-C₆alkoxy, C₃-C₆cycloalkylthio, C₁-C₆alkylthio, halo-C₁-C₆alkylthio, C₁-C₆alkylsulfinyl, halo-C₁-C₆alkylsulfinyl, C₁-C₆alkylsulfonyl or halo-C₁-C₆alkylsulfonyl;
a is 1 or 2;
b is 0, 1 or 2;
m, n, o and p are, independent of each other, 0, 1, 2 or 3;
W is O or S; and
Y is O;
with the proviso that m and p are not equal to 0 at the same time;

(14) A compound of the formula I, wherein
Ar is one- or di-substituted aryl;
R₁ is hydrogen or C₁-C₂alkyl;
R₂, R₃, R₄, R₅ and R₆ are either, independently of one another, hydrogen, halogen,
R₇ and R₁₀ are, independently of each other, carboxy or aminocarbonyl;
R₈ is halo-C₁-C₆alkyl, or unsubstituted or one- or di-substituted phenoxy, whereby the substituents can be independent of one another and are halogen;
R₉ is halo-C₁-C₆alkyl, halo-C₁-C₆alkoxy, halo-C₁-C₆alkylthio, halo-C₁-C₆alkylsulfinyl or halo-C₁-C₆alkylsulfonyl;
a is 1;
b is 0;
m, n, o and p are, independent of each other, 0 or 1;
W and Y is O;
with the proviso that m and p are not equal to 0 at the same time.

The compounds of the formula I listed in Table 1 are particularly preferred within the context of the invention and the compounds of the formula I mentioned in the synthetic examples are very particularly preferred.

A further subject-matter of the invention is the process for the preparation of the compounds of the formula I, where Y is O, in each case in the free form or in the salt form, e.g. which comprises the reaction of a compound of the formula

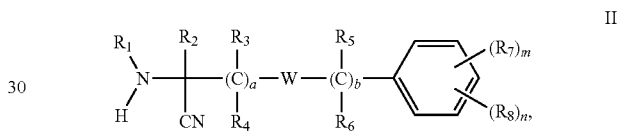

II which is known or can be prepared by analogy to relevant known compounds and in which R₁, R₂, R₃, R₄, R₅, R₆, R₇, R₈, W, a, b, m and n are as defined above in the formula I, with a compound of the formula

III which is known or can be prepared by analogy to relevant known compounds and in which Ar, R₉, R₁₀, o and p are as defined above in the formula I and Q is a leaving group, if desired in the presence of a basic catalyst, and in each case, if desired, the conversion of a compound of the formula I obtainable according to the process or in another way, in each case in the free form or in the salt form, to another compound of the formula I, the separation of a mixture of isomers obtainable according to the process and the isolation of the desired isomer and/or the conversion of a free compound of the formula I obtainable according to the process to a salt or the conversion of a salt of a compound of the formula I obtainable according to the process to the free compound of the formula I or to another salt.

That which has been said above for salts of compounds I applies analogously to starting materials mentioned hereinabove and hereinafter with regard to the salts thereof.

The reactants can be reacted with one another as such, i.e. without addition of a solvent or diluent, e.g. in the molten form. For the most part, however, it is advantageous to add an inert solvent or diluent or a mixture thereof. Mention may be made, as examples of such solvents or diluents, of: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethyl-formamide, N,N-diethylformamide, N,N-dimethylacetamide, N-methylpyrrolidone or hexamethylphosphoramide; nitriles, such as acetonitrile or propionitrile; and sulfoxides, such as dimethyl sulfoxide.

Preferred leaving groups Q are OH, halogens, tosylates, mesylates and triflates, particularly preferably halogens, especially chlorine.

Suitable bases for facilitating the reaction are, e.g., alkali metal or alkaline earth metal hydroxides, hydrides, amides, alkoxides, acetates, carbonates, dialkylamides or alkyl-silylamides, alkylamines, alkylenediamines, if desired N-alkylated and saturated or unsaturated, cycloalkylamines, basic heterocycles, ammonium hydroxides and carbocyclic amines. Mention may be made, by way of examples, of sodium hydroxide, sodium hydride, sodamide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-Cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reaction is advantageously carried out at a temperature from approximately 0° C. to approximately +150° C., preferably from approximately 20° C. to approximately +100° C.

A further subject-matter of the invention is the process for the preparation of the compounds of the formula I, where Y is S, in each case in the free form or in the salt form, e.g. which comprises the reaction of a compound of the formula I, where Y is O, with a sulfonating agent, preferably $P_4S_{10}$, if desired in the presence of a basic catalyst, and in each case, if desired, the conversion of a compound of the formula I obtainable according to the process or in another way, in each case in the free form or in the salt form, to another compound of the formula I, the separation of a mixture of isomers obtainable according to the process and the isolation of the desired isomer and/or the conversion of a free compound of the formula I obtainable according to the process to a salt or the conversion of a salt of a compound of the formula I obtainable according to the process to the free compound of the formula I or to another salt.

A further subject-matter of the invention is the process for the preparation of the compounds of the formula I, where Y is $NR_{11}$, in each case in the free form or in the salt form, e.g. which comprises the reaction of a compound of the formula I, where Y is S, with a compound of formula $NHR_{11}$, which is known or can be prepared by analogy to relevant known compounds and in which $R_{11}$ is as defined above in the formula I, if desired in the presence of a basic catalyst, and in each case, if desired, the conversion of a compound of the formula I obtainable according to the process or in another way, in each case in the free form or in the salt form, to another compound of the formula I, the separation of a mixture of isomers obtainable according to the process and the isolation of the desired isomer and/or the conversion of a free compound of the formula I obtainable according to the process to a salt or the conversion of a salt of a compound of the formula I obtainable according to the process to the free compound of the formula I or to another salt.

Salts of compounds I can be prepared in a way known per se. Thus, for example, acid addition salts of compound I are obtained by treatment with a suitable acid or a suitable ion-exchange reagent and salts with bases are obtained by treatment with a suitable base or a suitable ion-exchange reagent.

Salts of compounds I can be converted in the usual way to the free compounds I, acid addition salts, e.g. by treatment with a suitable basic agent or a suitable ion exchange reagent, and salts with bases, e.g. by treatment with a suitable acid or a suitable ion-exchange reagent.

Salts of compounds I can be changed in a way known per se to other salts of compounds I, acid addition salts for example to other acid addition salts, e.g. by treatment of a salt of an inorganic acid, such as a hydrochloride, with a suitable metal salt, such as a sodium, barium or silver salt, of an acid, e.g. with silver acetate, in a suitable solvent, in which an inorganic salt, e.g. silver chloride, being formed is insoluble and for this reason precipitates from the reaction mixture.

According to the method or reaction conditions, the compounds I with salt-forming properties can be obtained in the free form or in the form of salts.

The compounds I can also be obtained in the form of their hydrates and/or can incorporate other solvents, which might, for example, be used in the crystallization of compounds existing in the solid form.

The compounds I can exist in the form of one of the possible isomers or as a mixture of the same, e.g., according to the number, absolute and relative configuration of the asymmetric carbon atoms, as pure isomers, for example optical isomers and/or diastereoisomers, or as mixtures of isomers, such as mixtures of enantiomers, e.g. racemates, mixtures of diastereoisomers or racemate mixtures; the invention relates both to the pure isomers and to all possible mixtures of isomers and is to be correspondingly understood in each case heretofore and hereinafter, even if stereochemical details are not specifically referred to in every case.

Mixtures of diastereoisomers and mixtures of racemates of compounds I obtainable according to the process—depending on the choice of the starting materials and operating methods—or otherwise obtainable can be separated in a known way into the pure diastereoisomers or racemates on the basis of the physicochemical differences of the components, for example by fractional crystallization, distillation and/or chromatography.

Correspondingly obtainable mixtures of enantiomers, such as racemates, can be resolved into the optical isomers by known methods, for example by recrystallization from an optically active solvent, by chromatography on chiral adsorbents, e.g. high performance liquid chromatography (HPLC) on acetylcellulose, with the help of suitable microorganisms, by cleavage with specific immobilized enzymes, via the formation of inclusion complexes, e.g. by using chiral crown ethers, in which only one enantiomer is complexed.

In addition to through separation of the corresponding mixtures of isomers, pure diastereoisomers or enantiomers according to the invention can also be obtained through generally known methods of diastereoselective or enantioselective synthesis, e.g. by carrying out the process according to the invention with educts with correspondingly suitable stereochemistry.

Advantageously, the biologically more effective isomer, e.g. enantiomer, or mixture of isomers, e.g. mixture of enantiomers, is isolated or synthesized each time, provided that the individual components have different biological activity.

In the process of the present invention, use is preferably made of such starting materials and intermediates which result in the compounds I described at the beginning as particularly valuable.

The invention in particular relates to the preparation process described in the example.

Starting materials and intermediates used according to the invention for the preparation of the compounds I which are novel, their use and processes for their preparation likewise form a subject-matter of the invention.

The compounds I according to the invention are characterized by a particularly broad activity spectrum and are valuable active ingredients in the field of pest control which are well tolerated by warm-blooded species, fish and plants, including in particular for controlling endo- and ectoparasites which parasitize animals.

In the context of the present invention, the term "ectoparasites" is understood to mean, in particular, insects, mites and ticks. This includes insects of the orders: Lepidoptera, Coleoptera, Homoptera, Heteroptera, Diptera, Thysanoptera, Orthoptera, Anoplura, Siphonaptera, Mallophaga, Thysanura, isoptera, Psocoptera and Hymenoptera. However, reference may in particular be made to ectoparasites which are a nuisance to man or animals and which transmit pathogens, for example flies, such as *Musca domestica, Musca vetustissima, Musca autumnalis, Fannia canicularis, Sarcophaga camaria, Lucilia cuprina, Hypoderma bovis, Hypoderma lineatum, Chrysomyia chforopyga, Dermatobia hominis, Cochliomyia hominivorax, Gasterophilus intestinalis, Oestrus ovis, Stomoxys calcitrans, Haematobia irritans*, and mosquitoes (*Nematocera*), such as *Culicidae, Simuliidae, Psychodidae*, but also bloodsucking parasites, for example fleas, such as *Ctenocephalides felis* and *Ctenocephalides canis* (cat and dog fleas), *Xenopsylla cheopis, Pulex irritans, Dermatophilus penefrans*, lice, such as *Damalina ovis, Pediculus humanis*, stable flies and horse flies (*Tabanidae*), *Haematopota* spp., such as *Haematopota pluvialis, Tabanidea* spp., such as *Tabanus nigrovittatus, Chrysopsinae* spp., such as *Chrysops caecutiens*, tsetse flies, such as *Glossinia* species, biting insects, in particular cockroaches, such as *Blatella germanica, Blatta orientalis, Periplaneta americana*, mites, such as *Dermanyssus gallinae, Sarcoptes scabiei, Psoroptes ovis* and *Psorergates* spp., and last but not least ticks. The latter belong to the order Acarina. Known representatives of ticks are, e.g., *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals, including farm animals, such as cows, pigs, sheep and goats, poultry, such as chickens, turkeys and geese, fur-bearing animals, such as mink, foxes, chinchillas, rabbits and the like, and pets, such as cats and dogs, but also man.

The compounds I according to the invention are also effective against all or individual development stages of normally sensitive but also of resistant animal pests, such as insects and representatives of the order Acarina. The insecticidal, ovicidal and/or acaricidal action of the active ingredients according to the invention may in the process be displayed directly, i.e. in killing the pests, which occurs immediately or only after some time, for example during moulting, or their eggs, or indirectly, e.g. in reduced egg laying and/or in a reduced hatching rate, in which the good action corresponds to a kill rate (mortality) of at least 50 to 60%.

The compounds I can also be used against hygiene pests, in particular of the order Diptera with the families Sarcophagidae, Anophilidae and Culicidae; of the orders Orthoptera, Dictyoptera (e.g. the family Blattidae) and Hymenoptera (e.g. the family Formicidae).

The compounds I also have lasting activity in the case of phytoparasitic mites and insects. In the case of spider mites of the order Acarina, they are active against eggs, nymphs and adults of Tetranychidae (*Tetranychus* spp. and *Panonychus* spp.).

They are highly active in the case of the sucking insects of the order Homoptera, in particular against pests of the families Aphididae, Delphacidae, Cicadellidae, Psyllidae, Loccidae, Diaspididae and Eriophydidae (e.g. citrus rust mite); of the orders Hemiptera, Heteroptera and Thysanoptera, and in the case of the phytophagous insects of the orders Lepidoptera, Coleoptera, Diptera and Orthoptera.

They are also suitable as soil insecticides against pests in the soil.

The compounds of the formula I are accordingly active against all development stages of sucking and feeding insects on crops such as cereals, cotton, rice, maize, soya beans, potatoes, vegetables, fruit, tobacco, hops, citrus fruit, avocados and others.

The compounds of the formula I are also active against plant nematodes of the genera *Meloidogyne, Heterodera, Pratylenchus, Ditylenchus, Radopholus, Rizoglyphus* and others.

The compounds are particularly active against helminths, among which the endoparasitic nematodes and trematodes can be the cause of serious diseases in mammals and poultry, e.g. in sheep, pigs, goats, cattle, horses, donkeys, dogs, cats, guinea pigs and ornamental birds. Typical nematodes of this indication are: *Haemonchus, Trichostrongylus, Ostertagia, Nematodirus, Cooperia, Ascaris, Bunostonum, Oesophagostonum, Chabertia, Trichuris, Strongylus, Trichonema, Dictyocaulus, Capilaria, Heterakis, Toxocara, Ascaridia, Oxyuris, Ancylostoma, Uncinaria, Toxascaris* and *Parascaris*. Mention may specifically be made, among the trematodes, of the family of the Fasciolideae, in particular *Fasciola hepatica*. The particular advantage of the compounds of the formula I is their activity against such parasites, which are resistant to benzimidazole-based active ingredients.

Certain species of the genera *Nematodirus, Cooperia* and *Oesophagostonum* attack the intestinal tract of the host animal, while others of the genera *Haemonchus* and *Ostertagia* parasitize in the stomach and others of the genus *Dictyocaulus* parasitize in lung tissue. Parasites of the families Filariidae and Setariidae are found in internal cell tissue and in organs, e.g. the heart, blood vessels, lymph vessels and subcutaneous tissue. Mention may particularly be made here of the dog heartworm, *Dirofilaria immitis*. The compounds of the formula I are highly effective against these parasites.

The pests which can be controlled with the compounds of the formula I also include, from the class Cestoda (tapeworms), the families Mesocestoidae, in particular the genus *Mesocestoides*, especially *M. lineatus*; Dilepididae, in particular *Dipylidium caninum, Joyeuxielia* spp., especially *Joyeuxiella pasquali*, and *Diplopylidium* spp.; and Taeniidae, in particular *Taenia pisiformis, Taenia cervi, Taenia ovis, Taenia hydatigena, Taenia multiceps, Taenia taeniaeformis, Taenia serialis* and *Echinocuccus* spp., particularly preferably *Taenia hydatigena, Taenia ovis, Taenia multiceps, Taenia serialis; Echinocuccus granulosus* and *Echinococcus granulosus* and *Echinococcus multilocularis*, and *Multiceps multiceps*.

In a very particularly preferred way, *Taenia hydatigena, T. pisiformis, T. ovis, T. taeniae-formis, Multiceps multiceps, Joyeuxiella pasquali, Dipylidium caninum, Mesocestoides* spp., *Echinococcus granulosus* and *E. multilocularis* are controlled simultaneously with *Dirofilaria immitis, Ancylostoma* spp., *Toxocara* spp. and/or *Trichuris vulpis* on or in dogs and cats. Also in a preferred way, *Ctenocephalides felis* and/or *C. canis* are controlled simultaneously with the abovementioned nematodes and cestodes.

The compounds of the formula I are also suitable for controlling parasites which are pathogenic to man, among which may be mentioned, as typical representatives occurring in the digestive tract, those of the genera *Ancylostoma, Necator, Ascaris, Strongyloides, Trichinella, Capillaria, Trichuris* and *Enterobius*. The compounds of the present invention are also active against parasites of the genera *Wuchereria, Brugia, Onchocerca* and *Loa* from the family of the Filariidae, which occur in the blood, in tissue and in various organs, and also against *Dracunculus* and parasites of the genera *Strongyloides* and *Trichinella*, which specifically infect the gastrointestinal tract.

In addition, the compounds of the formula I are also active against harmful fungi which cause disease in plants and in man and animals.

The good pesticidal action of the compounds of the formula I according to the invention corresponds to a kill rate (mortality) of at least 50-60% of the pests mentioned. In particular, the compounds of the formula I are characterized by an extraordinarily long duration of action.

The compounds of the formula I are used as such or preferably together with the auxiliaries conventional in formulation technology and can accordingly be processed in a known way, for example to emulsifiable concentrates, directly dilutable solutions, dilute emulsions, soluble powders, granules and also encapsulations in polymer substances. The application methods as well as the compositions are chosen in accordance with the intended aims and the prevailing circumstances.

The formulation, i.e. the compositions, preparations or combinations comprising the active ingredient of the formula I, or combinations of these active ingredients with other active ingredients, and, if desired, a solid or liquid additive, is prepared in a known way, for example by intimately mixing and/or grinding the active ingredients with extenders, for example with solvents, solid carriers and, if desired, surface-active compounds (surfactants).

The following are possible as solvents: alcohols, such as ethanol, propanol or butanol, and glycols, and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methyl-2-pyrrolidone, dimethyl sulfoxide, dimethylformamide or water, vegetable oils, such as rapeseed oil, castor oil, coconut oil or soybean oil; and, if desired, silicone oils.

Preferred application forms for use in warm-blooded animals for controlling helminths include solutions, emulsions, suspensions (drenches), feed additives, powders, tablets, including effervescent tablets, boluses, capsules, microencapsulations and pour-on formulations, care having to be taken over the physiological compatibility of the formulation auxiliaries.

Suitable binders for tablets and boluses are chemically modified polymeric natural products which are soluble in water or alcohol, such as starch, cellulose or protein derivatives (e.g., methylcellulose, carboxymethylcellulose, ethylhydroxyethylcellulose, proteins, such as zein, gelatin, and the like), and synthetic polymers, for example polyvinyl alcohol, polyvinylpyrrolidone, and the like. Tablets also comprise fillers (e.g., starch, microcrystalline cellulose, sugar, lactose, and the like), lubricants and disintegrating agents.

If the anthelmintic compositions are present in the form of feed concentrates, then high-performance feed, feed cereals or protein concentrates, for example, are used as carriers. Such feed concentrates or compositions can, in addition to the active ingredients, also comprise additives, vitamins, antibiotics, chemotherapeutics, or other pesticides, mainly bacteriostats, fungistats, coccidiostats, or also hormone preparations, anabolics or substances which promote growth, influence the quality of meat from animals for slaughter or are useful to the organism in another way. If the compositions or the active ingredients of the formula I present therein are added directly to the feed or to the drinking water for the animals, the finished feed or the finished drinking water comprises the active ingredients preferably in a concentration from approximately 0.0005 to 0.02% by weight (5-200 ppm).

The compounds of the formula I according to the invention can be used alone or in combination with other biocides. They can, e.g., be combined with pesticides possessing the same direction of action, in order to enhance the action, or can be combined with substances possessing another direction of action, in order to broaden the activity spectrum. It may also make sense to add substances which repel, known as repellents. If it is desired to expand the activity spectrum with regard to endoparasites, for example worms, the compounds of the formula I are appropriately combined with substances having endoparasiticidal properties. They can also, naturally, be used in combination with antibacterial compositions. Since the compounds of the formula I represent adulticides, i.e. since they are effective in particular against the adult stages of the target parasites, the addition of pesticides which are more likely to attack the juvenile stages of parasites can be highly advantageous. In this way, most of those parasites causing great economic damage are namely included. In addition, a substantial contribution is also made as well to avoiding the formation of resistance. Some combinations can also lead to synergistic effects, i.e. that the total amount of active substance consumed can be reduced, which is desirable from an ecological viewpoint. Preferred groups of combination participants and particularly preferred combination participants are mentioned subsequently, which combinations can, in addition to a compound of the formula I, comprise one or more of these participants.

Suitable participants in the mixture include biocides, for example the insecticides and acaricides with different mechanisms of action mentioned subsequently and sufficiently known to a person skilled in the art, for example chitin synthesis inhibitors, growth regulators; active ingredients which act as juvenile hormones; active ingredients which act as adulticides; broad spectrum insecticides, broad spectrum acaricides and nematicides; but also the sufficiently known anthelmintics and substances which repel insects and/or members of the Acarina, known as repellents or detachers.

Nonlimiting examples of suitable insecticides and acaricides are:

1. Abamectin
2. AC 303 630
3. Acephate
4. Acrinathrin
5. Alanycarb

-continued

6. Aldicarb
7. α-Cypermethrin
8. Alphamethrin
9. Amitraz
10. Avermectin B$_1$
11. AZ 60541
12. Azinphos E
13. Azinphos-methyl
14. Azocyclotin
15. *Bacillus subtil.* toxin
16. Bendiocarb
17. Benfuracarb
18. Bensultap
19. β-Cyfluthrin
20. Bifenthrin
21. BPMC
22. Brofenprox
23. Bromophos E
24. Bufencarb
25. Buprofezin
26. Butocarboxim
27. Butylpyridaben
28. Cadusafos
29. Carbaryl
30. Carbofuran
31. Carbophenothion
32. Cartap
33. Cloethocarb
34. Chlorethoxyfos
35. Chlorfenapyr
36. Chlorfluazuron
37. Chlormephos
38. Chlorpyrifos
39. Cis-Resmethrin
40. Clocythrin
41. Clofentezine
42. Cyanophos
43. Cycloprothrin
44. Cyfluthrin
45. Cyhexatin
46. D 2341
47. Deltamethrin
48. Demeton M
49. Demeton S
50. Demeton-S-methyl
51. Dichlofenthion
52. Dicliphos
53. Diethion
54. Diflubenzuron
55. Dimethoate
56. Dimethylvinphos
57. Dioxathion
58. DPX-MP062
59. Edifenphos
60. Emamectin
61. Endosulfan
62. Esfenvalerate
63. Ethiofencarb
64. Ethion
65. Ethofenprox
66. Ethoprophos
67. Etrimfos
68. Fenamiphos
69. Fenazaquin
70. Fenbutatin oxide
71. Fenitrothion
72. Fenobucarb
73. Fenothiocarb
74. Fenoxycarb
75. Fenpropathrin
76. Fenpyrad
77. Fenpyroximate
78. Fenthion
79. Fenvalerate
80. Fipronil
81. Fluazinam
82. Fluazuron
83. Flucycloxuron
84. Flucythrinate
85. Flufenoxuron
86. Flufenprox
87. Fonofos
88. Formothion
89. Fosthiazate
90. Fubfenprox
91. HCH
92. Heptenophos
93. Hexaflumuron
94. Hexythiazox
95. Hydroprene
96. Imidacloprid
97. Insect-active fungi
98. Insect-active nematodes
99. Insect-active viruses
100. Iprobenfos
101. Isofenphos
102. Isoprocarb
103. Isoxathion
104. Ivermectin
105. λ-Cyhalothrin
106. Lufenuron
107. Malathion
108. Mecarbam
109. Mesulfenfos
110. Metaldehyde
111. Methamidophos
112. Methiocarb
113. Methomyl
114. Methoprene
115. Metolcarb
116. Mevinphos
117. Milbemectin
118. Moxidectin
119. Naled
120. NC 184
121. NI-25, Acetamiprid
122. Nitenpyram
123. Omethoate
124. Oxamyl
125. Oxydemeton M
126. Oxydeprofos
127. Parathion
128. Parathion-methyl
129. Permethrin
130. Phenthoate
131. Phorate
132. Phosalone
133. Phosmet
134. Phoxim
135. Pirimicarb
136. Pirimiphos E
137. Pirimiphos M
138. Promecarb
139. Propaphos
140. Propoxur
141. Prothiofos
142. Prothoate
143. Pyraclofos
144. Pyridaphenthion
145. Pyresmethrin
146. Pyrethrum
147. Pyridaben
148. Pyrimidifen
149. Pyriproxyfen
150. RH-5992
151. RH-2485
152. Salithion
153. Sebufos
154. Silafluofen
155. Spinosad
156. Sulfotep
157. Sulprofos
158. Tebufenozide
159. Tebufenpyrad
160. Tebupirimfos
161. Teflubenzuron
162. Tefluthrin -continued 163. Temephos
164. Terbam
165. Terbufos
166. Tetrachlorvinphos
167. Thiafenox
168. Thiodicarb
169. Thiofanox
170. Thionazin
171. Thuringiensin
172. Tralomethrin
173. Triarathene
174. Triazamate
175. Triazophos
176. Triazuron
177. Trichlorfon
178. Triflumuron
179. Trimethacarb
180. Vamidothion
181. XMC (3,5-xylyl methylcarbamate)
182. Xylylcarb
183. YI 5301/5302
184. ζ-Cypermethrin
185. Zetamethrin Nonlimiting examples of suitable anthelmintics are mentioned subsequently, in which some representatives, in addition to the anthelmintic activity, also have an insecticidal and acaricidal activity and are already included in the above list:

(A1) Praziquantel=2-Cyclohexylcarbonyl-4-oxo-1,2,3,6,7,11b-hexahydro-4H-pyrazino[2,1-a]isoquinoline (A2) Glosantel=3,5-Diiodo-N-[5-chloro-2-methyl-4-(α-cyano-4-chlorobenzyl)phenyl]-salicylamide (A3) Triclabendazole=5-Chloro-6-(2,3-dichlorophenoxy)-2-methylthio-1H-benzimidazole (A4) Levamisole=L-(−)-2,3,5,6-Tetrahydro-6-phenylimidazo[2,1-b]thiazole (A5) Mebendazole=Methyl 5-benzoyl-1H-benzimidazol-2-ylcarbamate (A6) Omphalotin=a macrocyclic fermentation product from the fungus *Omphalotus olearius* disclosed in WO 97/20857

(A7) Abamectin=Avermectin B1

(A8) Ivermectin=22,23-Dihydroavermectin B1

(A9) Moxidectin=5-O-Demethyl-28-deoxy-25-(1,3-dimethyl-1-butenyl)-6,28-epoxy-23-(methoxyimino)milbemycin B (A10) Doramectin=25-Cyclohexyl-5-O-demethyl-25-de(1-methylpropyl)avermectin A1a (A11) Milbemectin=Mixture of Milbemycin A3 and Milbemycin A4

(A12) Milbemycin oxime=5-Oxime of Milbemectin

Nonlimiting examples of suitable repelling substances (repellents or detachers) are:

(R1) DEET (N,N-Diethyl-m-toluamide)

(R2) KBR 3023 N-Butyl-2-oxycarbonyl-2-(2-hydroxyethyl)piperidine (R3) Cymiazole=N-2,3-Dihydro-3-methyl-1,3-thiazol-2-ylidene-2,4-xylidine The participants in the mixture which are mentioned are very well known to a person skilled in the art. Most are described in the various editions of The Pesticide Manual, The British Crop Protection Council, London, others in the various editions of The Merck Index, Merck & Co. Inc., Rahway, N.J., USA, or in the patent literature. The following listing is accordingly restricted to a few references by way of examples.

(I) 2-Methyl-2-(methylthio)propionaldehyde O-methylcarbamoyloxime (Aldicarb), from The Pesticide Manual, 11$^{th}$ Ed. (1997), The British Crop Protection Council, London, page 26;

(II) S-(3,4-Dihydro-4-oxobenzo[d][1,2,3]triazin-3-ylmethyl) O,O-dimethyl phosphorodithioate (Azinphos-methyl), from The Pesticide Manual, 11$^{th}$ Ed. (1997), The British Crop Protection Council, London, page 67;

(III) Ethyl N-[2,3-dihydro-2,2-dimethylbenzofuran-7-yloxycarbonyl(methyl)aminothio]-N-isopropyl-β-alaninate (Benfuracarb), from The Pesticide Manual, 11$^{th}$ Ed. (1997), The British Crop Protection Council, London, page 96;

(IV) 2-Methylbiphenyl-3-ylmethyl (2)-(1 RS)-cis-3-(2-chloro-3,3,3-trifluoroprop-1-enyl)-2,2-dimethylcyclopropanecarboxylate (Bifenthrin), from The Pesticide Manual, 11$^{th}$ Ed. (1997), The British Crop Protection Council, London, page 118;

(V) 2-tert-Butylimino-3-isopropyl-5-phenyl-1,3,5-thiadiazinan-4-one (Buprofezin), from The Pesticide Manual, 11$^{th}$ Ed. (1997), The British Crop Protection Council, London, page 157;

(VI) 2,3-Dihydro-2,2-dimethylbenzofuran-7-yl methylcarbamate (Carbofuran), from The Pesticide Manual, 11$^{th}$ Ed. (1997), The British Crop Protection Council, London, page 186;

(VII) 2,3-Dihydro-2,2-dimethylbenzofuran-7-yl (dibutylaminothio)methylcarbamate (Carbosulfan), from The Pesticide Manual, 11$^{th}$ Ed. (1997), The British Crop Protection Council, London, page 188;

(VIII) S,S'-(2-Dimethylaminotrimethylene) bis(thiocarbamate) (Cartap), from The Pesticide Manual, 11$^{th}$ Ed. (1997), The British Crop Protection Council, London, page 193;

(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, 11$^{th}$ Ed. (1997), The British Crop Protection Council, London, page 213;

(X) O,O-Diethyl O-3,5,6-trichloro-2-pyridyl phosphorothioate (Chlorpyrifos), from The Pesticide Manual, 11$^{th}$ Ed. (1997), The British Crop Protection Council, London, page 235;

(XI) (RS)-α-Cyano-4-fluoro-3-phenoxybenzyl (1RS,3RS; 1RS,3RS)-3-(2,2-dichlorovinyl)-2,2-dimethylcyclopropanecarboxylate (Cyfluthrin), from The Pesticide Manual, 11$^{th}$ Ed. (1997), The British Crop Protection Council, London, page 293;

(XII) Mixture of (S)-α-cyano-3-phenoxybenzyl (2)-(1R,3R)-3-(2-chloro-3,3,3-trifluoro-propenyl)-2,2-dimethylcyclopropanecarboxylate and (R)-α-cyano-3-phenoxybenzyl (Z)-(1S,3S)-3-(2-chloro-3,3,3-trifluoropropenyl)-2,2-dimethylcyclopropanecarboxylate (Lambda-Cyhalothrin), from The Pesticide Manual, 11$^{th}$ Ed. (1997), The British Crop Protection Council, London, page 300;

(XIII) Racemate consisting of (S)-α-cyano-3-phenoxybenzyl (1R,3R)-3-(2,2-dichlorovinyl)-2,2-dimethylcyclopropanecarboxylate and (R)-α-cyano-3-phenoxybenzyl (1S,3S)-3-(2,2-dichlorovinyl)-2,2-dimethylcyclopropanecarboxylate (Alpha-cypermethrin), from The Pesticide Manual, 11$^{th}$ Ed. (1997), The British Crop Protection Council, London, page 308;

(XIV) A mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual, 11$^{th}$ Ed. (1997), The British Crop Protection Council, London, page 314;

(XV) (S)-α-Cyano-3-phenoxybenzyl (1R,3R)-3-(2,2-dibromovinyl)-2,2-dimethylcyclopropane-carboxylate (Deltamethrin), from The Pesticide Manual, 11th Ed. (1997), The British Crop Protection Council, London, page 344;

(XVI) 1-(4-Chlorophenyl)-3-(2,6-difluorobenzoyl)urea (Diflubenzuron), from The Pesticide Manual, 11th Ed. (1997), The British Crop Protection Council, London, page 395;

(XVII) (1,4,5,6,7,7-Hexachloro-8,9,10-trinorborn-5-en-2,3-ylenebismethylene) sulfite (Endosulfan), from The Pesticide Manual, 11th Ed. (1997), The British Crop Protection Council, London, page 459;

(XVIII) α-Ethylthio-o-tolyl methylcarbamate (Ethiotencarb), from The Pesticide Manual, 11th Ed. (1997), The British Crop Protection Council, London, page 479;

(XIX) O,O-Dimethyl O-4-nitro-m-tolyl phosphorothioate (Fenitrothion), from The Pesticide Manual, 11th Ed. (1997), The British Crop Protection Council, London, page 514;

(XX) 2-sec-Butylphenyl methylcarbamate (Fenobucarb), from The Pesticide Manual, 11th Ed. (1997), The British Crop Protection Council, London, page 516;

(XXI) (RS)-α-Cyano-3-phenoxybenzyl (RS)-2-(4-chlorophenyl)-3-methylbutyrate (Fenvalerate), from The Pesticide Manual, 11th Ed. (1997), The British Crop Protection Council, London, page 539;

(XXII) S-[Formyl(methyl)carbamoylmethyl]O,O-dimethyl phosphorodithioate (Formothion), from The Pesticide Manual, 11th Ed. (1997), The British Crop Protection Council, London, page 625;

(XXIII) 4-Methylthio-3,5-xylyl methylcarbamate (Methiocarb), from The Pesticide Manual, 11th Ed. (1997), The British Crop Protection Council, London, page 813;

(XXIV) 7-Chlorobicyclo[3.2.0]hepta-2,6-dien-6-yl dimethyl phosphate (Heptenophos), from The Pesticide Manual, 11th Ed. (1997), The British Crop Protection Council, London, page 670;

(XXV) 1-(6-Chloro-3-pyridylmethyl)-N-nitroimidazolidin-2-ylideneamine (Imidacloprid), from The Pesticide Manual, 11th Ed. (1997), The British Crop Protection Council, London, page 706;

(XXVI) 2-Isopropylphenyl methylcarbamate (Isoprocarb), from The Pesticide Manual, 11th Ed. (1997), The British Crop Protection Council, London, page 729;

(XXVII) O,S-Dimethyl phosphoramidothioate (Methamidophos), from The Pesticide Manual, 11th Ed. (1997), The British Crop Protection Council, London, page 808;

(XXVIII) S-Methyl N-(methylcarbamoyloxy)thioacetimidate (Methomyl), from The Pesticide Manual, 11th Ed. (1997), The British Crop Protection Council, London, page 815;

(XXIX) Methyl 3-(dimethoxyphosphinoyloxy)but-2-enoate (Mevinphos), from The Pesticide Manual, 11th Ed. (1997), The British Crop Protection Council, London, page 844;

(XXX) O,O-Diethyl O-4-nitrophenyl phosphorothioate (Parathion), from The Pesticide Manual, 11th Ed. (1997), The British Crop Protection Council, London, page 926;

(XXXI) O,O-Dimethyl O-4-nitrophenyl phosphorothioate (Parathion-methyl), from The Pesticide Manual, 11th Ed. (1997), The British Crop Protection Council, London, page 928;

(XXXII) S-6-Chloro-2,3-dihydro-2-oxo-1,3-benzoxazol-3-ylmethyl O,O-diethyl phosphoro-dithioate (Phosalone), from The Pesticide Manual, 11th Ed. (1997), The British Crop Protection Council, London, page 963;

(XXXIII) 2-Dimethylamino-5,6-dimethylpyrimidin-4-yl dimethylcarbamate (Pirimicarb), from The Pesticide Manual, 11th Ed. (1997), The British Crop Protection Council, London, page 985;

(XXXIV) 2-Isopropoxyphenyl methylcarbamate (Propoxur), from The Pesticide Manual, 11th Ed. (1997), The British Crop Protection Council, London, page 1036;

(XXXV) 1-(3,5-Dichloro-2,4-difluorophenyl)-3-(2,6-difluorobenzoyl)urea (Teflubenzuron), from The Pesticide Manual, 11th Ed. (1997), The British Crop Protection Council, London, page 1158;

(XXXVI) S-tert-Butylthiomethyl O,O-diethyl phosphorodithioate (Terbufos), from The Pesticide Manual, 11th Ed. (1997), The British Crop Protection Council, London, page 1165;

(XXXVII) Ethyl (3-tert-butyl-1-dimethylcarbamoyl-1H-1,2,4-triazol-5-ylthio)acetate, (Triazamate), from The Pesticide Manual, 11th Ed. (1997), The British Crop Protection Council, London, page 1224;

(XXXVIII) Abamectin, from The Pesticide Manual, 11th Ed. (1997), The British Crop Protection Council, London, page 3;

(XXXIX) 2-sec-Butylphenyl methylcarbamate (Fenobucarb), from The Pesticide Manual, 11th Ed. (1997), The British Crop Protection Council, London, page 516;

(XL) N-tert-Butyl-N-(4-ethylbenzoyl)-3,5-dimethylbenzohydrazide (Tebufenozide), from The Pesticide Manual, 11th Ed. (1997), The British Crop Protection Council, London, page 1147;

(XLI) (±)-5-Amino-1-(2,6-dichloro-α,α,α-trifluoro-p-tolyl)-4-trifluoromethylsulfinylpyrazole-3-carbonitrile (Fipronil), from The Pesticide Manual, 11th Ed. (1997), The British Crop Protection Council, London, page 545;

(XLII) (RS)-α-Cyano-4-fluoro-3-phenoxybenzyl (1RS,3RS; 1RS,3SR)-3-(2,2-dichlorovinyl)-2,2-dimethylcyclopropanecarboxylate (beta-Cyfluthrin), from The Pesticide Manual, 11th Ed. (1997), The British Crop Protection Council, London, page 295;

(XLIII) (4-Ethoxyphenyl)[3-(4-fluoro-3-phenoxyphenyl)propyl](dimethyl)silane (Silafluofen), from The Pesticide Manual, 11th Ed. (1997), The British Crop Protection Council, London, page 1105;

(XLIV) tert-Butyl (E)-α-(1,3-dimethyl-5-phenoxypyrazol-4-ylmethyleneamino-oxy)-p-toluate (Fenpyroximate), from The Pesticide Manual, 11th Ed. (1997), The British Crop Protection Council, London, page 530;

(XLV) 2-tert-Butyl-5-(4-tert-butylbenzylthio)-4-chloropyridazin-3(2H)-one (Pyridaben), from The Pesticide Manual, 11th Ed. (1997), The British Crop Protection Council, London, page 1161;

(XLVI) 4-[[4-(1,1-Dimethylethyl)phenyl]ethoxy]quinazoline (Fenazaquin), from The Pesticide Manual, 11th Ed. (1997), The British Crop Protection Council, London, page 507;

(XLVII) 4-Phenoxyphenyl (RS)-2-(2-pyridyloxy)propyl ether (Pyriproxyfen), from The Pesticide Manual, 11th Ed. (1997), The British Crop Protection Council, London, page 1073;

(XLVIII) 5-Chloro-N-{2-[4-(2-ethoxyethyl)-2,3-dimethylphenoxy]ethyl}-6-ethylpyrimidin-4-amine (Pyrimidifen), from The Pesticide Manual, 11th Ed. (1997), The British Crop Protection Council, London, page 1070;

(XLIX) (E)-N-(6-Chloro-3-pyridylmethyl)-N-ethyl-N-methyl-2-nitrovinylidenediamine (Nitenpyram), from The Pesticide Manual, 11th Ed. (1997), The British Crop Protection Council, London, page 880;

(L) (E)-$N^1$-[(6-Chloro-3-pyridyl)methyl]-$N^2$-cyano-$N^1$-methylacetamidine (NI-25, Acetamiprid), from The Pesticide Manual, 11th Ed. (1997), The British Crop Protection Council, London, page 9;

(LI) Avermectin B₁, from The Pesticide Manual, 11th Ed. (1997), The British Crop Protection Council, London, page 3;

(LII) An insect-active extract from a plant, in particular (2R,6aS,12aS)-1,2,6,6a,12,12a-hexahydro-2-isopropenyl-8,9-dimethoxychromeno[3,4-b]furo[2,3-h]chromen-6-one (Rotenone), from The Pesticide Manual, 11th Ed. (1997), The British Crop Protection Council, London, page 1097; and an extract from Azadirachta indica, in particular azadirachtin, from The Pesticide Manual, 11th Ed. (1997), The British Crop Protection Council, London, page 59;

(LIII) A preparation comprising insect-active nematodes, preferably *Heterorhabditis bacteriophora* and *Heterorhabditis megidis*, from The Pesticide Manual, 11th Ed. (1997), The British Crop Protection Council, London, page 671; *Steinemema feltiae*, from The Pesticide Manual, 11th Ed. (1997), The British Crop Protection Council, London, page 1115, and *Steinemema scapterisci*, from The Pesticide Manual, 11th Ed. (1997), The British Crop Protection Council, London, page 1116;

(LIV) A preparation obtainable from *Bacillus subtilis*, from The Pesticide Manual, 11th Ed. (1997), The British Crop Protection Council, London, page 72; or from a *Bacillus thuringiensis* strain except for compounds isolated from GC91 or from NCTC11821; The Pesticide Manual, 11th Ed. (1997), The British Crop Protection Council, London, page 73;

(LV) A preparation comprising insect-active fungi, preferably *Verticillium lecanii*, from The Pesticide Manual, 11th Ed. (1997), The British Crop Protection Council, London, page 1266; *Beauveria brogniartii*, from The Pesticide Manual, 11th Ed. (1997), The British Crop Protection Council, London, page 85; and *Beauveria bassiana*, from The Pesticide Manual, 11th Ed. (1997), The British Crop Protection Council, London, page 83;

(LVI) A preparation comprising insect-active viruses, preferably *Neodipridon Sertifer* NPV, from The Pesticide Manual, 11th Ed. (1997), The British Crop Protection Council, London, page 1342; *Mamestra brassicae* NPV, from The Pesticide Manual, 11th Ed. (1997), The British Crop Protection Council, London, page 759; and *Cydia pomonella* granulosis virus, from The Pesticide Manual, 11th Ed. (1997), The British Crop Protection Council, London, page 291;

(CLXXXI) N'-tert-Butyl-N'-(3,5-dimethylbenzoyl)-3-methoxy-2-methylbenzohydrazide (RH-2485, Methoxyfenozide), from The Pesticide Manual, 11th Ed. (1997), The British Crop Protection Council, London, page 1094;

(CLXXXII) Isopropyl N'-[4-methoxybiphenyl-3-yl]hydrazinecarboxylate (D 2341), from Brighton Crop Protection Conference, 1996, 487-493; and (R2) Book of Abstracts, 212th ACS National Meeting, Orlando, Fla., August 25-29 (1996), AGRO-020. Publisher: American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

Especially preferred combination partners for the compounds of the formula I of the present inventions are the more modern natural or chemically modified macrocyclic lactones (macrolides), such as avermectins, milbemycins and derivatives thereof, including prominent representatives such as Ivermectin, Doramectin, Moxidectin, Selamectin, Emamectin, Eprinomectin, Milbemectin, Abamectin, Milbemycin oxime, Nemadectin, and a derivative thereof, in the free form or in the form of a physiologically acceptable salt.

The combination of these two different classes of compounds leads to several advantageous effects. In the first instant, one observes a broadening of the activity spectrum with regard to the endo-parasites. The combination product is highly active against all sorts of commercially important worms and, what is really surprising, also against metabolic active larval stages. Investigations concerning arrested larval stages are still ongoing but it could well turn out that the combination product will also be effective against these stages.

A further advantage of the combination product is the pest resistance management, meaning that the occurrence of resistance against the compounds of the formula I can drastically be delayed by the administration of the combination product instead of applying the compounds of formula I only. Another advantage is that the combination product can successfully be used even in those cases where the worm population has already developed resistance against a macrocyclic lactones.

Beyond this, a major advantage of the compounds of the formula I is their exhibiting full efficacy against worms resistant to commonly used products such as representatives of the macrocyclic lactones, e.g. Ivermectin or Moxidectin, and to Levamisole or representatives of the benzimidazole class of anthelmintics.

The macrocyclic lactones are most preferred because they exhibit a broad spectrum of activity. Most of them exhibit ecto- and in parallel endo-parsiticidal activity. Therefore, they are also called endectocides. Macrocyclic lactones bind to glutamated chlorine channels causing paralysis of the parasites in the first instance, followed by their death.

In the context of the invention, a preferred group of macrocyclic lactones is represented by compounds of formula

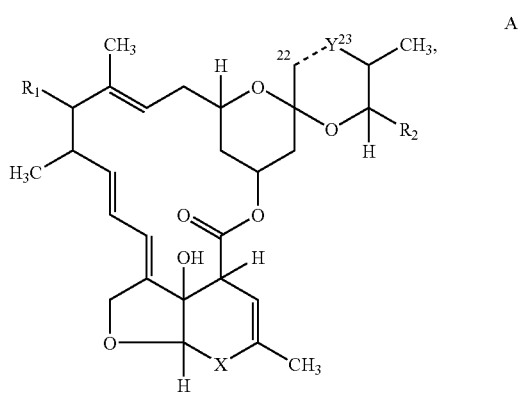

wherein X is —C(H)(OH)—; —C(O)—; or —C(=N—OH)—; Y is —C(H₂)—; =C(H)—; —C(H)(OH)—; or —C(=N—OCH₃)—; R₁ is hydrogen or one of radicals

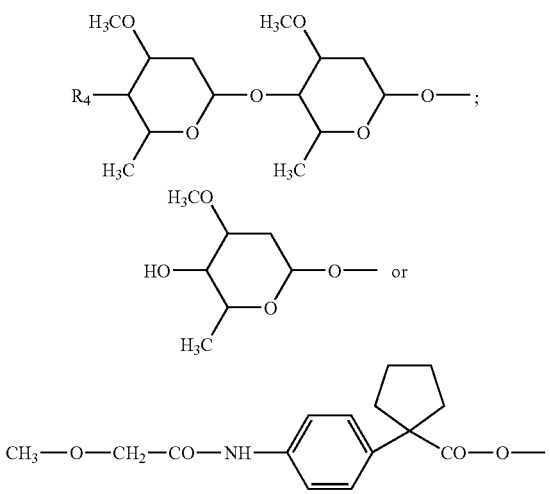

R$_4$ is hydroxyl, —NH—CH$_3$ or —NH—OCH$_3$; R$_2$ is hydrogen, —CH$_3$, —C$_2$H$_5$, —CH(CH$_3$)—CH$_3$, —CH(CH$_3$)—C$_2$H$_5$, —C(CH$_3$)=CH—CH(CH$_3$)$_2$ or cyclohexyl; and if the bond between atoms 22 and 23 represents a double bond the carbon atom in 23-position is unsubstituted so that Y is —C(H)—, or if is the bond between atoms 22 and 23 is a single bond the carbon atom in 23-position is unsubstituted or substituted by hydroxy or by the group =N—O—CH$_3$ so that Y is —C(H$_2$)—; —C(H)(OH)—; or —C(=N—OCH$_3$)—; in free form or in the form of a physiologically acceptable salt.

Typical and especially preferred representatives of compounds of formula A are:

1) Ivermectin is 22,23-Dihydroabamectin; 22,23-dihydroavermectin B1; or 22,23-dihydro-C-076B1, wherein X is —C(H)(OH)—; Y is —C(H$_2$)—; R$_1$ is the radical

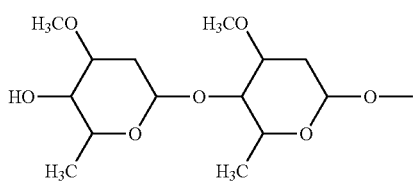

R$_2$ is either —CH(CH$_3$)—CH$_3$ or —CH(CH$_3$)—C$_2$H$_5$ and the bond between atoms 22 and 23 represents a single bond. Ivermectin is known from U.S. Pat. No. 4,199,569.

2) Doramectin is 25-Cyclohexyl-5-O-demethyl-25-de(1-methylpropyl)avermectin A1a, wherein X is —C(H)(OH)—; Y is =C(H)—; R$_1$ is the radical

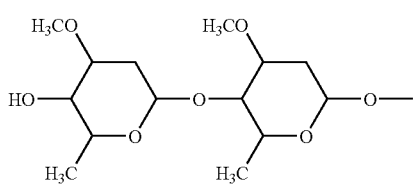

R$_2$ is cyclohexyl and the bond between atoms 22 and 23 represents a double bond. Doramectin is known from U.S. Pat. No. 5,089,480.

3) Moxidectin, is [6R,23E,25S(E)]-5-O-Demethyl-28-deoxy-25-(1,3-dimethyl-1-butenyl)-6,28-epoxy-23-(methoxyimino)milbemycin B, wherein X is —C(H)(OH)—; Y is —C(=N—OCH$_3$)—; R$_1$ is hydrogen; R$_2$ is —C(CH$_3$)=CH—CH(CH$_3$)$_2$; and the bond between atoms 22 and 23 represents a single bond. Moxidectin is known from EP-0,237,339 and U.S. Pat. No. 4,916,154.

4) Selamectin is 25-cyclohexyl-25-de(1-methylpropyl)-5-deoxy-22,23-dihydro-5-(hydroxyimino)avermectin B1 monosaccharide and thus a compound of formula A, wherein X is —C(=N—OH)—; Y is —C(H$_2$)—; R$_1$ is the radical

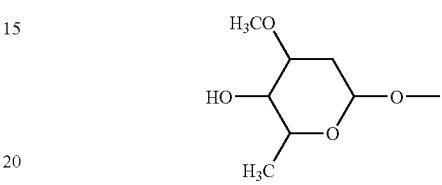

R$_2$ is cyclohexyl; and the bond between atoms 22 and 23 represents a single bond. Selamectin is known e.g. from: ECTOPARASITE ACTIVITY OF SELAMECTIN; A novel endectocide for dogs and cats. A Pfizer Symposium, held in conjunction with The 17th international Conference of the World Association for the Advancement of Veterinary Parasitology, 19 Aug. 1999. Copenhagen, Denmark.

5) Emamectin is (4"-R)-5-O-demethyl-4"-deoxy-4"-(methylamino)avermectin A1a and (4"-R)-5-O-demethyl-25-de(1-methylpropyl)-4"-deoxy-4"-(methylamino)-25-(1-methylethyl)avermectin A1a (9:1), wherein X is —C(H)(OH)—; Y is =C(H)—; R$_1$ is

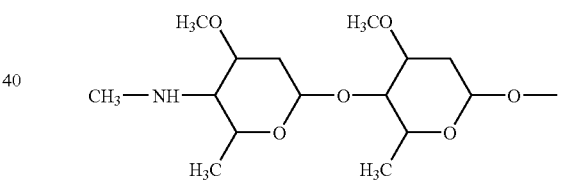

R$_2$ is —CH(CH$_3$)—CH$_3$, or —CH(CH$_3$)—C$_2$H$_5$, and the bond between atoms 22 and 23 represents a double bond. Emamectin is known from U.S. Pat. No. 4,874,749.

6) Eprinomectin is (4"-R)-4"-epi-(acetylamino)-4"-deoxyavermectin B1, wherein X is —C(H)(OH)—; Y is =C(H)—; R$_1$ is the radical

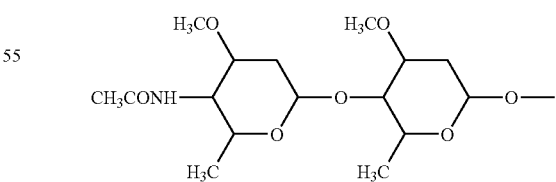

R$_2$ is —CH(CH$_3$)—CH$_3$, or —CH(CH$_3$)—C$_2$H$_5$, and the bond between atoms 22 and 23 represents a double bond. Eprinomectin is known from U.S. Pat. No. 4,427,663.

7) Milbemectin is (6R,25R)-5-O-demethyl-28-deoxy-6,28-epoxy-25-methylmilbemycin, wherein X is —C(H)(OH)—; Y is —C(H$_2$)—; R$_1$ is hydrogen; R$_2$ is —CH$_3$, or —$C_2H_5$; and the bond between atoms 22 and 23 represents a single bond. Milbemectin is known from U.S. Pat. No. 3,950,360.

8) Abamectin is Avermectin B1 which is also named 5-O-demethylayermectin A1a and 5-O-demethyl-25-de(1-methylpropyl)-25-(1-methylethyl)avermectin A1a (4:1), wherein X is —C(H)(OH)—; Y is =C(H)—; $R_1$ is the radical

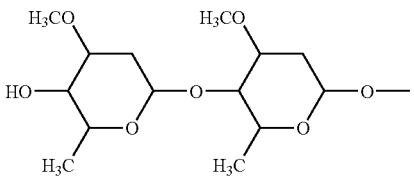

$R_2$ is —CH($CH_3$)—$CH_3$, or —CH($CH_3$)—$C_2H_5$; and the bond between atoms 22 and 23 represents a double bond. Abamectin is known from U.S. Pat. No. 4,310,519.

9) Milbemycin oxim is milbemycin A4 5-oxime; milbemycin A3 5-oxime, wherein X is —C(H)(OH)—; Y is —C($H_2$)—; $R_1$ is hydrogen; $R_2$ is —CH($CH_3$)—$CH_3$, or —CH($CH_3$)—$C_2H_5$, and the bond between atoms 22 and 23 represents a single bond. Milbemycin oxim is known from U.S. Pat. No. 4,547,520.

10) The compound of the formula A wherein X is —C(H)(OH)—; Y is —C($H_2$)—; $R_1$ is the radical

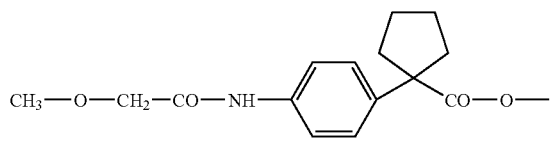

$R_2$ is —$CH_3$ or $C_2H_5$, and the bond between atoms 22 and 23 represents a single bond. This compound is known from WO 01/83500.

11) Nemadectin is antibiotic S-541A; also named [6R,23S,25S, (E)]-5-O-Demethyl-28-deoxy-25-(1,3-dimethyl-1-butenyl)-6,28-epoxy-23-hydroxymilbemycin B; wherein X is =CH—OH; Y is —C($H_2$)—; $R_1$ is hydrogen; $R_2$ is —C($CH_3$)=CH—CH($CH_3$)$_2$, and the bond between atoms 22 and 23 represents a single bond. Nemadectin is known from U.S. Pat. No. 4,869,901.

The compounds specifically mentioned under items 1-11 hereinbefore are preferred embodiments of the present invention and can be used either alone or in combination with another endo-parasiticide, ecto-parasiticide or endecticide.

Especially preferred combination partners are Ivermectin, Abamectin and Moxidectin.

The anthelmintic compositions according to the invention generally comprise 0.1 to 99% by weight, in particular 0.1 to 95% by weight, of active ingredient of the formula I or mixtures thereof, and 99.9 to 1% by weight, in particular 99.8 to 5% by weight, of a solid or liquid additive, including 0 to 25% by weight, in particular 0.1 to 25% by weight, of a surfactant.

The compositions according to the invention can be applied topically, perorally, parenterally or subcutaneously to the animals to be treated, the compositions being present in the form of solutions, emulsions, suspensions (drenches), powders, tablets, boluses, capsules and as pour-on formulations.

The pour-on or spot-on method consists in applying the compound of the formula I to a locally restricted part of the skin or fur, advantageously on the neck or back of the animal. This is carried out, e.g., by applying a spot or dash of the pour-on or spot-on formulation to a relatively small area of the fur, from where the active substance spreads out virtually unaided over wide regions of the fur because of the spreading components of the formulation and supported by the movements of the animal.

It is advantageous for pour-on or spot-on formulations to comprise carriers which promote speedy distribution on the surface of the skin or in the fur of the host animal and which are generally described as spreading oils. Suitable carriers are, e.g., oily solutions; alcoholic and isopropanolic solutions, for example solutions of 2-octyldodecanol or oleyl alcohol; solutions in esters of monocarboxylic acids, such as isopropyl myristate, isopropyl palmitate, lauric acid oxal ester, oleyl oleate, decyl oleate, hexyl laurate, capric acid esters of saturated fatty alcohols with a chain length of $C_{12}$-$C_{18}$; solutions of esters of dicarboxylic acids, such as dibutyl phthalate, diisopropyl isophthalate, diisopropyl adipate or di(n-butyl) adipate, or also solutions of esters of aliphatic acids, e.g. glycols. It can be advantageous if a dispersant known from the pharmaceutical or cosmetics industry is additionally present. Examples are 2-pyrrolidone, 2-(N-alkyl) pyrrolidone, acetone, polyethylene glycol and ethers and esters thereof, propylene glycol or synthetic triglycerides.

The oily solutions include, e.g., vegetable oils, such as olive oil, groundnut oil, sesame oil, pine oil, linseed oil or castor oil. The vegetable oils can also be present in epoxidized form. Paraffin oils and silicone oils can also be used.

In general, a pour-on or spot-on formulation comprises 1 to 20% by weight of a compound of the formula I, 0.1 to 50% by weight of dispersant and 45 to 98.9% by weight of solvent.

The pour-on or spot-on method can be used particularly advantageously with gregarious animals, such as cattle, horses, sheep or pigs, where it is difficult or time-consuming to treat all the animals orally or via injection. Because of its simplicity, this method can naturally also be used with all other animals, including individual domestic animals or pets, and is very popular with animal owners because it can often be implemented without the expert assistance of a veterinary surgeon.

While concentrated compositions are more preferred as commercially available products, the end user generally uses dilute compositions.

Such compositions can comprise yet further additives, such as stabilizers, antifoaming agents, viscosity regulators, binders, deposit builders and other active ingredients to obtain specific effects.

Such anthelmintic compositions used by the end user likewise form part of the present invention.

In each of the methods according to the invention for controlling pests or of the pesticides according to the invention, the active ingredients of the formula I can be used in all their steric configurations or mixtures thereof.

The invention also includes a method for the prophylactic protection of warm-blooded animals, in particular of productive livestock, domestic animals and pets, against parasitic helminths, which comprises applying the active ingredients of the formula I or the active ingredient formulations prepared therefrom as a feed additive or drinking water additive or also in the solid or liquid form, orally, by injection or parenterally, to the animals. The invention also includes the compounds of the formula I according to the invention for use in one of the methods mentioned.

The following examples serve merely to illustrate the invention, without limiting it, the term "active ingredient" representing a substance listed in Table 1.

Preferred formulations are in particular composed in the following way:

(%=percent by weight)

FORMULATION EXAMPLES

| 1. Granules | | |
|---|---|---|
| | a) | b) |
| Active ingredient | 5% | 10% |
| Kaolin | 94% | — |
| Highly dispersed silica | 1% | — |
| Attapulgite | — | 90% |

The active ingredient is dissolved in methylene chloride and sprayed onto the carrier, and the solvent is subsequently evaporated under reduced pressure. Such granules can be added to the animal feed.

| 2. Granules | |
|---|---|
| Active ingredient | 3% |
| Polyethylene glycol (MW 200) | 3% |
| Kaolin | 94% |

(MW = molecular weight)

The finely milled active ingredient is applied evenly in a mixer to the kaolin, which has been moistened with polyethylene glycol. In this way, dust-free coated granules are obtained.

| 3. Tablets or Boluses | | |
|---|---|---|
| I | Active ingredient | 33.00% |
| | Methylcellulose | 0.80% |
| | Highly dispersed silica | 0.80% |
| | Maize starch | 8.40% |
| II | Cryst. lactose | 22.50% |
| | Maize starch | 17.00% |
| | Microcryst. cellulose | 16.50% |
| | Magnesium stearate | 1.00% |

I Methylcellulose is stirred into water. After the material has swollen, silica is stirred in and the mixture is homogeneously suspended. Active ingredient and maize starch are mixed. The aqueous suspension is incorporated in this mixture and kneaded to a dough. The substance thus obtained is granulated through a 12 M sieve and dried.

II All 4 auxiliaries are intimately mixed.

III The premixes obtained according to 1 and 11 are mixed and pressed to give tablets or boluses.

| 4. Injectables | |
|---|---|
| A. Oily vehicle (slow release) | |
| 1. Active ingredient | 0.1-1.0 g |
| Groundnut oil | ad 100 ml |

| 4. Injectables | |
|---|---|
| 2. Active ingredient | 0.1-1.0 g |
| Sesame oil | ad 100 ml |

Preparation: The active ingredient is dissolved in a portion of the oil with stirring and, if desired, gentle heating, made up to the required volume after cooling and sterilely filtered through a suitable membrane filter with a size of 0.22 μm.

| B. Water-miscible solvent (medium release rate) | |
|---|---|
| 1. Active ingredient | 0.1-1.0 g |
| 4-Hydroxymethyl-1,3-dioxolane (glycerol formal) | 40 g |
| 1,2-Propanediol | ad 100 ml |
| 2. Active ingredient | 0.1-1.0 g |
| Glycerol dimethyl acetal | 40 g |
| 1,2-Propanediol | ad 100 ml |

Preparation: The active ingredient is dissolved in a portion of the solvent with stirring, made up to the required volume and sterilely filtered through a suitable membrane filter with a size of 0.22 μm.

| C. Aqueous solubilisate (rapid release) | |
|---|---|
| 1. Active ingredient | 0.1-1.0 g |
| Polyethoxylated castor oil (40 ethylene oxide units) | 10 g |
| 1,2-Propanediol | 20 g |
| Benzyl alcohol | 1 g |
| Water for injections | ad 100 ml |
| 2. Active ingredient | 0.1-1.0 g |
| Polyethoxylated sorbitan monooleate (20 ethylene oxide units) | 8 g |
| 4-Hydroxymethyl-1,3-dioxolane (glycerol formal) | 20 g |
| Benzyl alcohol | 1 g |
| Water for injections | ad 100 ml |

Preparation: The active ingredient is dissolved in a the solvents and the surfactant and made up to the required volume with water. Sterile filtration is carried out through a suitable membrane filter with a pore diameter of 0.22 μm.

| 5. Pour-on | |
|---|---|
| A. | |
| Active ingredient | 5 g |
| Isopropyl myristate | 10 g |
| Isopropanol | ad 100 ml |
| B. | |
| Active ingredient | 2 g |
| Hexyl laurate | 5 g |
| Triglycerides of medium chain length | 15 g |
| Ethanol | ad 100 ml |
| C. | |
| Active ingredient | 2 g |
| Oleyl oleate | 5 g |
| N-Methylpyrrolidone | 40 g |
| Isopropanol | ad 100 ml |

The aqueous systems can preferably also be used for oral and/or intraruminal administration.

The compositions can also comprise further additives, such as stabilizers, e.g. epoxidized or nonepoxidized vegetable oils (epoxidized coconut oil, rapeseed oil or soybean oil), anti-foaming agents, e.g. silicone oil, preservatives, viscosity regulators, binders, deposit builders and fertilizers or other active ingredients to obtain specific effects.

Further biologically active substances or additives which are neutral towards the compounds of the formula I and have no adverse effect on the host animal to be treated, and mineral salts or vitamins, can also be added to the compositions described.

The following examples serve to clarify the invention. They do not limit the invention. The symbol 'h' denotes hour.

PREPARATION EXAMPLES

Example 1

4-[2-cyano-2-(4-trifluoromethoxybenzoylamino)-1-propoxy]-3-trifluoromethylbenzamide

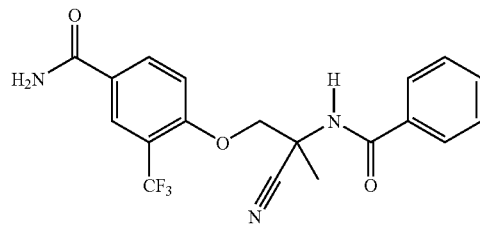

a) In 30 ml of tetrahydrofuran 1.13 g of 4-fluoro-3-trifluoromethylbenzonitrile and 1.87 g of (2-methyl-2-hydroxymethyl-[1,3]dioxolan are diluted and cooled to 0° C. Then a cold solution of 0.73 g potassium t-butoxide in tetrahydrofuran is added dropwise. After stirring for 30 min at 0° C. the reaction mixture is diluted with 50 ml of ethyl acetate and washed twice with a saturated solution of ammonium chloride, water and brine. The organic phase is finally dried over magnesium sulfate, filtered and concentrated under vacuum. The residue is then stirred with hexane, filtered and dried to yield amorphous crystals of 4-(2-methyl-[1,3]dioxolan-2-ylmethoxy])-3-trifluoromethylbenzonitrile.

b) In 30 ml of ethylene glycol and 25 ml of an 8N aqueous solution of potassium hydroxide 862 mg of 4-(2-methyl-[1,3]dioxolan-2-ylmethoxy)-3-trifluoromethylbenzonitrile are dissolved and stirred for 22 h at 65° C. The yellow mixture is then cooled to 0° C., neutralized with an aqueous solution of 2N hydrochloric acid, diluted with 50 ml of ethyl acetate and washed with water and brine. The organic phases are dried over magnesium sulfate, filtered and evaporated to afford crude 4-(2-methyl-[1,3]dioxolan-2-ylmethoxy])-3-trifluoromethylbenzamide.

c) In 15 ml of acetone and 7.5 ml of an aqueous solution of 2N hydrochloric acid 916 mg of crude 4-(2-methyl-[1,3]dioxolan-2-ylmethoxy])-3-trifluoromethylbenzamide are dissolved, stirred at reflux temperature for 24 h, then cooled to room temperature and evaporated. The residue is diluted in 30 ml ethyl acetate and washed with a saturated solution of sodium carbonate and water. After separation the organic phase is dried over magnesium sulfate, filtered and evaporated to yield 4-(2-oxopropoxy)-3-trifluoromethylbenzamide.

d) In 5 ml of ethanol 260 mg of 4-(2-oxopropoxy)-3-trifluoromethylbenzamide is dissolved, then 73.5 mg of sodium cyanide, 80.2 mg of ammonium chloride and 15 ml of an aqueous solution of 25% ammonia is added and the mixture stirred for 24 h at room temperature. After evaporation of the solvent the residue is re-dissolved and stirred in ethyl acetate, dried with magnesium sulfate, filtered and evaporated to afford 4-(2-amino-2-cyanopropoxy)-3-trifluoromethylbenzamide.

e) In 4 ml of dichloromethane 171 mg of 4-(2-amino-2-cyanopropoxy)-3-trifluoromethylbenzamide are dissolved, then 108 mg of ethyldiisopropylamine and 160 mg of 4-(trifluoro-methoxy)-benzoylchloride are added. The mixture is stirred overnight at room temperature, then diluted with 30 ml of dichloromethane and successively washed with a saturated aqueous solution of sodium bicarbonate, water, an aqueous solution of 1N hydrochloric acid and finally brine. The organic phases are dried over magnesium sulfate, filtered and evaporated. The crude residue is purified by flash chromatography to yield the title compound.

The substances mentioned in the following table can also be prepared analogously to the procedure described above. The melting point values are given in ° C.

TABLE 1

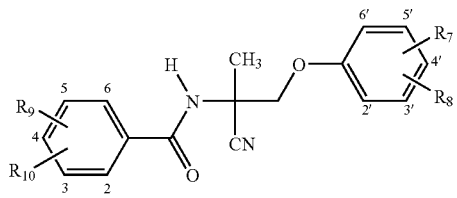

| No. | $R_7$ | $R_8$ | $R_9$ | $R_{10}$ | Phys. data |
|---|---|---|---|---|---|
| 1.1 | 4'-COOH | H | H | H | |
| 1.2 | 4'-COOH | H | 4-F | H | |
| 1.3 | 4'-COOH | H | 4-Cl | H | |
| 1.4 | 4'-COOH | H | 4-CN | H | |
| 1.5 | 4'-COOH | H | 4-$CH_3$ | H | |
| 1.6 | 4'-COOH | H | 4-$CF_3$ | H | |
| 1.7 | 4'-COOH | H | 4-$OCF_3$ | H | |
| 1.8 | 4'-COOH | H | 4-$SCF_3$ | H | |
| 1.9 | 4'-COOH | H | 4-$S(O)CF_3$ | H | |
| 1.10 | 4'-COOH | H | 4-$S(O)_2CF_3$ | H | |
| 1.11 | 4'-COOH | H | 2-F | H | |
| 1.12 | 4'-COOH | H | 2-Cl | H | |
| 1.13 | 4'-COOH | H | 2-CN | H | |
| 1.14 | 4'-COOH | H | 2-$CH_3$ | H | |
| 1.15 | 4'-COOH | H | 2-$CF_3$ | H | |
| 1.16 | 4'-COOH | H | 2-$OCF_3$ | H | |

TABLE 1-continued

| No. | R$_7$ | R$_8$ | R$_9$ | R$_{10}$ | Phys. data |
|---|---|---|---|---|---|
| 1.17 | 4'-COOH | H | 2-SCF$_3$ | H | |
| 1.18 | 4'-COOH | H | 2-S(O)CF$_3$ | H | |
| 1.19 | 4'-COOH | H | 2-S(O)$_2$CF$_3$ | H | |
| 1.20 | 4'-COOH | H | H | 4-NH$_2$ | |
| 1.21 | 4'-COOH | H | H | 4-COOH | |
| 1.22 | 4'-COOH | H | H | 4-CONH$_2$ | |
| 1.23 | 4'-COOH | H | H | 4-CSNH$_2$ | |
| 1.24 | 4'-COOH | H | H | 4-NHCONH$_2$ | |
| 1.25 | 4'-COOH | H | H | 4-NHCSNH$_2$ | |
| 1.26 | 4'-COOH | H | H | 4-OCSNH$_2$ | |
| 1.27 | 4'-COOH | H | H | 3-OC(F$_2$)O-4 | |
| 1.28 | 4'-COOH | H | H | SC(F$_2$)S-4 | |
| 1.29 | 4'-COOH | H | 2-F | 4-NH$_2$ | |
| 1.30 | 4'-COOH | H | 2-Cl | 4-COOH | |
| 1.31 | 4'-COOH | H | 2-CN | 4-CONH$_2$ | |
| 1.32 | 4'-COOH | H | 2-CH$_3$ | 4-CSNH$_2$ | |
| 1.33 | 4'-COOH | H | 2-CF$_3$ | 4-NHCONH$_2$ | |
| 1.34 | 4'-COOH | H | 2-OCF$_3$ | 4-NHCSNH$_2$ | |
| 1.35 | 4'-COOH | H | 2-SCF$_3$ | 4-OCSNH$_2$ | |
| 1.36 | 4'-COOH | 2'-CN | H | H | |
| 1.37 | 4'-COOH | 2'-CN | 4-F | H | |
| 1.38 | 4'-COOH | 2'-CN | 4-Cl | H | |
| 1.39 | 4'-COOH | 2'-CN | 4-CN | H | |
| 1.40 | 4'-COOH | 2'-CN | 4-CH$_3$ | H | |
| 1.41 | 4'-COOH | 2'-CN | 4-CF$_3$ | H | |
| 1.42 | 4'-COOH | 2'-CN | 4-OCF$_3$ | H | |
| 1.43 | 4'-COOH | 2'-CN | 4-SCF$_3$ | H | |
| 1.44 | 4'-COOH | 2'-CN | 4-S(O)CF$_3$ | H | |
| 1.45 | 4'-COOH | 2'-CN | 4-S(O)$_2$CF$_3$ | H | |
| 1.46 | 4'-COOH | 2'-CN | 2-F | H | |
| 1.47 | 4'-COOH | 2'-CN | 2-Cl | H | |
| 1.48 | 4'-COOH | 2'-CN | 2-CN | H | |
| 1.49 | 4'-COOH | 2'-CN | 2-CH$_3$ | H | |
| 1.50 | 4'-COOH | 2'-CN | 2-CF$_3$ | H | |
| 1.51 | 4'-COOH | 2'-CN | 2-OCF$_3$ | H | |
| 1.52 | 4'-COOH | 2'-CN | 2-SCF$_3$ | H | |
| 1.53 | 4'-COOH | 2'-CN | 2-S(O)CF$_3$ | H | |
| 1.54 | 4'-COOH | 2'-CN | 2-S(O)$_2$CF$_3$ | H | |
| 1.55 | 4'-COOH | 2'-CN | H | 4-NH$_2$ | |
| 1.56 | 4'-COOH | 2'-CN | H | 4-COOH | |
| 1.57 | 4'-COOH | 2'-CN | H | 4-CONH$_2$ | |
| 1.58 | 4'-COOH | 2'-CN | H | 4-CSNH$_2$ | |
| 1.59 | 4'-COOH | 2'-CN | H | 4-NHCONH$_2$ | |
| 1.60 | 4'-COOH | 2'-CN | H | 4-NHCSNH$_2$ | |
| 1.61 | 4'-COOH | 2'-CN | H | 4-OCSNH$_2$ | |
| 1.62 | 4'-COOH | 2'-CN | H | 3-OC(F$_2$)O-4 | |
| 1.63 | 4'-COOH | 2'-CN | H | 3-SC(F$_2$)S-4 | |
| 1.64 | 4'-COOH | 2'-CN | 2-F | 4-NH$_2$ | |
| 1.65 | 4'-COOH | 2'-CN | 2-Cl | 4-COOH | |
| 1.66 | 4'-COOH | 2'-CN | 2-CN | 4-CONH$_2$ | |
| 1.67 | 4'-COOH | 2'-CN | 2-CH$_3$ | 4-CSNH$_2$ | |
| 1.68 | 4'-COOH | 2'-CN | 2-CF$_3$ | 4-NHCONH$_2$ | |
| 1.69 | 4'-COOH | 2'-CN | 2-OCF$_3$ | 4-NHCSNH$_2$ | |
| 1.70 | 4'-COOH | 2'-CN | 2-SCF$_3$ | 4-OCSNH$_2$ | |
| 1.71 | 4'-COOH | 2'-CH$_3$ | H | H | |
| 1.72 | 4'-COOH | 2'-CH$_3$ | 4-F | H | |
| 1.73 | 4'-COOH | 2'-CH$_3$ | 4-Cl | H | |
| 1.74 | 4'-COOH | 2'-CH$_3$ | 4-CN | H | |
| 1.75 | 4'-COOH | 2'-CH$_3$ | 4-CH$_3$ | H | |
| 1.76 | 4'-COOH | 2'-CH$_3$ | 4-CF$_3$ | H | |
| 1.77 | 4'-COOH | 2'-CH$_3$ | 4-OCF$_3$ | H | |
| 1.78 | 4'-COOH | 2'-CH$_3$ | 4-SCF$_3$ | H | |
| 1.79 | 4'-COOH | 2'-CH$_3$ | 4-S(O)CF$_3$ | H | |
| 1.80 | 4'-COOH | 2'-CH$_3$ | 4-S(O)$_2$CF$_3$ | H | |
| 1.81 | 4'-COOH | 2'-CH$_3$ | 2-F | H | |
| 1.82 | 4'-COOH | 2'-CH$_3$ | 2-Cl | H | |

TABLE 1-continued

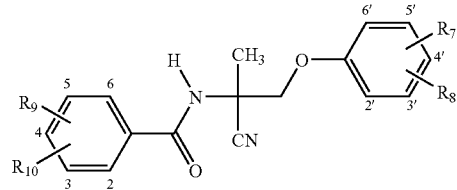

| No. | R₇ | R₈ | R₉ | R₁₀ | Phys. data |
|---|---|---|---|---|---|
| 1.83 | 4'-COOH | 2'-CH₃ | 2-CN | H | |
| 1.84 | 4'-COOH | 2'-CH₃ | 2-CH₃ | H | |
| 1.85 | 4'-COOH | 2'-CH₃ | 2-CF₃ | H | |
| 1.86 | 4'-COOH | 2'-CH₃ | 2-OCF₃ | H | |
| 1.87 | 4'-COOH | 2'-CH₃ | 2-SCF₃ | H | |
| 1.88 | 4'-COOH | 2'-CH₃ | 2-S(O)CF₃ | H | |
| 1.89 | 4'-COOH | 2'-CH₃ | 2-S(O)₂CF₃ | H | |
| 1.90 | 4'-COOH | 2'-CH₃ | H | 4-NH₂ | |
| 1.91 | 4'-COOH | 2'-CH₃ | H | 4-COOH | |
| 1.92 | 4'-COOH | 2'-CH₃ | H | 4-CONH₂ | |
| 1.93 | 4'-COOH | 2'-CH₃ | H | 4-CSNH₂ | |
| 1.94 | 4'-COOH | 2'-CH₃ | H | 4-NHCONH₂ | |
| 1.95 | 4'-COOH | 2'-CH₃ | H | 4-NHCSNH₂ | |
| 1.96 | 4'-COOH | 2'-CH₃ | H | 4-OCSNH₂ | |
| 1.97 | 4'-COOH | 2'-CH₃ | H | 3-OC(F₂)O-4 | |
| 1.98 | 4'-COOH | 2'-CH₃ | H | 3-SC(F₂)S-4 | |
| 1.99 | 4'-COOH | 2'-CH₃ | 2-F | 4-NH₂ | |
| 1.100 | 4'-COOH | 2'-CH₃ | 2-Cl | 4-COOH | |
| 1.101 | 4'-COOH | 2'-CH₃ | 2-CN | 4-CONH₂ | |
| 1.102 | 4'-COOH | 2'-CH₃ | 2-CH₃ | 4-CSNH₂ | |
| 1.103 | 4'-COOH | 2'-CH₃ | 2-CF₃ | 4-NHCONH₂ | |
| 1.104 | 4'-COOH | 2'-CH₃ | 2-OCF₃ | 4-NHCSNH₂ | |
| 1.105 | 4'-COOH | 2'-CH₃ | 2-SCF₃ | 4-OCSNH₂ | |
| 1.106 | 4'-COOH | 2'-CF₃ | H | H | |
| 1.107 | 4'-COOH | 2'-CF₃ | 4-F | H | |
| 1.108 | 4'-COOH | 2'-CF₃ | 4-Cl | H | |
| 1.109 | 4'-COOH | 2'-CF₃ | 4-CN | H | |
| 1.110 | 4'-COOH | 2'-CF₃ | 4-CH₃ | H | |
| 1.111 | 4'-COOH | 2'-CF₃ | 4-CF₃ | H | |
| 1.112 | 4'-COOH | 2'-CF₃ | 4-OCF₃ | H | m.p. 110-4° |
| 1.113 | 4'-COOH | 2'-CF₃ | 4-SCF₃ | H | |
| 1.114 | 4'-COOH | 2'-CF₃ | 4-S(O)CF₃ | H | |
| 1.115 | 4'-COOH | 2'-CF₃ | 4-S(O)₂CF₃ | H | |
| 1.116 | 4'-COOH | 2'-CF₃ | 2-F | H | |
| 1.117 | 4'-COOH | 2'-CF₃ | 2-Cl | H | |
| 1.118 | 4'-COOH | 2'-CF₃ | 2-CN | H | |
| 1.119 | 4'-COOH | 2'-CF₃ | 2-CH₃ | H | |
| 1.120 | 4'-COOH | 2'-CF₃ | 2-CF₃ | H | |
| 1.121 | 4'-COOH | 2'-CF₃ | 2-OCF₃ | H | |
| 1.122 | 4'-COOH | 2'-CF₃ | 2-SCF₃ | H | |
| 1.123 | 4'-COOH | 2'-CF₃ | 2-S(O)CF₃ | H | |
| 1.124 | 4'-COOH | 2'-CF₃ | 2-S(O)₂CF₃ | H | |
| 1.125 | 4'-COOH | 2'-CF₃ | H | 4-NH₂ | |
| 1.126 | 4'-COOH | 2'-CF₃ | H | 4-COOH | |
| 1.127 | 4'-COOH | 2'-CF₃ | H | 4-CONH₂ | |
| 1.128 | 4'-COOH | 2'-CF₃ | H | 4-CSNH₂ | |
| 1.129 | 4'-COOH | 2'-CF₃ | H | 4-NHCONH₂ | |
| 1.130 | 4'-COOH | 2'-CF₃ | H | 4-NHCSNH₂ | |
| 1.131 | 4'-COOH | 2'-CF₃ | H | 4-OCSNH₂ | |
| 1.132 | 4'-COOH | 2'-CF₃ | H | 3-OC(F₂)O-4 | |
| 1.133 | 4'-COOH | 2'-CF₃ | H | 3-SC(F₂)S-4 | |
| 1.134 | 4'-COOH | 2'-CF₃ | 2-F | 4-NH₂ | |
| 1.135 | 4'-COOH | 2'-CF₃ | 2-Cl | 4-COOH | |
| 1.136 | 4'-COOH | 2'-CF₃ | 2-CN | 4-CONH₂ | |
| 1.137 | 4'-COOH | 2'-CF₃ | 2-CH₃ | 4-CSNH₂ | |
| 1.138 | 4'-COOH | 2'-CF₃ | 2-CF₃ | 4-NHCONH₂ | |
| 1.139 | 4'-COOH | 2'-CF₃ | 2-OCF₃ | 4-NHCSNH₂ | |
| 1.140 | 4'-COOH | 2'-CF₃ | 2-SCF₃ | 4-OCSNH₂ | |
| 1.141 | 4'-COOH | 2'-OCF₃ | H | H | |
| 1.142 | 4'-COOH | 2'-OCF₃ | 4-F | H | |
| 1.143 | 4'-COOH | 2'-OCF₃ | 4-Cl | H | |
| 1.144 | 4'-COOH | 2'-OCF₃ | 4-CN | H | |
| 1.145 | 4'-COOH | 2'-OCF₃ | 4-CH₃ | H | |
| 1.146 | 4'-COOH | 2'-OCF₃ | 4-CF₃ | H | |
| 1.147 | 4'-COOH | 2'-OCF₃ | 4-OCF₃ | H | |
| 1.148 | 4'-COOH | 2'-OCF₃ | 4-SCF₃ | H | |

TABLE 1-continued

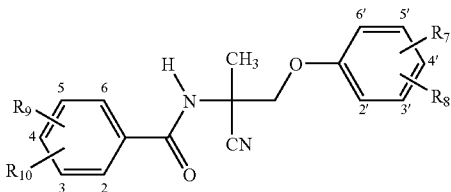

| No. | R$_7$ | R$_8$ | R$_9$ | R$_{10}$ | Phys. data |
|---|---|---|---|---|---|
| 1.149 | 4'-COOH | 2'-OCF$_3$ | 4-S(O)CF$_3$ | H | |
| 1.150 | 4'-COOH | 2'-OCF$_3$ | 4-S(O)$_2$CF$_3$ | H | |
| 1.151 | 4'-COOH | 2'-OCF$_3$ | 2-F | H | |
| 1.152 | 4'-COOH | 2'-OCF$_3$ | 2-Cl | H | |
| 1.153 | 4'-COOH | 2'-OCF$_3$ | 2-CN | H | |
| 1.154 | 4'-COOH | 2'-OCF$_3$ | 2-CH$_3$ | H | |
| 1.155 | 4'-COOH | 2'-OCF$_3$ | 2-CF$_3$ | H | |
| 1.156 | 4'-COOH | 2'-OCF$_3$ | 2-OCF$_3$ | H | |
| 1.157 | 4'-COOH | 2'-OCF$_3$ | 2-SCF$_3$ | H | |
| 1.158 | 4'-COOH | 2'-OCF$_3$ | 2-S(O)CF$_3$ | H | |
| 1.159 | 4'-COOH | 2'-OCF$_3$ | 2-S(O)$_2$CF$_3$ | H | |
| 1.160 | 4'-COOH | 2'-OCF$_3$ | H | 4-NH$_2$ | |
| 1.161 | 4'-COOH | 2'-OCF$_3$ | H | 4-COOH | |
| 1.162 | 4'-COOH | 2'-OCF$_3$ | H | 4-CONH$_2$ | |
| 1.163 | 4'-COOH | 2'-OCF$_3$ | H | 4-CSNH$_2$ | |
| 1.164 | 4'-COOH | 2'-OCF$_3$ | H | 4-NHCONH$_2$ | |
| 1.165 | 4'-COOH | 2'-OCF$_3$ | H | 4-NHCSNH$_2$ | |
| 1.166 | 4'-COOH | 2'-OCF$_3$ | H | 4-OCSNH$_2$ | |
| 1.167 | 4'-COOH | 2'-OCF$_3$ | H | 3-OC(F$_2$)O-4 | |
| 1.168 | 4'-COOH | 2'-OCF$_3$ | H | 3-SC(F$_2$)S-4 | |
| 1.169 | 4'-COOH | 2'-OCF$_3$ | 2-F | 4-NH$_2$ | |
| 1.170 | 4'-COOH | 2'-OCF$_3$ | 2-Cl | 4-COOH | |
| 1.171 | 4'-COOH | 2'-OCF$_3$ | 2-CN | 4-CONH$_2$ | |
| 1.172 | 4'-COOH | 2'-OCF$_3$ | 2-CH$_3$ | 4-CSNH$_2$ | |
| 1.173 | 4'-COOH | 2'-OCF$_3$ | 2-CF$_3$ | 4-NHCONH$_2$ | |
| 1.174 | 4'-COOH | 2'-OCF$_3$ | 2-OCF$_3$ | 4-NHCSNH$_2$ | |
| 1.175 | 4'-COOH | 2'-OCF$_3$ | 2-SCF$_3$ | 4-OCSNH$_2$ | |
| 1.176 | 4'-COOH | 2'-C$_6$H$_5$ | H | H | |
| 1.177 | 4'-COOH | 2'-C$_6$H$_5$ | 4-F | H | |
| 1.178 | 4'-COOH | 2'-C$_6$H$_5$ | 4-Cl | H | |
| 1.179 | 4'-COOH | 2'-C$_6$H$_5$ | 4-CN | H | |
| 1.180 | 4'-COOH | 2'-C$_6$H$_5$ | 4-CH$_3$ | H | |
| 1.181 | 4'-COOH | 2'-C$_6$H$_5$ | 4-CF$_3$ | H | |
| 1.182 | 4'-COOH | 2'-C$_6$H$_5$ | 4-OCF$_3$ | H | |
| 1.183 | 4'-COOH | 2'-C$_6$H$_5$ | 4-SCF$_3$ | H | |
| 1.184 | 4'-COOH | 2'-C$_6$H$_5$ | 4-S(O)CF$_3$ | H | |
| 1.185 | 4'-COOH | 2'-C$_6$H$_5$ | 4-S(O)$_2$CF$_3$ | H | |
| 1.186 | 4'-COOH | 2'-C$_6$H$_5$ | 2-F | H | |
| 1.187 | 4'-COOH | 2'-C$_6$H$_5$ | 2-Cl | H | |
| 1.188 | 4'-COOH | 2'-C$_6$H$_5$ | 2-CN | H | |
| 1.189 | 4'-COOH | 2'-C$_6$H$_5$ | 2-CH$_3$ | H | |
| 1.190 | 4'-COOH | 2'-C$_6$H$_5$ | 2-CF$_3$ | H | |
| 1.191 | 4'-COOH | 2'-C$_6$H$_5$ | 2-OCF$_3$ | H | |
| 1.192 | 4'-COOH | 2'-C$_6$H$_5$ | 2-SCF$_3$ | H | |
| 1.193 | 4'-COOH | 2'-C$_6$H$_5$ | 2-S(O)CF$_3$ | H | |
| 1.194 | 4'-COOH | 2'-C$_6$H$_5$ | 2-S(O)$_2$CF$_3$ | H | |
| 1.195 | 4'-COOH | 2'-C$_6$H$_5$ | H | 4-NH$_2$ | |
| 1.196 | 4'-COOH | 2'-C$_6$H$_5$ | H | 4-COOH | |
| 1.197 | 4'-COOH | 2'-C$_6$H$_5$ | H | 4-CONH$_2$ | |
| 1.198 | 4'-COOH | 2'-C$_6$H$_5$ | H | 4-CSNH$_2$ | |
| 1.199 | 4'-COOH | 2'-C$_6$H$_5$ | H | 4-NHCONH$_2$ | |
| 1.200 | 4'-COOH | 2'-C$_6$H$_5$ | H | 4-NHCSNH$_2$ | |
| 1.201 | 4'-COOH | 2'-C$_6$H$_5$ | H | 4-OCSNH$_2$ | |
| 1.202 | 4'-COOH | 2'-C$_6$H$_5$ | H | 3-OC(F$_2$)O-4 | |
| 1.203 | 4'-COOH | 2'-C$_6$H$_5$ | H | 3-SC(F$_2$)S-4 | |
| 1.204 | 4'-COOH | 2'-C$_6$H$_5$ | 2-F | 4-NH$_2$ | |
| 1.205 | 4'-COOH | 2'-C$_6$H$_5$ | 2-Cl | 4-COOH | |
| 1.206 | 4'-COOH | 2'-C$_6$H$_5$ | 2-CN | 4-CONH$_2$ | |
| 1.207 | 4'-COOH | 2'-C$_6$H$_5$ | 2-CH$_3$ | 4-CSNH$_2$ | |
| 1.208 | 4'-COOH | 2'-C$_6$H$_5$ | 2-CF$_3$ | 4-NHCONH$_2$ | |
| 1.209 | 4'-COOH | 2'-C$_6$H$_5$ | 2-OCF$_3$ | 4-NHCSNH$_2$ | |
| 1.210 | 4'-COOH | 2'-C$_6$H$_5$ | 2-SCF$_3$ | 4-OCSNH$_2$ | |
| 1.211 | 4'-COOH | 2'-(C$_6$H$_4$-4-Cl) | H | H | |
| 1.212 | 4'-COOH | 2'-(C$_6$H$_4$-4-Cl) | 4-F | H | |
| 1.213 | 4'-COOH | 2'-(C$_6$H$_4$-4-Cl) | 4-Cl | H | |
| 1.214 | 4'-COOH | 2'-(C$_6$H$_4$-4-Cl) | 4-CN | H | |

TABLE 1-continued

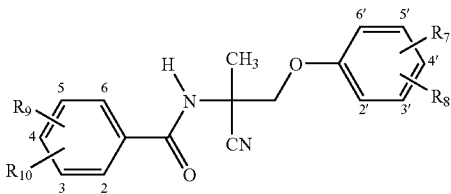

| No. | $R_7$ | $R_8$ | $R_9$ | $R_{10}$ | Phys. data |
|---|---|---|---|---|---|
| 1.215 | 4'-COOH | 2'-($C_6H_4$-4-Cl) | 4-$CH_3$ | H | |
| 1.216 | 4'-COOH | 2'-($C_6H_4$-4-Cl) | 4-$CF_3$ | H | |
| 1.217 | 4'-COOH | 2'-($C_6H_4$-4-Cl) | 4-$OCF_3$ | H | |
| 1.218 | 4'-COOH | 2'-($C_6H_4$-4-Cl) | 4-$SCF_3$ | H | |
| 1.219 | 4'-COOH | 2'-($C_6H_4$-4-Cl) | 4-S(O)$CF_3$ | H | |
| 1.220 | 4'-COOH | 2'-($C_6H_4$-4-Cl) | 4-S(O)$_2CF_3$ | H | |
| 1.221 | 4'-COOH | 2'-($C_6H_4$-4-Cl) | 2-F | H | |
| 1.222 | 4'-COOH | 2'-($C_6H_4$-4-Cl) | 2-Cl | H | |
| 1.223 | 4'-COOH | 2'-($C_6H_4$-4-Cl) | 2-CN | H | |
| 1.224 | 4'-COOH | 2'-($C_6H_4$-4-Cl) | 2-$CH_3$ | H | |
| 1.225 | 4'-COOH | 2'-($C_6H_4$-4-Cl) | 2-$CF_3$ | H | |
| 1.226 | 4'-COOH | 2'-($C_6H_4$-4-Cl) | 2-$OCF_3$ | H | |
| 1.227 | 4'-COOH | 2'-($C_6H_4$-4-Cl) | 2-$SCF_3$ | H | |
| 1.228 | 4'-COOH | 2'-($C_6H_4$-4-Cl) | 2-S(O)$CF_3$ | H | |
| 1.229 | 4'-COOH | 2'-($C_6H_4$-4-Cl) | 2-S(O)$_2CF_3$ | H | |
| 1.230 | 4'-COOH | 2'-($C_6H_4$-4-Cl) | H | 4-$NH_2$ | |
| 1.231 | 4'-COOH | 2'-($C_6H_4$-4-Cl) | H | 4-COOH | |
| 1.232 | 4'-COOH | 2'-($C_6H_4$-4-Cl) | H | 4-$CONH_2$ | |
| 1.233 | 4'-COOH | 2'-($C_6H_4$-4-Cl) | H | 4-$CSNH_2$ | |
| 1.234 | 4'-COOH | 2'-($C_6H_4$-4-Cl) | H | 4-$NHCONH_2$ | |
| 1.235 | 4'-COOH | 2'-($C_6H_4$-4-Cl) | H | 4-$NHCSNH_2$ | |
| 1.236 | 4'-COOH | 2'-($C_6H_4$-4-Cl) | H | 4-$OCSNH_2$ | |
| 1.237 | 4'-COOH | 2'-($C_6H_4$-4-Cl) | H | 3-OC($F_2$)O-4 | |
| 1.238 | 4'-COOH | 2'-($C_6H_4$-4-Cl) | H | 3-SC($F_2$)S-4 | |
| 1.239 | 4'-COOH | 2'-($C_6H_4$-4-Cl) | 2-F | 4-$NH_2$ | |
| 1.240 | 4'-COOH | 2'-($C_6H_4$-4-Cl) | 2-Cl | 4-COOH | |
| 1.241 | 4'-COOH | 2'-($C_6H_4$-4-Cl) | 2-CN | 4-$CONH_2$ | |
| 1.242 | 4'-COOH | 2'-($C_6H_4$-4-Cl) | 2-$CH_3$ | 4-$CSNH_2$ | |
| 1.243 | 4'-COOH | 2'-($C_6H_4$-4-Cl) | 2-$CF_3$ | 4-$NHCONH_2$ | |
| 1.244 | 4'-COOH | 2'-($C_6H_4$-4-Cl) | 2-$OCF_3$ | 4-$NHCSNH_2$ | |
| 1.245 | 4'-COOH | 2'-($C_6H_4$-4-Cl) | 2-$SCF_3$ | 4-$OCSNH_2$ | |
| 1.246 | 4'-COOH | 2'-($C_6H_3$-2,4-$Cl_2$) | H | H | |
| 1.247 | 4'-COOH | 2'-($C_6H_3$-2,4-$Cl_2$) | 4-F | H | |
| 1.248 | 4'-COOH | 2'-($C_6H_3$-2,4-$Cl_2$) | 4-Cl | H | |
| 1.249 | 4'-COOH | 2'-($C_6H_3$-2,4-$Cl_2$) | 4-CN | H | |
| 1.250 | 4'-COOH | 2'-($C_6H_3$-2,4-$Cl_2$) | 4-$CH_3$ | H | |
| 1.251 | 4'-COOH | 2'-($C_6H_3$-2,4-$Cl_2$) | 4-$CF_3$ | H | |
| 1.252 | 4'-COOH | 2'-($C_6H_3$-2,4-$Cl_2$) | 4-$OCF_3$ | H | |
| 1.253 | 4'-COOH | 2'-($C_6H_3$-2,4-$Cl_2$) | 4-$SCF_3$ | H | |
| 1.254 | 4'-COOH | 2'-($C_6H_3$-2,4-$Cl_2$) | 4-S(O)$CF_3$ | H | |
| 1.255 | 4'-COOH | 2'-($C_6H_3$-2,4-$Cl_2$) | 4-S(O)$_2CF_3$ | H | |
| 1.256 | 4'-COOH | 2'-($C_6H_3$-2,4-$Cl_2$) | 2-F | H | |
| 1.257 | 4'-COOH | 2'-($C_6H_3$-2,4-$Cl_2$) | 2-Cl | H | |
| 1.258 | 4'-COOH | 2'-($C_6H_3$-2,4-$Cl_2$) | 2-CN | H | |
| 1.259 | 4'-COOH | 2'-($C_6H_3$-2,4-$Cl_2$) | 2-$CH_3$ | H | |
| 1.260 | 4'-COOH | 2'-($C_6H_3$-2,4-$Cl_2$) | 2-$CF_3$ | H | |
| 1.261 | 4'-COOH | 2'-($C_6H_3$-2,4-$Cl_2$) | 2-$OCF_3$ | H | |
| 1.262 | 4'-COOH | 2'-($C_6H_3$-2,4-$Cl_2$) | 2-$SCF_3$ | H | |
| 1.263 | 4'-COOH | 2'-($C_6H_3$-2,4-$Cl_2$) | 2-S(O)$CF_3$ | H | |
| 1.264 | 4'-COOH | 2'-($C_6H_3$-2,4-$Cl_2$) | 2-S(O)$_2CF_3$ | H | |
| 1.265 | 4'-COOH | 2'-($C_6H_3$-2,4-$Cl_2$) | H | 4-$NH_2$ | |
| 1.266 | 4'-COOH | 2'-($C_6H_3$-2,4-$Cl_2$) | H | 4-COOH | |
| 1.267 | 4'-COOH | 2'-($C_6H_3$-2,4-$Cl_2$) | H | 4-$CONH_2$ | |
| 1.268 | 4'-COOH | 2'-($C_6H_3$-2,4-$Cl_2$) | H | 4-$CSNH_2$ | |
| 1.269 | 4'-COOH | 2'-($C_6H_3$-2,4-$Cl_2$) | H | 4-$NHCONH_2$ | |
| 1.270 | 4'-COOH | 2'-($C_6H_3$-2,4-$Cl_2$) | H | 4-$NHCSNH_2$ | |
| 1.271 | 4'-COOH | 2'-($C_6H_3$-2,4-$Cl_2$) | H | 4-$OCSNH_2$ | |
| 1.272 | 4'-COOH | 2'-($C_6H_3$-2,4-$Cl_2$) | H | 3-OC($F_2$)O-4 | |
| 1.273 | 4'-COOH | 2'-($C_6H_3$-2,4-$Cl_2$) | H | 3-SC($F_2$)S-4 | |
| 1.274 | 4'-COOH | 2'-($C_6H_3$-2,4-$Cl_2$) | 2-F | 4-$NH_2$ | |
| 1.275 | 4'-COOH | 2'-($C_6H_3$-2,4-$Cl_2$) | 2-Cl | 4-COOH | |
| 1.276 | 4'-COOH | 2'-($C_6H_3$-2,4-$Cl_2$) | 2-CN | 4-$CONH_2$ | |
| 1.277 | 4'-COOH | 2'-($C_6H_3$-2,4-$Cl_2$) | 2-$CH_3$ | 4-$CSNH_2$ | |
| 1.278 | 4'-COOH | 2'-($C_6H_3$-2,4-$Cl_2$) | 2-$CF_3$ | 4-$NHCONH_2$ | |
| 1.279 | 4'-COOH | 2'-($C_6H_3$-2,4-$Cl_2$) | 2-$OCF_3$ | 4-$NHCSNH_2$ | |
| 1.280 | 4'-COOH | 2'-($C_6H_3$-2,4-$Cl_2$) | 2-$SCF_3$ | 4-$OCSNH_2$ | |

TABLE 1-continued

| No. | R₇ | R₈ | R₉ | R₁₀ | Phys. data |
|---|---|---|---|---|---|
| 1.281 | 4'-CONH₂ | H | H | H | |
| 1.282 | 4'-CONH₂ | H | 4-F | H | |
| 1.283 | 4'-CONH₂ | H | 4-Cl | H | |
| 1.284 | 4'-CONH₂ | H | 4-CN | H | |
| 1.285 | 4'-CONH₂ | H | 4-CH₃ | H | |
| 1.286 | 4'-CONH₂ | H | 4-CF₃ | H | |
| 1.287 | 4'-CONH₂ | H | 4-OCF₃ | H | |
| 1.288 | 4'-CONH₂ | H | 4-SCF₃ | H | |
| 1.289 | 4'-CONH₂ | H | 4-S(O)CF₃ | H | |
| 1.290 | 4'-CONH₂ | H | 4-S(O)₂CF₃ | H | |
| 1.291 | 4'-CONH₂ | H | 2-F | H | |
| 1.292 | 4'-CONH₂ | H | 2-Cl | H | |
| 1.293 | 4'-CONH₂ | H | 2-CN | H | |
| 1.294 | 4'-CONH₂ | H | 2-CH₃ | H | |
| 1.295 | 4'-CONH₂ | H | 2-CF₃ | H | |
| 1.296 | 4'-CONH₂ | H | 2-OCF₃ | H | |
| 1.297 | 4'-CONH₂ | H | 2-SCF₃ | H | |
| 1.298 | 4'-CONH₂ | H | 2-S(O)CF₃ | H | |
| 1.299 | 4'-CONH₂ | H | 2-S(O)₂CF₃ | H | |
| 1.300 | 4'-CONH₂ | H | H | 4-NH₂ | |
| 1.301 | 4'-CONH₂ | H | H | 4-COOH | |
| 1.302 | 4'-CONH₂ | H | H | 4-CONH₂ | |
| 1.303 | 4'-CONH₂ | H | H | 4-CSNH₂ | |
| 1.304 | 4'-CONH₂ | H | H | 4-NHCONH₂ | |
| 1.305 | 4'-CONH₂ | H | H | 4-NHCSNH₂ | |
| 1.306 | 4'-CONH₂ | H | H | 4-OCSNH₂ | |
| 1.307 | 4'-CONH₂ | H | H | 3-OC(F₂)O-4 | |
| 1.308 | 4'-CONH₂ | H | H | 3-SC(F₂)S-4 | |
| 1.309 | 4'-CONH₂ | H | 2-F | 4-NH₂ | |
| 1.310 | 4'-CONH₂ | H | 2-Cl | 4-COOH | |
| 1.311 | 4'-CONH₂ | H | 2-CN | 4-CONH₂ | |
| 1.312 | 4'-CONH₂ | H | 2-CH₃ | 4-CSNH₂ | |
| 1.313 | 4'-CONH₂ | H | 2-CF₃ | 4-NHCONH₂ | |
| 1.314 | 4'-CONH₂ | H | 2-OCF₃ | 4-NHCSNH₂ | |
| 1.315 | 4'-CONH₂ | H | 2-SCF₃ | 4-OCSNH₂ | |
| 1.316 | 4'-CONH₂ | 2'-CN | H | H | |
| 1.317 | 4'-CONH₂ | 2'-CN | 4-F | H | |
| 1.318 | 4'-CONH₂ | 2'-CN | 4-Cl | H | |
| 1.319 | 4'-CONH₂ | 2'-CN | 4-CN | H | |
| 1.320 | 4'-CONH₂ | 2'-CN | 4-CH₃ | H | |
| 1.321 | 4'-CONH₂ | 2'-CN | 4-CF₃ | H | |
| 1.322 | 4'-CONH₂ | 2'-CN | 4-OCF₃ | H | |
| 1.323 | 4'-CONH₂ | 2'-CN | 4-SCF₃ | H | |
| 1.324 | 4'-CONH₂ | 2'-CN | 4-S(O)CF₃ | H | |
| 1.325 | 4'-CONH₂ | 2'-CN | 4-S(O)₂CF₃ | H | |
| 1.326 | 4'-CONH₂ | 2'-CN | 2-F | H | |
| 1.327 | 4'-CONH₂ | 2'-CN | 2-Cl | H | |
| 1.328 | 4'-CONH₂ | 2'-CN | 2-CN | H | |
| 1.329 | 4'-CONH₂ | 2'-CN | 2-CH₃ | H | |
| 1.330 | 4'-CONH₂ | 2'-CN | 2-CF₃ | H | |
| 1.331 | 4'-CONH₂ | 2'-CN | 2-OCF₃ | H | |
| 1.332 | 4'-CONH₂ | 2'-CN | 2-SCF₃ | H | |
| 1.333 | 4'-CONH₂ | 2'-CN | 2-S(O)CF₃ | H | |
| 1.334 | 4'-CONH₂ | 2'-CN | 2-S(O)₂CF₃ | H | |
| 1.335 | 4'-CONH₂ | 2'-CN | H | 4-NH₂ | |
| 1.336 | 4'-CONH₂ | 2'-CN | H | 4-COOH | |
| 1.337 | 4'-CONH₂ | 2'-CN | H | 4-CONH₂ | |
| 1.338 | 4'-CONH₂ | 2'-CN | H | 4-CSNH₂ | |
| 1.339 | 4'-CONH₂ | 2'-CN | H | 4-NHCONH₂ | |
| 1.340 | 4'-CONH₂ | 2'-CN | H | 4-NHCSNH₂ | |
| 1.341 | 4'-CONH₂ | 2'-CN | H | 4-OCSNH₂ | |
| 1.342 | 4'-CONH₂ | 2'-CN | H | 3-OC(F₂)O-4 | |
| 1.343 | 4'-CONH₂ | 2'-CN | H | 3-SC(F₂)S-4 | |
| 1.344 | 4'-CONH₂ | 2'-CN | 2-F | 4-NH₂ | |
| 1.345 | 4'-CONH₂ | 2'-CN | 2-Cl | 4-COOH | |
| 1.346 | 4'-CONH₂ | 2'-CN | 2-CN | 4-CONH₂ | |

TABLE 1-continued

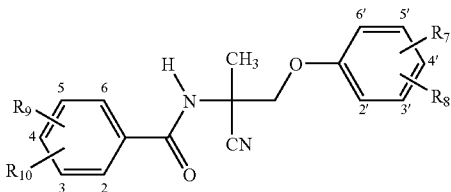

| No. | R_7 | R_8 | R_9 | R_10 | Phys. data |
|---|---|---|---|---|---|
| 1.347 | 4'-CONH$_2$ | 2'-CN | 2-CH$_3$ | 4-CSNH$_2$ | |
| 1.348 | 4'-CONH$_2$ | 2'-CN | 2-CF$_3$ | 4-NHCONH$_2$ | |
| 1.349 | 4'-CONH$_2$ | 2'-CN | 2-OCF$_3$ | 4-NHCSNH$_2$ | |
| 1.350 | 4'-CONH$_2$ | 2'-CN | 2-SCF$_3$ | 4-OCSNH$_2$ | |
| 1.351 | 4'-CONH$_2$ | 2'-CH$_3$ | H | H | |
| 1.352 | 4'-CONH$_2$ | 2'-CH$_3$ | 4-F | H | |
| 1.353 | 4'-CONH$_2$ | 2'-CH$_3$ | 4-Cl | H | |
| 1.354 | 4'-CONH$_2$ | 2'-CH$_3$ | 4-CN | H | |
| 1.355 | 4'-CONH$_2$ | 2'-CH$_3$ | 4-CH$_3$ | H | |
| 1.356 | 4'-CONH$_2$ | 2'-CH$_3$ | 4-CF$_3$ | H | |
| 1.357 | 4'-CONH$_2$ | 2'-CH$_3$ | 4-OCF$_3$ | H | |
| 1.358 | 4'-CONH$_2$ | 2'-CH$_3$ | 4-SCF$_3$ | H | |
| 1.359 | 4'-CONH$_2$ | 2'-CH$_3$ | 4-S(O)CF$_3$ | H | |
| 1.360 | 4'-CONH$_2$ | 2'-CH$_3$ | 4-S(O)$_2$CF$_3$ | H | |
| 1.361 | 4'-CONH$_2$ | 2'-CH$_3$ | 2-F | H | |
| 1.362 | 4'-CONH$_2$ | 2'-CH$_3$ | 2-Cl | H | |
| 1.363 | 4'-CONH$_2$ | 2'-CH$_3$ | 2-CN | H | |
| 1.364 | 4'-CONH$_2$ | 2'-CH$_3$ | 2-CH$_3$ | H | |
| 1.365 | 4'-CONH$_2$ | 2'-CH$_3$ | 2-CF$_3$ | H | |
| 1.366 | 4'-CONH$_2$ | 2'-CH$_3$ | 2-OCF$_3$ | H | |
| 1.367 | 4'-CONH$_2$ | 2'-CH$_3$ | 2-SCF$_3$ | H | |
| 1.368 | 4'-CONH$_2$ | 2'-CH$_3$ | 2-S(O)CF$_3$ | H | |
| 1.369 | 4'-CONH$_2$ | 2'-CH$_3$ | 2-S(O)$_2$CF$_3$ | H | |
| 1.370 | 4'-CONH$_2$ | 2'-CH$_3$ | H | 4-NH$_2$ | |
| 1.371 | 4'-CONH$_2$ | 2'-CH$_3$ | H | 4-COOH | |
| 1.372 | 4'-CONH$_2$ | 2'-CH$_3$ | H | 4-CONH$_2$ | |
| 1.373 | 4'-CONH$_2$ | 2'-CH$_3$ | H | 4-CSNH$_2$ | |
| 1.374 | 4'-CONH$_2$ | 2'-CH$_3$ | H | 4-NHCONH$_2$ | |
| 1.375 | 4'-CONH$_2$ | 2'-CH$_3$ | H | 4-NHCSNH$_2$ | |
| 1.376 | 4'-CONH$_2$ | 2'-CH$_3$ | H | 4-OCSNH$_2$ | |
| 1.377 | 4'-CONH$_2$ | 2'-CH$_3$ | H | 3-OC(F$_2$)O-4 | |
| 1.378 | 4'-CONH$_2$ | 2'-CH$_3$ | H | 3-SC(F$_2$)S-4 | |
| 1.379 | 4'-CONH$_2$ | 2'-CH$_3$ | 2-F | 4-NH$_2$ | |
| 1.380 | 4'-CONH$_2$ | 2'-CH$_3$ | 2-Cl | 4-COOH | |
| 1.381 | 4'-CONH$_2$ | 2'-CH$_3$ | 2-CN | 4-CONH$_2$ | |
| 1.382 | 4'-CONH$_2$ | 2'-CH$_3$ | 2-CH$_3$ | 4-CSNH$_2$ | |
| 1.383 | 4'-CONH$_2$ | 2'-CH$_3$ | 2-CF$_3$ | 4-NHCONH$_2$ | |
| 1.384 | 4'-CONH$_2$ | 2'-CH$_3$ | 2-OCF$_3$ | 4-NHCSNH$_2$ | |
| 1.385 | 4'-CONH$_2$ | 2'-CH$_3$ | 2-SCF$_3$ | 4-OCSNH$_2$ | |
| 1.386 | 4'-CONH$_2$ | 2'-CF$_3$ | H | H | |
| 1.387 | 4'-CONH$_2$ | 2'-CF$_3$ | 4-F | H | |
| 1.388 | 4'-CONH$_2$ | 2'-CF$_3$ | 4-Cl | H | |
| 1.389 | 4'-CONH$_2$ | 2'-CF$_3$ | 4-CN | H | |
| 1.390 | 4'-CONH$_2$ | 2'-CF$_3$ | 4-CH$_3$ | H | |
| 1.391 | 4'-CONH$_2$ | 2'-CF$_3$ | 4-CF$_3$ | H | |
| 1.392 | 4'-CONH$_2$ | 2'-CF$_3$ | 4-OCF$_3$ | H | m.p. 104-10° |
| 1.393 | 4'-CONH$_2$ | 2'-CF$_3$ | 4-SCF$_3$ | H | |
| 1.394 | 4'-CONH$_2$ | 2'-CF$_3$ | 4-S(O)CF$_3$ | H | |
| 1.395 | 4'-CONH$_2$ | 2'-CF$_3$ | 4-S(O)$_2$CF$_3$ | H | |
| 1.396 | 4'-CONH$_2$ | 2'-CF$_3$ | 2-F | H | |
| 1.397 | 4'-CONH$_2$ | 2'-CF$_3$ | 2-Cl | H | |
| 1.398 | 4'-CONH$_2$ | 2'-CF$_3$ | 2-CN | H | |
| 1.399 | 4'-CONH$_2$ | 2'-CF$_3$ | 2-CH$_3$ | H | |
| 1.400 | 4'-CONH$_2$ | 2'-CF$_3$ | 2-CF$_3$ | H | |
| 1.401 | 4'-CONH$_2$ | 2'-CF$_3$ | 2-OCF$_3$ | H | |
| 1.402 | 4'-CONH$_2$ | 2'-CF$_3$ | 2-SCF$_3$ | H | |
| 1.403 | 4'-CONH$_2$ | 2'-CF$_3$ | 2-S(O)CF$_3$ | H | |
| 1.404 | 4'-CONH$_2$ | 2'-CF$_3$ | 2-S(O)$_2$CF$_3$ | H | |
| 1.405 | 4'-CONH$_2$ | 2'-CF$_3$ | H | 4-NH$_2$ | |
| 1.406 | 4'-CONH$_2$ | 2'-CF$_3$ | H | 4-COOH | |
| 1.407 | 4'-CONH$_2$ | 2'-CF$_3$ | H | 4-CONH$_2$ | |
| 1.408 | 4'-CONH$_2$ | 2'-CF$_3$ | H | 4-CSNH$_2$ | |
| 1.409 | 4'-CONH$_2$ | 2'-CF$_3$ | H | 4-NHCONH$_2$ | |
| 1.410 | 4'-CONH$_2$ | 2'-CF$_3$ | H | 4-NHCSNH$_2$ | |
| 1.411 | 4'-CONH$_2$ | 2'-CF$_3$ | H | 4-OCSNH$_2$ | |
| 1.412 | 4'-CONH$_2$ | 2'-CF$_3$ | H | 3-OC(F$_2$)O-4 | |

TABLE 1-continued

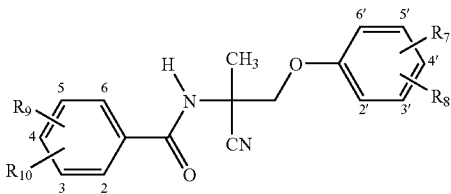

| No. | $R_7$ | $R_8$ | $R_9$ | $R_{10}$ | Phys. data |
|---|---|---|---|---|---|
| 1.413 | 4'-CONH$_2$ | 2'-CF$_3$ | H | 3-SC(F$_2$)S-4 | |
| 1.414 | 4'-CONH$_2$ | 2'-CF$_3$ | 2-F | 4-NH$_2$ | |
| 1.415 | 4'-CONH$_2$ | 2'-CF$_3$ | 2-Cl | 4-COOH | |
| 1.416 | 4'-CONH$_2$ | 2'-CF$_3$ | 2-CN | 4-CONH$_2$ | |
| 1.417 | 4'-CONH$_2$ | 2'-CF$_3$ | 2-CH$_3$ | 4-CSNH$_2$ | |
| 1.418 | 4'-CONH$_2$ | 2'-CF$_3$ | 2-CF$_3$ | 4-NHCONH$_2$ | |
| 1.419 | 4'-CONH$_2$ | 2'-CF$_3$ | 2-OCF$_3$ | 4-NHCSNH$_2$ | |
| 1.420 | 4'-CONH$_2$ | 2'-CF$_3$ | 2-SCF$_3$ | 4-OCSNH$_2$ | |
| 1.421 | 4'-CONH$_2$ | 2'-OCF$_3$ | H | H | |
| 1.422 | 4'-CONH$_2$ | 2'-OCF$_3$ | 4-F | H | |
| 1.423 | 4'-CONH$_2$ | 2'-OCF$_3$ | 4-Cl | H | |
| 1.424 | 4'-CONH$_2$ | 2'-OCF$_3$ | 4-CN | H | |
| 1.425 | 4'-CONH$_2$ | 2'-OCF$_3$ | 4-CH$_3$ | H | |
| 1.426 | 4'-CONH$_2$ | 2'-OCF$_3$ | 4-CF$_3$ | H | |
| 1.427 | 4'-CONH$_2$ | 2'-OCF$_3$ | 4-OCF$_3$ | H | |
| 1.428 | 4'-CONH$_2$ | 2'-OCF$_3$ | 4-SCF$_3$ | H | |
| 1.429 | 4'-CONH$_2$ | 2'-OCF$_3$ | 4-S(O)CF$_3$ | H | |
| 1.430 | 4'-CONH$_2$ | 2'-OCF$_3$ | 4-S(O)$_2$CF$_3$ | H | |
| 1.431 | 4'-CONH$_2$ | 2'-OCF$_3$ | 2-F | H | |
| 1.432 | 4'-CONH$_2$ | 2'-OCF$_3$ | 2-Cl | H | |
| 1.433 | 4'-CONH$_2$ | 2'-OCF$_3$ | 2-CN | H | |
| 1.434 | 4'-CONH$_2$ | 2'-OCF$_3$ | 2-CH$_3$ | H | |
| 1.435 | 4'-CONH$_2$ | 2'-OCF$_3$ | 2-CF$_3$ | H | |
| 1.436 | 4'-CONH$_2$ | 2'-OCF$_3$ | 2-OCF$_3$ | H | |
| 1.437 | 4'-CONH$_2$ | 2'-OCF$_3$ | 2-SCF$_3$ | H | |
| 1.438 | 4'-CONH$_2$ | 2'-OCF$_3$ | 2-S(O)CF$_3$ | H | |
| 1.439 | 4'-CONH$_2$ | 2'-OCF$_3$ | 2-S(O)$_2$CF$_3$ | H | |
| 1.440 | 4'-CONH$_2$ | 2'-OCF$_3$ | H | 4-NH$_2$ | |
| 1.441 | 4'-CONH$_2$ | 2'-OCF$_3$ | H | 4-COOH | |
| 1.442 | 4'-CONH$_2$ | 2'-OCF$_3$ | H | 4-CONH$_2$ | |
| 1.443 | 4'-CONH$_2$ | 2'-OCF$_3$ | H | 4-CSNH$_2$ | |
| 1.444 | 4'-CONH$_2$ | 2'-OCF$_3$ | H | 4-NHCONH$_2$ | |
| 1.445 | 4'-CONH$_2$ | 2'-OCF$_3$ | H | 4-NHCSNH$_2$ | |
| 1.446 | 4'-CONH$_2$ | 2'-OCF$_3$ | H | 4-OCSNH$_2$ | |
| 1.447 | 4'-CONH$_2$ | 2'-OCF$_3$ | H | 3-OC(F$_2$)O-4 | |
| 1.448 | 4'-CONH$_2$ | 2'-OCF$_3$ | H | 3-SC(F$_2$)S-4 | |
| 1.449 | 4'-CONH$_2$ | 2'-OCF$_3$ | 2-F | 4-NH$_2$ | |
| 1.450 | 4'-CONH$_2$ | 2'-OCF$_3$ | 2-Cl | 4-COOH | |
| 1.451 | 4'-CONH$_2$ | 2'-OCF$_3$ | 2-CN | 4-CONH$_2$ | |
| 1.452 | 4'-CONH$_2$ | 2'-OCF$_3$ | 2-CH$_3$ | 4-CSNH$_2$ | |
| 1.453 | 4'-CONH$_2$ | 2'-OCF$_3$ | 2-CF$_3$ | 4-NHCONH$_2$ | |
| 1.454 | 4'-CONH$_2$ | 2'-OCF$_3$ | 2-OCF$_3$ | 4-NHCSNH$_2$ | |
| 1.455 | 4'-CONH$_2$ | 2'-OCF$_3$ | 2-SCF$_3$ | 4-OCSNH$_2$ | |
| 1.456 | 4'-CONH$_2$ | 2'-C$_6$H$_5$ | H | H | |
| 1.457 | 4'-CONH$_2$ | 2'-C$_6$H$_5$ | 4-F | H | |
| 1.458 | 4'-CONH$_2$ | 2'-C$_6$H$_5$ | 4-Cl | H | |
| 1.459 | 4'-CONH$_2$ | 2'-C$_6$H$_5$ | 4-CN | H | |
| 1.460 | 4'-CONH$_2$ | 2'-C$_6$H$_5$ | 4-CH$_3$ | H | |
| 1.461 | 4'-CONH$_2$ | 2'-C$_6$H$_5$ | 4-CF$_3$ | H | |
| 1.462 | 4'-CONH$_2$ | 2'-C$_6$H$_5$ | 4-OCF$_3$ | H | |
| 1.463 | 4'-CONH$_2$ | 2'-C$_6$H$_5$ | 4-SCF$_3$ | H | |
| 1.464 | 4'-CONH$_2$ | 2'-C$_6$H$_5$ | 4-S(O)CF$_3$ | H | |
| 1.465 | 4'-CONH$_2$ | 2'-C$_6$H$_5$ | 4-S(O)$_2$CF$_3$ | H | |
| 1.466 | 4'-CONH$_2$ | 2'-C$_6$H$_5$ | 2-F | H | |
| 1.467 | 4'-CONH$_2$ | 2'-C$_6$H$_5$ | 2-Cl | H | |
| 1.468 | 4'-CONH$_2$ | 2'-C$_6$H$_5$ | 2-CN | H | |
| 1.469 | 4'-CONH$_2$ | 2'-C$_6$H$_5$ | 2-CH$_3$ | H | |
| 1.470 | 4'-CONH$_2$ | 2'-C$_6$H$_5$ | 2-CF$_3$ | H | |
| 1.471 | 4'-CONH$_2$ | 2'-C$_6$H$_5$ | 2-OCF$_3$ | H | |
| 1.472 | 4'-CONH$_2$ | 2'-C$_6$H$_5$ | 2-SCF$_3$ | H | |
| 1.473 | 4'-CONH$_2$ | 2'-C$_6$H$_5$ | 2-S(O)CF$_3$ | H | |
| 1.474 | 4'-CONH$_2$ | 2'-C$_6$H$_5$ | 2-S(O)$_2$CF$_3$ | H | |
| 1.475 | 4'-CONH$_2$ | 2'-C$_6$H$_5$ | H | 4-NH$_2$ | |
| 1.476 | 4'-CONH$_2$ | 2'-C$_6$H$_5$ | H | 4-COOH | |
| 1.477 | 4'-CONH$_2$ | 2'-C$_6$H$_5$ | H | 4-CONH$_2$ | |
| 1.478 | 4'-CONH$_2$ | 2'-C$_6$H$_5$ | H | 4-CSNH$_2$ | |

TABLE 1-continued

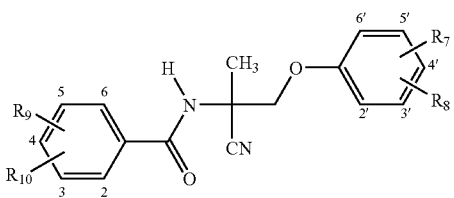

| No. | $R_7$ | $R_8$ | $R_9$ | $R_{10}$ | Phys. data |
|---|---|---|---|---|---|
| 1.479 | 4'-CONH$_2$ | 2'-C$_6$H$_5$ | H | 4-NHCONH$_2$ | |
| 1.480 | 4'-CONH$_2$ | 2'-C$_6$H$_5$ | H | 4-NHCSNH$_2$ | |
| 1.481 | 4'-CONH$_2$ | 2'-C$_6$H$_5$ | H | 4-OCSNH$_2$ | |
| 1.482 | 4'-CONH$_2$ | 2'-C$_6$H$_5$ | H | 3-OC(F$_2$)O-4 | |
| 1.483 | 4'-CONH$_2$ | 2'-C$_6$H$_5$ | H | 3-SC(F$_2$)S-4 | |
| 1.484 | 4'-CONH$_2$ | 2'-C$_6$H$_5$ | 2-F | 4-NH$_2$ | |
| 1.485 | 4'-CONH$_2$ | 2'-C$_6$H$_5$ | 2-Cl | 4-COOH | |
| 1.486 | 4'-CONH$_2$ | 2'-C$_6$H$_5$ | 2-CN | 4-CONH$_2$ | |
| 1.487 | 4'-CONH$_2$ | 2'-C$_6$H$_5$ | 2-CH$_3$ | 4-CSNH$_2$ | |
| 1.488 | 4'-CONH$_2$ | 2'-C$_6$H$_5$ | 2-CF$_3$ | 4-NHCONH$_2$ | |
| 1.489 | 4'-CONH$_2$ | 2'-C$_6$H$_5$ | 2-OCF$_3$ | 4-NHCSNH$_2$ | |
| 1.490 | 4'-CONH$_2$ | 2'-C$_6$H$_5$ | 2-SCF$_3$ | 4-OCSNH$_2$ | |
| 1.491 | 4'-CONH$_2$ | 2'-(C$_6$H$_4$-4-Cl) | H | H | |
| 1.492 | 4'-CONH$_2$ | 2'-(C$_6$H$_4$-4-Cl) | 4-F | H | |
| 1.493 | 4'-CONH$_2$ | 2'-(C$_6$H$_4$-4-Cl) | 4-Cl | H | |
| 1.494 | 4'-CONH$_2$ | 2'-(C$_6$H$_4$-4-Cl) | 4-CN | H | |
| 1.495 | 4'-CONH$_2$ | 2'-(C$_6$H$_4$-4-Cl) | 4-CH$_3$ | H | |
| 1.496 | 4'-CONH$_2$ | 2'-(C$_6$H$_4$-4-Cl) | 4-CF$_3$ | H | |
| 1.497 | 4'-CONH$_2$ | 2'-(C$_6$H$_4$-4-Cl) | 4-OCF$_3$ | H | |
| 1.498 | 4'-CONH$_2$ | 2'-(C$_6$H$_4$-4-Cl) | 4-SCF$_3$ | H | |
| 1.499 | 4'-CONH$_2$ | 2'-(C$_6$H$_4$-4-Cl) | 4-S(O)CF$_3$ | H | |
| 1.500 | 4'-CONH$_2$ | 2'-(C$_6$H$_4$-4-Cl) | 4-S(O)$_2$CF$_3$ | H | |
| 1.501 | 4'-CONH$_2$ | 2'-(C$_6$H$_4$-4-Cl) | 2-F | H | |
| 1.502 | 4'-CONH$_2$ | 2'-(C$_6$H$_4$-4-Cl) | 2-Cl | H | |
| 1.503 | 4'-CONH$_2$ | 2'-(C$_6$H$_4$-4-Cl) | 2-CN | H | |
| 1.504 | 4'-CONH$_2$ | 2'-(C$_6$H$_4$-4-Cl) | 2-CH$_3$ | H | |
| 1.505 | 4'-CONH$_2$ | 2'-(C$_6$H$_4$-4-Cl) | 2-CF$_3$ | H | |
| 1.506 | 4'-CONH$_2$ | 2'-(C$_6$H$_4$-4-Cl) | 2-OCF$_3$ | H | |
| 1.507 | 4'-CONH$_2$ | 2'-(C$_6$H$_4$-4-Cl) | 2-SCF$_3$ | H | |
| 1.508 | 4'-CONH$_2$ | 2'-(C$_6$H$_4$-4-Cl) | 2-S(O)CF$_3$ | H | |
| 1.509 | 4'-CONH$_2$ | 2'-(C$_6$H$_4$-4-Cl) | 2-S(O)$_2$CF$_3$ | H | |
| 1.510 | 4'-CONH$_2$ | 2'-(C$_6$H$_4$-4-Cl) | H | 4-NH$_2$ | |
| 1.511 | 4'-CONH$_2$ | 2'-(C$_6$H$_4$-4-Cl) | H | 4-COOH | |
| 1.512 | 4'-CONH$_2$ | 2'-(C$_6$H$_4$-4-Cl) | H | 4-CONH$_2$ | |
| 1.513 | 4'-CONH$_2$ | 2'-(C$_6$H$_4$-4-Cl) | H | 4-CSNH$_2$ | |
| 1.514 | 4'-CONH$_2$ | 2'-(C$_6$H$_4$-4-Cl) | H | 4-NHCONH$_2$ | |
| 1.515 | 4'-CONH$_2$ | 2'-(C$_6$H$_4$-4-Cl) | H | 4-NHCSNH$_2$ | |
| 1.516 | 4'-CONH$_2$ | 2'-(C$_6$H$_4$-4-Cl) | H | 4-OCSNH$_2$ | |
| 1.517 | 4'-CONH$_2$ | 2'-(C$_6$H$_4$-4-Cl) | H | 3-OC(F$_2$)O-4 | |
| 1.518 | 4'-CONH$_2$ | 2'-(C$_6$H$_4$-4-Cl) | H | 3-SC(F$_2$)S-4 | |
| 1.519 | 4'-CONH$_2$ | 2'-(C$_6$H$_4$-4-Cl) | 2-F | 4-NH$_2$ | |
| 1.520 | 4'-CONH$_2$ | 2'-(C$_6$H$_4$-4-Cl) | 2-Cl | 4-COOH | |
| 1.521 | 4'-CONH$_2$ | 2'-(C$_6$H$_4$-4-Cl) | 2-CN | 4-CONH$_2$ | |
| 1.522 | 4'-CONH$_2$ | 2'-(C$_6$H$_4$-4-Cl) | 2-CH$_3$ | 4-CSNH$_2$ | |
| 1.523 | 4'-CONH$_2$ | 2'-(C$_6$H$_4$-4-Cl) | 2-CF$_3$ | 4-NHCONH$_2$ | |
| 1.524 | 4'-CONH$_2$ | 2'-(C$_6$H$_4$-4-Cl) | 2-OCF$_3$ | 4-NHCSNH$_2$ | |
| 1.525 | 4'-CONH$_2$ | 2'-(C$_6$H$_4$-4-Cl) | 2-SCF$_3$ | 4-OCSNH$_2$ | |
| 1.526 | 4'-CONH$_2$ | 2'-(C$_6$H$_3$-2,4-Cl$_2$) | H | H | |
| 1.527 | 4'-CONH$_2$ | 2'-(C$_6$H$_3$-2,4-Cl$_2$) | 4-F | H | |
| 1.528 | 4'-CONH$_2$ | 2'-(C$_6$H$_3$-2,4-Cl$_2$) | 4-Cl | H | |
| 1.529 | 4'-CONH$_2$ | 2'-(C$_6$H$_3$-2,4-Cl$_2$) | 4-CN | H | |
| 1.530 | 4'-CONH$_2$ | 2'-(C$_6$H$_3$-2,4-Cl$_2$) | 4-CH$_3$ | H | |
| 1.531 | 4'-CONH$_2$ | 2'-(C$_6$H$_3$-2,4-Cl$_2$) | 4-CF$_3$ | H | |
| 1.532 | 4'-CONH$_2$ | 2'-(C$_6$H$_3$-2,4-Cl$_2$) | 4-OCF$_3$ | H | |
| 1.533 | 4'-CONH$_2$ | 2'-(C$_6$H$_3$-2,4-Cl$_2$) | 4-SCF$_3$ | H | |
| 1.534 | 4'-CONH$_2$ | 2'-(C$_6$H$_3$-2,4-Cl$_2$) | 4-S(O)CF$_3$ | H | |
| 1.535 | 4'-CONH$_2$ | 2'-(C$_6$H$_3$-2,4-Cl$_2$) | 4-S(O)$_2$CF$_3$ | H | |
| 1.536 | 4'-CONH$_2$ | 2'-(C$_6$H$_3$-2,4-Cl$_2$) | 2-F | H | |
| 1.537 | 4'-CONH$_2$ | 2'-(C$_6$H$_3$-2,4-Cl$_2$) | 2-Cl | H | |
| 1.538 | 4'-CONH$_2$ | 2'-(C$_6$H$_3$-2,4-Cl$_2$) | 2-CN | H | |
| 1.539 | 4'-CONH$_2$ | 2'-(C$_6$H$_3$-2,4-Cl$_2$) | 2-CH$_3$ | H | |
| 1.540 | 4'-CONH$_2$ | 2'-(C$_6$H$_3$-2,4-Cl$_2$) | 2-CF$_3$ | H | |
| 1.541 | 4'-CONH$_2$ | 2'-(C$_6$H$_3$-2,4-Cl$_2$) | 2-OCF$_3$ | H | |
| 1.542 | 4'-CONH$_2$ | 2'-(C$_6$H$_3$-2,4-Cl$_2$) | 2-SCF$_3$ | H | |
| 1.543 | 4'-CONH$_2$ | 2'-(C$_6$H$_3$-2,4-Cl$_2$) | 2-S(O)CF$_3$ | H | |
| 1.544 | 4'-CONH$_2$ | 2'-(C$_6$H$_3$-2,4-Cl$_2$) | 2-S(O)$_2$CF$_3$ | H | |

TABLE 1-continued

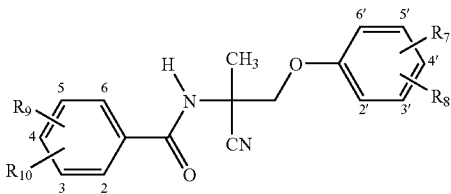

| No. | R₇ | R₈ | R₉ | R₁₀ | Phys. data |
|---|---|---|---|---|---|
| 1.545 | 4'-CONH₂ | 2'-(C₆H₃-2,4-Cl₂) | H | 4-NH₂ | |
| 1.546 | 4'-CONH₂ | 2'-(C₆H₃-2,4-Cl₂) | H | 4-COOH | |
| 1.547 | 4'-CONH₂ | 2'-(C₆H₃-2,4-Cl₂) | H | 4-CONH₂ | |
| 1.548 | 4'-CONH₂ | 2'-(C₆H₃-2,4-Cl₂) | H | 4-CSNH₂ | |
| 1.549 | 4'-CONH₂ | 2'-(C₆H₃-2,4-Cl₂) | H | 4-NHCONH₂ | |
| 1.550 | 4'-CONH₂ | 2'-(C₆H₃-2,4-Cl₂) | H | 4-NHCSNH₂ | |
| 1.551 | 4'-CONH₂ | 2'-(C₆H₃-2,4-Cl₂) | H | 4-OCSNH₂ | |
| 1.552 | 4'-CONH₂ | 2'-(C₆H₃-2,4-Cl₂) | H | 3-OC(F₂)O-4 | |
| 1.553 | 4'-CONH₂ | 2'-(C₆H₃-2,4-Cl₂) | H | 3-SC(F₂)S-4 | |
| 1.554 | 4'-CONH₂ | 2'-(C₆H₃-2,4-Cl₂) | 2-F | 4-NH₂ | |
| 1.555 | 4'-CONH₂ | 2'-(C₆H₃-2,4-Cl₂) | 2-Cl | 4-COOH | |
| 1.556 | 4'-CONH₂ | 2'-(C₆H₃-2,4-Cl₂) | 2-CN | 4-CONH₂ | |
| 1.557 | 4'-CONH₂ | 2'-(C₆H₃-2,4-Cl₂) | 2-CH₃ | 4-CSNH₂ | |
| 1.558 | 4'-CONH₂ | 2'-(C₆H₃-2,4-Cl₂) | 2-CF₃ | 4-NHCONH₂ | |
| 1.559 | 4'-CONH₂ | 2'-(C₆H₃-2,4-Cl₂) | 2-OCF₃ | 4-NHCSNH₂ | |
| 1.560 | 4'-CONH₂ | 2'-(C₆H₃-2,4-Cl₂) | 2-SCF₃ | 4-OCSNH₂ | |
| 1.561 | 4'-CONH₂ | 2'-OC₆H₅ | H | H | |
| 1.562 | 4'-CONH₂ | 2'-OC₆H₅ | 4-F | H | |
| 1.563 | 4'-CONH₂ | 2'-OC₆H₅ | 4-Cl | H | |
| 1.564 | 4'-CONH₂ | 2'-OC₆H₅ | 4-CN | H | |
| 1.565 | 4'-CONH₂ | 2'-OC₆H₅ | 4-CH₃ | H | |
| 1.566 | 4'-CONH₂ | 2'-OC₆H₅ | 4-CF₃ | H | |
| 1.567 | 4'-CONH₂ | 2'-OC₆H₅ | 4-OCF₃ | H | |
| 1.568 | 4'-CONH₂ | 2'-OC₆H₅ | 4-SCF₃ | H | |
| 1.569 | 4'-CONH₂ | 2'-OC₆H₅ | 4-S(O)CF₃ | H | |
| 1.570 | 4'-CONH₂ | 2'-OC₆H₅ | 4-S(O)₂CF₃ | H | |
| 1.571 | 4'-CONH₂ | 2'-OC₆H₅ | 2-F | H | |
| 1.572 | 4'-CONH₂ | 2'-OC₆H₅ | 2-Cl | H | |
| 1.573 | 4'-CONH₂ | 2'-OC₆H₅ | 2-CN | H | |
| 1.574 | 4'-CONH₂ | 2'-OC₆H₅ | 2-CH₃ | H | |
| 1.575 | 4'-CONH₂ | 2'-OC₆H₅ | 2-CF₃ | H | |
| 1.576 | 4'-CONH₂ | 2'-OC₆H₅ | 2-OCF₃ | H | |
| 1.577 | 4'-CONH₂ | 2'-OC₆H₅ | 2-SCF₃ | H | |
| 1.578 | 4'-CONH₂ | 2'-OC₆H₅ | 2-S(O)CF₃ | H | |
| 1.579 | 4'-CONH₂ | 2'-OC₆H₅ | 2-S(O)₂CF₃ | H | |
| 1.580 | 4'-CONH₂ | 2'-OC₆H₅ | H | 4-NH₂ | |
| 1.581 | 4'-CONH₂ | 2'-OC₆H₅ | H | 4-COOH | |
| 1.582 | 4'-CONH₂ | 2'-OC₆H₅ | H | 4-CONH₂ | |
| 1.583 | 4'-CONH₂ | 2'-OC₆H₅ | H | 4-CSNH₂ | |
| 1.584 | 4'-CONH₂ | 2'-OC₆H₅ | H | 4-NHCONH₂ | |
| 1.585 | 4'-CONH₂ | 2'-OC₆H₅ | H | 4-NHCSNH₂ | |
| 1.586 | 4'-CONH₂ | 2'-OC₆H₅ | H | 4-OCSNH₂ | |
| 1.587 | 4'-CONH₂ | 2'-OC₆H₅ | H | 3-OC(F₂)O-4 | |
| 1.588 | 4'-CONH₂ | 2'-OC₆H₅ | H | 3-SC(F₂)S-4 | |
| 1.589 | 4'-CONH₂ | 2'-OC₆H₅ | 2-F | 4-NH₂ | |
| 1.590 | 4'-CONH₂ | 2'-OC₆H₅ | 2-Cl | 4-COOH | |
| 1.591 | 4'-CONH₂ | 2'-OC₆H₅ | 2-CN | 4-CONH₂ | |
| 1.592 | 4'-CONH₂ | 2'-OC₆H₅ | 2-CH₃ | 4-CSNH₂ | |
| 1.593 | 4'-CONH₂ | 2'-OC₆H₅ | 2-CF₃ | 4-NHCONH₂ | |
| 1.594 | 4'-CONH₂ | 2'-OC₆H₅ | 2-OCF₃ | 4-NHCSNH₂ | |
| 1.595 | 4'-CONH₂ | 2'-OC₆H₅ | 2-SCF₃ | 4-OCSNH₂ | |
| 1.596 | 4'-CONH₂ | 2'-(OC₆H₄-4-Cl) | H | H | |
| 1.597 | 4'-CONH₂ | 2'-(OC₆H₄-4-Cl) | 4-F | H | |
| 1.598 | 4'-CONH₂ | 2'-(OC₆H₄-4-Cl) | 4-Cl | H | |
| 1.599 | 4'-CONH₂ | 2'-(OC₆H₄-4-Cl) | 4-CN | H | |
| 1.600 | 4'-CONH₂ | 2'-(OC₆H₄-4-Cl) | 4-CH₃ | H | |
| 1.601 | 4'-CONH₂ | 2'-(OC₆H₄-4-Cl) | 4-CF₃ | H | |
| 1.602 | 4'-CONH₂ | 2'-(OC₆H₄-4-Cl) | 4-OCF₃ | H | |
| 1.603 | 4'-CONH₂ | 2'-(OC₆H₄-4-Cl) | 4-SCF₃ | H | |
| 1.604 | 4'-CONH₂ | 2'-(OC₆H₄-4-Cl) | 4-S(O)CF₃ | H | |
| 1.605 | 4'-CONH₂ | 2'-(OC₆H₄-4-Cl) | 4-S(O)₂CF₃ | H | |
| 1.606 | 4'-CONH₂ | 2'-(OC₆H₄-4-Cl) | 2-F | H | |
| 1.607 | 4'-CONH₂ | 2'-(OC₆H₄-4-Cl) | 2-Cl | H | |
| 1.608 | 4'-CONH₂ | 2'-(OC₆H₄-4-Cl) | 2-CN | H | |
| 1.609 | 4'-CONH₂ | 2'-(OC₆H₄-4-Cl) | 2-CH₃ | H | |
| 1.610 | 4'-CONH₂ | 2'-(OC₆H₄-4-Cl) | 2-CF₃ | H | |

TABLE 1-continued

| No. | R$_7$ | R$_8$ | R$_9$ | R$_{10}$ | Phys. data |
|---|---|---|---|---|---|
| 1.611 | 4'-CONH$_2$ | 2'-(OC$_6$H$_4$-4-Cl) | 2-OCF$_3$ | H | |
| 1.612 | 4'-CONH$_2$ | 2'-(OC$_6$H$_4$-4-Cl) | 2-SCF$_3$ | H | |
| 1.613 | 4'-CONH$_2$ | 2'-(OC$_6$H$_4$-4-Cl) | 2-S(O)CF$_3$ | H | |
| 1.614 | 4'-CONH$_2$ | 2'-(OC$_6$H$_4$-4-Cl) | 2-S(O)$_2$CF$_3$ | H | |
| 1.615 | 4'-CONH$_2$ | 2'-(OC$_6$H$_4$-4-Cl) | H | 4-NH$_2$ | |
| 1.616 | 4'-CONH$_2$ | 2'-(OC$_6$H$_4$-4-Cl) | H | 4-COOH | |
| 1.617 | 4'-CONH$_2$ | 2'-(OC$_6$H$_4$-4-Cl) | H | 4-CONH$_2$ | |
| 1.618 | 4'-CONH$_2$ | 2'-(OC$_6$H$_4$-4-Cl) | H | 4-CSNH$_2$ | |
| 1.619 | 4'-CONH$_2$ | 2'-(OC$_6$H$_4$-4-Cl) | H | 4-NHCONH$_2$ | |
| 1.620 | 4'-CONH$_2$ | 2'-(OC$_6$H$_4$-4-Cl) | H | 4-NHCSNH$_2$ | |
| 1.621 | 4'-CONH$_2$ | 2'-(OC$_6$H$_4$-4-Cl) | H | 4-OCSNH$_2$ | |
| 1.622 | 4'-CONH$_2$ | 2'-(OC$_6$H$_4$-4-Cl) | H | 3-OC(F$_2$)O-4 | |
| 1.623 | 4'-CONH$_2$ | 2'-(OC$_6$H$_4$-4-Cl) | H | 3-SC(F$_2$)S-4 | |
| 1.624 | 4'-CONH$_2$ | 2'-(OC$_6$H$_4$-4-Cl) | 2-F | 4-NH$_2$ | |
| 1.625 | 4'-CONH$_2$ | 2'-(OC$_6$H$_4$-4-Cl) | 2-Cl | 4-COOH | |
| 1.626 | 4'-CONH$_2$ | 2'-(OC$_6$H$_4$-4-Cl) | 2-CN | 4-CONH$_2$ | |
| 1.627 | 4'-CONH$_2$ | 2'-(OC$_6$H$_4$-4-Cl) | 2-CH$_3$ | 4-CSNH$_2$ | |
| 1.628 | 4'-CONH$_2$ | 2'-(OC$_6$H$_4$-4-Cl) | 2-CF$_3$ | 4-NHCONH$_2$ | |
| 1.629 | 4'-CONH$_2$ | 2'-(OC$_6$H$_4$-4-Cl) | 2-OCF$_3$ | 4-NHCSNH$_2$ | |
| 1.630 | 4'-CONH$_2$ | 2'-(OC$_6$H$_4$-4-Cl) | 2-SCF$_3$ | 4-OCSNH$_2$ | |
| 1.631 | 4'-CONH$_2$ | 2'-(OC$_6$H$_3$-2,4-Cl$_2$) | H | H | |
| 1.632 | 4'-CONH$_2$ | 2'-(OC$_6$H$_3$-2,4-Cl$_2$) | 4-F | H | |
| 1.633 | 4'-CONH$_2$ | 2'-(OC$_6$H$_3$-2,4-Cl$_2$) | 4-Cl | H | |
| 1.634 | 4'-CONH$_2$ | 2'-(OC$_6$H$_3$-2,4-Cl$_2$) | 4-CN | H | |
| 1.635 | 4'-CONH$_2$ | 2'-(OC$_6$H$_3$-2,4-Cl$_2$) | 4-CH$_3$ | H | |
| 1.636 | 4'-CONH$_2$ | 2'-(OC$_6$H$_3$-2,4-Cl$_2$) | 4-CF$_3$ | H | |
| 1.637 | 4'-CONH$_2$ | 2'-(OC$_6$H$_3$-2,4-Cl$_2$) | 4-OCF$_3$ | H | |
| 1.638 | 4'-CONH$_2$ | 2'-(OC$_6$H$_3$-2,4-Cl$_2$) | 4-SCF$_3$ | H | |
| 1.639 | 4'-CONH$_2$ | 2'-(OC$_6$H$_3$-2,4-Cl$_2$) | 4-S(O)CF$_3$ | H | |
| 1.640 | 4'-CONH$_2$ | 2'-(OC$_6$H$_3$-2,4-Cl$_2$) | 4-S(O)$_2$CF$_3$ | H | |
| 1.641 | 4'-CONH$_2$ | 2'-(OC$_6$H$_3$-2,4-Cl$_2$) | 2-F | H | |
| 1.642 | 4'-CONH$_2$ | 2'-(OC$_6$H$_3$-2,4-Cl$_2$) | 2-Cl | H | |
| 1.643 | 4'-CONH$_2$ | 2'-(OC$_6$H$_3$-2,4-Cl$_2$) | 2-CN | H | |
| 1.644 | 4'-CONH$_2$ | 2'-(OC$_6$H$_3$-2,4-Cl$_2$) | 2-CH$_3$ | H | |
| 1.645 | 4'-CONH$_2$ | 2'-(OC$_6$H$_3$-2,4-Cl$_2$) | 2-CF$_3$ | H | |
| 1.646 | 4'-CONH$_2$ | 2'-(OC$_6$H$_3$-2,4-Cl$_2$) | 2-OCF$_3$ | H | |
| 1.647 | 4'-CONH$_2$ | 2'-(OC$_6$H$_3$-2,4-Cl$_2$) | 2-SCF$_3$ | H | |
| 1.648 | 4'-CONH$_2$ | 2'-(OC$_6$H$_3$-2,4-Cl$_2$) | 2-S(O)CF$_3$ | H | |
| 1.649 | 4'-CONH$_2$ | 2'-(OC$_6$H$_3$-2,4-Cl$_2$) | 2-S(O)$_2$CF$_3$ | H | |
| 1.650 | 4'-CONH$_2$ | 2'-(OC$_6$H$_3$-2,4-Cl$_2$) | H | 4-NH$_2$ | |
| 1.651 | 4'-CONH$_2$ | 2'-(OC$_6$H$_3$-2,4-Cl$_2$) | H | 4-COOH | |
| 1.652 | 4'-CONH$_2$ | 2'-(OC$_6$H$_3$-2,4-Cl$_2$) | H | 4-CONH$_2$ | |
| 1.653 | 4'-CONH$_2$ | 2'-(OC$_6$H$_3$-2,4-Cl$_2$) | H | 4-CSNH$_2$ | |
| 1.654 | 4'-CONH$_2$ | 2'-(OC$_6$H$_3$-2,4-Cl$_2$) | H | 4-NHCONH$_2$ | |
| 1.655 | 4'-CONH$_2$ | 2'-(OC$_6$H$_3$-2,4-Cl$_2$) | H | 4-NHCSNH$_2$ | |
| 1.656 | 4'-CONH$_2$ | 2'-(OC$_6$H$_3$-2,4-Cl$_2$) | H | 4-OCSNH$_2$ | |
| 1.657 | 4'-CONH$_2$ | 2'-(OC$_6$H$_3$-2,4-Cl$_2$) | H | 3-OC(F$_2$)O-4 | |
| 1.658 | 4'-CONH$_2$ | 2'-(OC$_6$H$_3$-2,4-Cl$_2$) | H | 3-SC(F$_2$)S-4 | |
| 1.659 | 4'-CONH$_2$ | 2'-(OC$_6$H$_3$-2,4-Cl$_2$) | 2-F | 4-NH$_2$ | |
| 1.660 | 4'-CONH$_2$ | 2'-(OC$_6$H$_3$-2,4-Cl$_2$) | 2-Cl | 4-COOH | |
| 1.661 | 4'-CONH$_2$ | 2'-(OC$_6$H$_3$-2,4-Cl$_2$) | 2-CN | 4-CONH$_2$ | |
| 1.662 | 4'-CONH$_2$ | 2'-(OC$_6$H$_3$-2,4-Cl$_2$) | 2-CH$_3$ | 4-CSNH$_2$ | |
| 1.663 | 4'-CONH$_2$ | 2'-(OC$_6$H$_3$-2,4-Cl$_2$) | 2-CF$_3$ | 4-NHCONH$_2$ | |
| 1.664 | 4'-CONH$_2$ | 2'-(OC$_6$H$_3$-2,4-Cl$_2$) | 2-OCF$_3$ | 4-NHCSNH$_2$ | |
| 1.665 | 4'-CONH$_2$ | 2'-(OC$_6$H$_3$-2,4-Cl$_2$) | 2-SCF$_3$ | 4-OCSNH$_2$ | |
| 1.666 | 5'-COOH | H | H | H | |
| 1.667 | 5'-COOH | H | 4-F | H | |
| 1.668 | 5'-COOH | H | 4-Cl | H | |
| 1.669 | 5'-COOH | H | 4-CN | H | |
| 1.670 | 5'-COOH | H | 4-CH$_3$ | H | |
| 1.671 | 5'-COOH | H | 4-CF$_3$ | H | |
| 1.672 | 5'-COOH | H | 4-OCF$_3$ | H | |
| 1.673 | 5'-COOH | H | 4-SCF$_3$ | H | |
| 1.674 | 5'-COOH | H | 4-S(O)CF$_3$ | H | |
| 1.675 | 5'-COOH | H | 4-S(O)$_2$CF$_3$ | H | |
| 1.676 | 5'-COOH | H | 2-F | H | |

TABLE 1-continued

| No. | R₇ | R₈ | R₉ | R₁₀ | Phys. data |
|---|---|---|---|---|---|
| 1.677 | 5'-COOH | H | 2-Cl | H | |
| 1.678 | 5'-COOH | H | 2-CN | H | |
| 1.679 | 5'-COOH | H | 2-CH₃ | H | |
| 1.680 | 5'-COOH | H | 2-CF₃ | H | |
| 1.681 | 5'-COOH | H | 2-OCF₃ | H | |
| 1.682 | 5'-COOH | H | 2-SCF₃ | H | |
| 1.683 | 5'-COOH | H | 2-S(O)CF₃ | H | |
| 1.684 | 5'-COOH | H | 2-S(O)₂CF₃ | H | |
| 1.685 | 5'-COOH | H | H | 4-NH₂ | |
| 1.686 | 5'-COOH | H | H | 4-COOH | |
| 1.687 | 5'-COOH | H | H | 4-CONH₂ | |
| 1.688 | 5'-COOH | H | H | 4-CSNH₂ | |
| 1.689 | 5'-COOH | H | H | 4-NHCONH₂ | |
| 1.690 | 5'-COOH | H | H | 4-NHCSNH₂ | |
| 1.691 | 5'-COOH | H | H | 4-OCSNH₂ | |
| 1.692 | 5'-COOH | H | H | 3-OC(F₂)O-4 | |
| 1.693 | 5'-COOH | H | H | 3-SC(F₂)S-4 | |
| 1.694 | 5'-COOH | H | 2-F | 4-NH₂ | |
| 1.695 | 5'-COOH | H | 2-Cl | 4-COOH | |
| 1.696 | 5'-COOH | H | 2-CN | 4-CONH₂ | |
| 1.697 | 5'-COOH | H | 2-CH₃ | 4-CSNH₂ | |
| 1.698 | 5'-COOH | H | 2-CF₃ | 4-NHCONH₂ | |
| 1.699 | 5'-COOH | H | 2-OCF₃ | 4-NHCSNH₂ | |
| 1.700 | 5'-COOH | H | 2-SCF₃ | 4-OCSNH₂ | |
| 1.701 | 5'-COOH | 2'-CN | H | H | |
| 1.702 | 5'-COOH | 2'-CN | 4-F | H | |
| 1.703 | 5'-COOH | 2'-CN | 4-Cl | H | |
| 1.704 | 5'-COOH | 2'-CN | 4-CN | H | |
| 1.705 | 5'-COOH | 2'-CN | 4-CH₃ | H | |
| 1.706 | 5'-COOH | 2'-CN | 4-CF₃ | H | |
| 1.707 | 5'-COOH | 2'-CN | 4-OCF₃ | H | |
| 1.708 | 5'-COOH | 2'-CN | 4-SCF₃ | H | |
| 1.709 | 5'-COOH | 2'-CN | 4-S(O)CF₃ | H | |
| 1.710 | 5'-COOH | 2'-CN | 4-S(O)₂CF₃ | H | |
| 1.711 | 5'-COOH | 2'-CN | 2-F | H | |
| 1.712 | 5'-COOH | 2'-CN | 2-Cl | H | |
| 1.713 | 5'-COOH | 2'-CN | 2-CN | H | |
| 1.714 | 5'-COOH | 2'-CN | 2-CH₃ | H | |
| 1.715 | 5'-COOH | 2'-CN | 2-CF₃ | H | |
| 1.716 | 5'-COOH | 2'-CN | 2-OCF₃ | H | |
| 1.717 | 5'-COOH | 2'-CN | 2-SCF₃ | H | |
| 1.718 | 5'-COOH | 2'-CN | 2-S(O)CF₃ | H | |
| 1.719 | 5'-COOH | 2'-CN | 2-S(O)₂CF₃ | H | |
| 1.720 | 5'-COOH | 2'-CN | H | 4-NH₂ | |
| 1.721 | 5'-COOH | 2'-CN | H | 4-COOH | |
| 1.722 | 5'-COOH | 2'-CN | H | 4-CONH₂ | |
| 1.723 | 5'-COOH | 2'-CN | H | 4-CSNH₂ | |
| 1.724 | 5'-COOH | 2'-CN | H | 4-NHCONH₂ | |
| 1.725 | 5'-COOH | 2'-CN | H | 4-NHCSNH₂ | |
| 1.726 | 5'-COOH | 2'-CN | H | 4-OCSNH₂ | |
| 1.727 | 5'-COOH | 2'-CN | H | 3-OC(F₂)O-4 | |
| 1.728 | 5'-COOH | 2'-CN | H | 3-SC(F₂)S-4 | |
| 1.729 | 5'-COOH | 2'-CN | 2-F | 4-NH₂ | |
| 1.730 | 5'-COOH | 2'-CN | 2-Cl | 4-COOH | |
| 1.731 | 5'-COOH | 2'-CN | 2-CN | 4-CONH₂ | |
| 1.732 | 5'-COOH | 2'-CN | 2-CH₃ | 4-CSNH₂ | |
| 1.733 | 5'-COOH | 2'-CN | 2-CF₃ | 4-NHCONH₂ | |
| 1.734 | 5'-COOH | 2'-CN | 2-OCF₃ | 4-NHCSNH₂ | |
| 1.735 | 5'-COOH | 2'-CN | 2-SCF₃ | 4-OCSNH₂ | |
| 1.736 | 5'-COOH | 2'-CH₃ | H | H | |
| 1.737 | 5'-COOH | 2'-CH₃ | 4-F | H | |
| 1.738 | 5'-COOH | 2'-CH₃ | 4-Cl | H | |
| 1.739 | 5'-COOH | 2'-CH₃ | 4-CN | H | |
| 1.740 | 5'-COOH | 2'-CH₃ | 4-CH₃ | H | |
| 1.741 | 5'-COOH | 2'-CH₃ | 4-CF₃ | H | |
| 1.742 | 5'-COOH | 2'-CH₃ | 4-OCF₃ | H | |

TABLE 1-continued

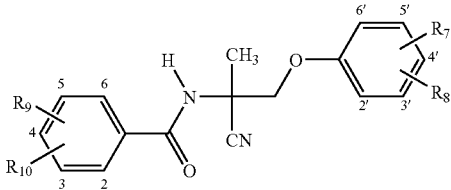

| No. | R7 | R8 | R9 | R10 | Phys. data |
|---|---|---|---|---|---|
| 1.743 | 5'-COOH | 2'-CH3 | 4-SCF3 | H | |
| 1.744 | 5'-COOH | 2'-CH3 | 4-S(O)CF3 | H | |
| 1.745 | 5'-COOH | 2'-CH3 | 4-S(O)2CF3 | H | |
| 1.746 | 5'-COOH | 2'-CH3 | 2-F | H | |
| 1.747 | 5'-COOH | 2'-CH3 | 2-Cl | H | |
| 1.748 | 5'-COOH | 2'-CH3 | 2-CN | H | |
| 1.749 | 5'-COOH | 2'-CH3 | 2-CH3 | H | |
| 1.750 | 5'-COOH | 2'-CH3 | 2-CF3 | H | |
| 1.751 | 5'-COOH | 2'-CH3 | 2-OCF3 | H | |
| 1.752 | 5'-COOH | 2'-CH3 | 2-SCF3 | H | |
| 1.753 | 5'-COOH | 2'-CH3 | 2-S(O)CF3 | H | |
| 1.754 | 5'-COOH | 2'-CH3 | 2-S(O)2CF3 | H | |
| 1.755 | 5'-COOH | 2'-CH3 | H | 4-NH2 | |
| 1.756 | 5'-COOH | 2'-CH3 | H | 4-COOH | |
| 1.757 | 5'-COOH | 2'-CH3 | H | 4-CONH2 | |
| 1.758 | 5'-COOH | 2'-CH3 | H | 4-CSNH2 | |
| 1.759 | 5'-COOH | 2'-CH3 | H | 4-NHCONH2 | |
| 1.760 | 5'-COOH | 2'-CH3 | H | 4-NHCSNH2 | |
| 1.761 | 5'-COOH | 2'-CH3 | H | 4-OCSNH2 | |
| 1.762 | 5'-COOH | 2'-CH3 | H | 3-OC(F2)O-4 | |
| 1.763 | 5'-COOH | 2'-CH3 | H | 3-SC(F2)S-4 | |
| 1.764 | 5'-COOH | 2'-CH3 | 2-F | 4-NH2 | |
| 1.765 | 5'-COOH | 2'-CH3 | 2-Cl | 4-COOH | |
| 1.766 | 5'-COOH | 2'-CH3 | 2-CN | 4-CONH2 | |
| 1.767 | 5'-COOH | 2'-CH3 | 2-CH3 | 4-CSNH2 | |
| 1.768 | 5'-COOH | 2'-CH3 | 2-CF3 | 4-NHCONH2 | |
| 1.769 | 5'-COOH | 2'-CH3 | 2-OCF3 | 4-NHCSNH2 | |
| 1.770 | 5'-COOH | 2'-CH3 | 2-SCF3 | 4-OCSNH2 | |
| 1.771 | 5'-COOH | 2'-CF3 | H | H | |
| 1.772 | 5'-COOH | 2'-CF3 | 4-F | H | |
| 1.773 | 5'-COOH | 2'-CF3 | 4-Cl | H | |
| 1.774 | 5'-COOH | 2'-CF3 | 4-CN | H | |
| 1.775 | 5'-COOH | 2'-CF3 | 4-CH3 | H | |
| 1.776 | 5'-COOH | 2'-CF3 | 4-CF3 | H | |
| 1.777 | 5'-COOH | 2'-CF3 | 4-OCF3 | H | m.p. 211-5° |
| 1.778 | 5'-COOH | 2'-CF3 | 4-SCF3 | H | |
| 1.779 | 5'-COOH | 2'-CF3 | 4-S(O)CF3 | H | |
| 1.780 | 5'-COOH | 2'-CF3 | 4-S(O)2CF3 | H | |
| 1.781 | 5'-COOH | 2'-CF3 | 2-F | H | |
| 1.782 | 5'-COOH | 2'-CF3 | 2-Cl | H | |
| 1.783 | 5'-COOH | 2'-CF3 | 2-CN | H | |
| 1.784 | 5'-COOH | 2'-CF3 | 2-CH3 | H | |
| 1.785 | 5'-COOH | 2'-CF3 | 2-CF3 | H | |
| 1.786 | 5'-COOH | 2'-CF3 | 2-OCF3 | H | |
| 1.787 | 5'-COOH | 2'-CF3 | 2-SCF3 | H | |
| 1.788 | 5'-COOH | 2'-CF3 | 2-S(O)CF3 | H | |
| 1.789 | 5'-COOH | 2'-CF3 | 2-S(O)2CF3 | H | |
| 1.790 | 5'-COOH | 2'-CF3 | H | 4-NH2 | |
| 1.791 | 5'-COOH | 2'-CF3 | H | 4-COOH | |
| 1.792 | 5'-COOH | 2'-CF3 | H | 4-CONH2 | |
| 1.793 | 5'-COOH | 2'-CF3 | H | 4-CSNH2 | |
| 1.794 | 5'-COOH | 2'-CF3 | H | 4-NHCONH2 | |
| 1.795 | 5'-COOH | 2'-CF3 | H | 4-NHCSNH2 | |
| 1.796 | 5'-COOH | 2'-CF3 | H | 4-OCSNH2 | |
| 1.797 | 5'-COOH | 2'-CF3 | H | 3-OC(F2)O-4 | |
| 1.798 | 5'-COOH | 2'-CF3 | H | 3-SC(F2)S-4 | |
| 1.799 | 5'-COOH | 2'-CF3 | 2-F | 4-NH2 | |
| 1.800 | 5'-COOH | 2'-CF3 | 2-Cl | 4-COOH | |
| 1.801 | 5'-COOH | 2'-CF3 | 2-CN | 4-CONH2 | |
| 1.802 | 5'-COOH | 2'-CF3 | 2-CH3 | 4-CSNH2 | |
| 1.803 | 5'-COOH | 2'-CF3 | 2-CF3 | 4-NHCONH2 | |
| 1.804 | 5'-COOH | 2'-CF3 | 2-OCF3 | 4-NHCSNH2 | |
| 1.805 | 5'-COOH | 2'-CF3 | 2-SCF3 | 4-OCSNH2 | |
| 1.806 | 5'-COOH | 2'-OCF3 | H | H | |
| 1.807 | 5'-COOH | 2'-OCF3 | 4-F | H | |
| 1.808 | 5'-COOH | 2'-OCF3 | 4-Cl | H | |

TABLE 1-continued

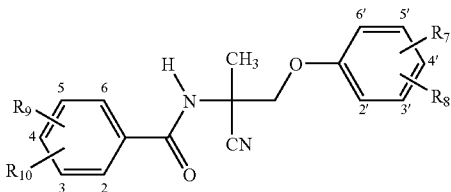

| No. | $R_7$ | $R_8$ | $R_9$ | $R_{10}$ | Phys. data |
|---|---|---|---|---|---|
| 1.809 | 5'-COOH | 2'-OCF$_3$ | 4-CN | H | |
| 1.810 | 5'-COOH | 2'-OCF$_3$ | 4-CH$_3$ | H | |
| 1.811 | 5'-COOH | 2'-OCF$_3$ | 4-CF$_3$ | H | |
| 1.812 | 5'-COOH | 2'-OCF$_3$ | 4-OCF$_3$ | H | |
| 1.813 | 5'-COOH | 2'-OCF$_3$ | 4-SCF$_3$ | H | |
| 1.814 | 5'-COOH | 2'-OCF$_3$ | 4-S(O)CF$_3$ | H | |
| 1.815 | 5'-COOH | 2'-OCF$_3$ | 4-S(O)$_2$CF$_3$ | H | |
| 1.816 | 5'-COOH | 2'-OCF$_3$ | 2-F | H | |
| 1.817 | 5'-COOH | 2'-OCF$_3$ | 2-Cl | H | |
| 1.818 | 5'-COOH | 2'-OCF$_3$ | 2-CN | H | |
| 1.819 | 5'-COOH | 2'-OCF$_3$ | 2-CH$_3$ | H | |
| 1.820 | 5'-COOH | 2'-OCF$_3$ | 2-CF$_3$ | H | |
| 1.821 | 5'-COOH | 2'-OCF$_3$ | 2-OCF$_3$ | H | |
| 1.822 | 5'-COOH | 2'-OCF$_3$ | 2-SCF$_3$ | H | |
| 1.823 | 5'-COOH | 2'-OCF$_3$ | 2-S(O)CF$_3$ | H | |
| 1.824 | 5'-COOH | 2'-OCF$_3$ | 2-S(O)$_2$CF$_3$ | H | |
| 1.825 | 5'-COOH | 2'-OCF$_3$ | H | 4-NH$_2$ | |
| 1.826 | 5'-COOH | 2'-OCF$_3$ | H | 4-COOH | |
| 1.827 | 5'-COOH | 2'-OCF$_3$ | H | 4-CONH$_2$ | |
| 1.828 | 5'-COOH | 2'-OCF$_3$ | H | 4-CSNH$_2$ | |
| 1.829 | 5'-COOH | 2'-OCF$_3$ | H | 4-NHCONH$_2$ | |
| 1.830 | 5'-COOH | 2'-OCF$_3$ | H | 4-NHCSNH$_2$ | |
| 1.831 | 5'-COOH | 2'-OCF$_3$ | H | 4-OCSNH$_2$ | |
| 1.832 | 5'-COOH | 2'-OCF$_3$ | H | 3-OC(F$_2$)O-4 | |
| 1.833 | 5'-COOH | 2'-OCF$_3$ | H | 3-SC(F$_2$)S-4 | |
| 1.834 | 5'-COOH | 2'-OCF$_3$ | 2-F | 4-NH$_2$ | |
| 1.835 | 5'-COOH | 2'-OCF$_3$ | 2-Cl | 4-COOH | |
| 1.836 | 5'-COOH | 2'-OCF$_3$ | 2-CN | 4-CONH$_2$ | |
| 1.837 | 5'-COOH | 2'-OCF$_3$ | 2-CH$_3$ | 4-CSNH$_2$ | |
| 1.838 | 5'-COOH | 2'-OCF$_3$ | 2-CF$_3$ | 4-NHCONH$_2$ | |
| 1.839 | 5'-COOH | 2'-OCF$_3$ | 2-OCF$_3$ | 4-NHCSNH$_2$ | |
| 1.840 | 5'-COOH | 2'-OCF$_3$ | 2-SCF$_3$ | 4-OCSNH$_2$ | |
| 1.841 | 5'-COOH | 2'-C$_6$H$_5$ | H | H | |
| 1.842 | 5'-COOH | 2'-C$_6$H$_5$ | 4-F | H | |
| 1.843 | 5'-COOH | 2'-C$_6$H$_5$ | 4-Cl | H | |
| 1.844 | 5'-COOH | 2'-C$_6$H$_5$ | 4-CN | H | |
| 1.845 | 5'-COOH | 2'-C$_6$H$_5$ | 4-CH$_3$ | H | |
| 1.846 | 5'-COOH | 2'-C$_6$H$_5$ | 4-CF$_3$ | H | |
| 1.847 | 5'-COOH | 2'-C$_6$H$_5$ | 4-OCF$_3$ | H | |
| 1.848 | 5'-COOH | 2'-C$_6$H$_5$ | 4-SCF$_3$ | H | |
| 1.849 | 5'-COOH | 2'-C$_6$H$_5$ | 4-S(O)CF$_3$ | H | |
| 1.850 | 5'-COOH | 2'-C$_6$H$_5$ | 4-S(O)$_2$CF$_3$ | H | |
| 1.851 | 5'-COOH | 2'-C$_6$H$_5$ | 2-F | H | |
| 1.852 | 5'-COOH | 2'-C$_6$H$_5$ | 2-Cl | H | |
| 1.853 | 5'-COOH | 2'-C$_6$H$_5$ | 2-CN | H | |
| 1.854 | 5'-COOH | 2'-C$_6$H$_5$ | 2-CH$_3$ | H | |
| 1.855 | 5'-COOH | 2'-C$_6$H$_5$ | 2-CF$_3$ | H | |
| 1.856 | 5'-COOH | 2'-C$_6$H$_5$ | 2-OCF$_3$ | H | |
| 1.857 | 5'-COOH | 2'-C$_6$H$_5$ | 2-SCF$_3$ | H | |
| 1.858 | 5'-COOH | 2'-C$_6$H$_5$ | 2-S(O)CF$_3$ | H | |
| 1.859 | 5'-COOH | 2'-C$_6$H$_5$ | 2-S(O)$_2$CF$_3$ | H | |
| 1.860 | 5'-COOH | 2'-C$_6$H$_5$ | H | 4-NH$_2$ | |
| 1.861 | 5'-COOH | 2'-C$_6$H$_5$ | H | 4-COOH | |
| 1.862 | 5'-COOH | 2'-C$_6$H$_5$ | H | 4-CONH$_2$ | |
| 1.863 | 5'-COOH | 2'-C$_6$H$_5$ | H | 4-CSNH$_2$ | |
| 1.864 | 5'-COOH | 2'-C$_6$H$_5$ | H | 4-NHCONH$_2$ | |
| 1.865 | 5'-COOH | 2'-C$_6$H$_5$ | H | 4-NHCSNH$_2$ | |
| 1.866 | 5'-COOH | 2'-C$_6$H$_5$ | H | 4-OCSNH$_2$ | |
| 1.867 | 5'-COOH | 2'-C$_6$H$_5$ | H | 3-OC(F$_2$)O-4 | |
| 1.868 | 5'-COOH | 2'-C$_6$H$_5$ | H | 3-SC(F$_2$)S-4 | |
| 1.869 | 5'-COOH | 2'-C$_6$H$_5$ | 2-F | 4-NH$_2$ | |
| 1.870 | 5'-COOH | 2'-C$_6$H$_5$ | 2-Cl | 4-COOH | |
| 1.871 | 5'-COOH | 2'-C$_6$H$_5$ | 2-CN | 4-CONH$_2$ | |
| 1.872 | 5'-COOH | 2'-C$_6$H$_5$ | 2-CH$_3$ | 4-CSNH$_2$ | |
| 1.873 | 5'-COOH | 2'-C$_6$H$_5$ | 2-CF$_3$ | 4-NHCONH$_2$ | |
| 1.874 | 5'-COOH | 2'-C$_6$H$_5$ | 2-OCF$_3$ | 4-NHCSNH$_2$ | |

TABLE 1-continued

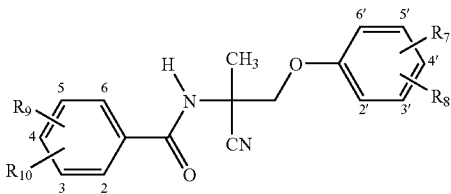

| No. | R_7 | R_8 | R_9 | R_10 | Phys. data |
|---|---|---|---|---|---|
| 1.875 | 5'-COOH | 2'-C_6H_5 | 2-SCF_3 | 4-OCSNH_2 | |
| 1.876 | 5'-COOH | 2'-(C_6H_4-4-Cl) | H | H | |
| 1.877 | 5'-COOH | 2'-(C_6H_4-4-Cl) | 4-F | H | |
| 1.878 | 5'-COOH | 2'-(C_6H_4-4-Cl) | 4-Cl | H | |
| 1.879 | 5'-COOH | 2'-(C_6H_4-4-Cl) | 4-CN | H | |
| 1.880 | 5'-COOH | 2'-(C_6H_4-4-Cl) | 4-CH_3 | H | |
| 1.881 | 5'-COOH | 2'-(C_6H_4-4-Cl) | 4-CF_3 | H | |
| 1.882 | 5'-COOH | 2'-(C_6H_4-4-Cl) | 4-OCF_3 | H | |
| 1.883 | 5'-COOH | 2'-(C_6H_4-4-Cl) | 4-SCF_3 | H | |
| 1.884 | 5'-COOH | 2'-(C_6H_4-4-Cl) | 4-S(O)CF_3 | H | |
| 1.885 | 5'-COOH | 2'-(C_6H_4-4-Cl) | 4-S(O)_2CF_3 | H | |
| 1.886 | 5'-COOH | 2'-(C_6H_4-4-Cl) | 2-F | H | |
| 1.887 | 5'-COOH | 2'-(C_6H_4-4-Cl) | 2-Cl | H | |
| 1.888 | 5'-COOH | 2'-(C_6H_4-4-Cl) | 2-CN | H | |
| 1.889 | 5'-COOH | 2'-(C_6H_4-4-Cl) | 2-CH_3 | H | |
| 1.890 | 5'-COOH | 2'-(C_6H_4-4-Cl) | 2-CF_3 | H | |
| 1.891 | 5'-COOH | 2'-(C_6H_4-4-Cl) | 2-OCF_3 | H | |
| 1.892 | 5'-COOH | 2'-(C_6H_4-4-Cl) | 2-SCF_3 | H | |
| 1.893 | 5'-COOH | 2'-(C_6H_4-4-Cl) | 2-S(O)CF_3 | H | |
| 1.894 | 5'-COOH | 2'-(C_6H_4-4-Cl) | 2-S(O)_2CF_3 | H | |
| 1.895 | 5'-COOH | 2'-(C_6H_4-4-Cl) | H | 4-NH_2 | |
| 1.896 | 5'-COOH | 2'-(C_6H_4-4-Cl) | H | 4-COOH | |
| 1.897 | 5'-COOH | 2'-(C_6H_4-4-Cl) | H | 4-CONH_2 | |
| 1.898 | 5'-COOH | 2'-(C_6H_4-4-Cl) | H | 4-CSNH_2 | |
| 1.899 | 5'-COOH | 2'-(C_6H_4-4-Cl) | H | 4-NHCONH_2 | |
| 1.900 | 5'-COOH | 2'-(C_6H_4-4-Cl) | H | 4-NHCSNH_2 | |
| 1.901 | 5'-COOH | 2'-(C_6H_4-4-Cl) | H | 4-OCSNH_2 | |
| 1.902 | 5'-COOH | 2'-(C_6H_4-4-Cl) | H | 3-OC(F_2)O-4 | |
| 1.903 | 5'-COOH | 2'-(C_6H_4-4-Cl) | H | 3-SC(F_2)S-4 | |
| 1.904 | 5'-COOH | 2'-(C_6H_4-4-Cl) | 2-F | 4-NH_2 | |
| 1.905 | 5'-COOH | 2'-(C_6H_4-4-Cl) | 2-Cl | 4-COOH | |
| 1.906 | 5'-COOH | 2'-(C_6H_4-4-Cl) | 2-CN | 4-CONH_2 | |
| 1.907 | 5'-COOH | 2'-(C_6H_4-4-Cl) | 2-CH_3 | 4-CSNH_2 | |
| 1.908 | 5'-COOH | 2'-(C_6H_4-4-Cl) | 2-CF_3 | 4-NHCONH_2 | |
| 1.909 | 5'-COOH | 2'-(C_6H_4-4-Cl) | 2-OCF_3 | 4-NHCSNH_2 | |
| 1.910 | 5'-COOH | 2'-(C_6H_4-4-Cl) | 2-SCF_3 | 4-OCSNH_2 | |
| 1.911 | 5'-COOH | 2'-(C_6H_3-2,4-Cl_2) | H | H | |
| 1.912 | 5'-COOH | 2'-(C_6H_3-2,4-Cl_2) | 4-F | H | |
| 1.913 | 5'-COOH | 2'-(C_6H_3-2,4-Cl_2) | 4-Cl | H | |
| 1.914 | 5'-COOH | 2'-(C_6H_3-2,4-Cl_2) | 4-CN | H | |
| 1.915 | 5'-COOH | 2'-(C_6H_3-2,4-Cl_2) | 4-CH_3 | H | |
| 1.916 | 5'-COOH | 2'-(C_6H_3-2,4-Cl_2) | 4-CF_3 | H | |
| 1.917 | 5'-COOH | 2'-(C_6H_3-2,4-Cl_2) | 4-OCF_3 | H | |
| 1.918 | 5'-COOH | 2'-(C_6H_3-2,4-Cl_2) | 4-SCF_3 | H | |
| 1.919 | 5'-COOH | 2'-(C_6H_3-2,4-Cl_2) | 4-S(O)CF_3 | H | |
| 1.920 | 5'-COOH | 2'-(C_6H_3-2,4-Cl_2) | 4-S(O)_2CF_3 | H | |
| 1.921 | 5'-COOH | 2'-(C_6H_3-2,4-Cl_2) | 2-F | H | |
| 1.922 | 5'-COOH | 2'-(C_6H_3-2,4-Cl_2) | 2-Cl | H | |
| 1.923 | 5'-COOH | 2'-(C_6H_3-2,4-Cl_2) | 2-CN | H | |
| 1.924 | 5'-COOH | 2'-(C_6H_3-2,4-Cl_2) | 2-CH_3 | H | |
| 1.925 | 5'-COOH | 2'-(C_6H_3-2,4-Cl_2) | 2-CF_3 | H | |
| 1.926 | 5'-COOH | 2'-(C_6H_3-2,4-Cl_2) | 2-OCF_3 | H | |
| 1.927 | 5'-COOH | 2'-(C_6H_3-2,4-Cl_2) | 2-SCF_3 | H | |
| 1.928 | 5'-COOH | 2'-(C_6H_3-2,4-Cl_2) | 2-S(O)CF_3 | H | |
| 1.929 | 5'-COOH | 2'-(C_6H_3-2,4-Cl_2) | 2-S(O)_2CF_3 | H | |
| 1.930 | 5'-COOH | 2'-(C_6H_3-2,4-Cl_2) | H | 4-NH_2 | |
| 1.931 | 5'-COOH | 2'-(C_6H_3-2,4-Cl_2) | H | 4-COOH | |
| 1.932 | 5'-COOH | 2'-(C_6H_3-2,4-Cl_2) | H | 4-CONH_2 | |
| 1.933 | 5'-COOH | 2'-(C_6H_3-2,4-Cl_2) | H | 4-CSNH_2 | |
| 1.934 | 5'-COOH | 2'-(C_6H_3-2,4-Cl_2) | H | 4-NHCONH_2 | |
| 1.935 | 5'-COOH | 2'-(C_6H_3-2,4-Cl_2) | H | 4-NHCSNH_2 | |
| 1.936 | 5'-COOH | 2'-(C_6H_3-2,4-Cl_2) | H | 4-OCSNH_2 | |
| 1.937 | 5'-COOH | 2'-(C_6H_3-2,4-Cl_2) | H | 3-OC(F_2)O-4 | |
| 1.938 | 5'-COOH | 2'-(C_6H_3-2,4-Cl_2) | H | 3-SC(F_2)S-4 | |
| 1.939 | 5'-COOH | 2'-(C_6H_3-2,4-Cl_2) | 2-F | 4-NH_2 | |
| 1.940 | 5'-COOH | 2'-(C_6H_3-2,4-Cl_2) | 2-Cl | 4-COOH | |

TABLE 1-continued

| No. | $R_7$ | $R_8$ | $R_9$ | $R_{10}$ | Phys. data |
|---|---|---|---|---|---|
| 1.941 | 5'-COOH | 2'-($C_6H_3$-2,4-$Cl_2$) | 2-CN | 4-$CONH_2$ | |
| 1.942 | 5'-COOH | 2'-($C_6H_3$-2,4-$Cl_2$) | 2-$CH_3$ | 4-$CSNH_2$ | |
| 1.943 | 5'-COOH | 2'-($C_6H_3$-2,4-$Cl_2$) | 2-$CF_3$ | 4-$NHCONH_2$ | |
| 1.944 | 5'-COOH | 2'-($C_6H_3$-2,4-$Cl_2$) | 2-$OCF_3$ | 4-$NHCSNH_2$ | |
| 1.945 | 5'-COOH | 2'-($C_6H_3$-2,4-$Cl_2$) | 2-$SCF_3$ | 4-$OCSNH_2$ | |
| 1.946 | 5'-$CONH_2$ | H | H | H | |
| 1.947 | 5'-$CONH_2$ | H | 4-F | H | |
| 1.948 | 5'-$CONH_2$ | H | 4-Cl | H | |
| 1.949 | 5'-$CONH_2$ | H | 4-CN | H | |
| 1.950 | 5'-$CONH_2$ | H | 4-$CH_3$ | H | |
| 1.951 | 5'-$CONH_2$ | H | 4-$CF_3$ | H | |
| 1.952 | 5'-$CONH_2$ | H | 4-$OCF_3$ | H | |
| 1.953 | 5'-$CONH_2$ | H | 4-$SCF_3$ | H | |
| 1.954 | 5'-$CONH_2$ | H | 4-$S(O)CF_3$ | H | |
| 1.955 | 5'-$CONH_2$ | H | 4-$S(O)_2CF_3$ | H | |
| 1.956 | 5'-$CONH_2$ | H | 2-F | H | |
| 1.957 | 5'-$CONH_2$ | H | 2-Cl | H | |
| 1.958 | 5'-$CONH_2$ | H | 2-CN | H | |
| 1.959 | 5'-$CONH_2$ | H | 2-$CH_3$ | H | |
| 1.960 | 5'-$CONH_2$ | H | 2-$CF_3$ | H | |
| 1.961 | 5'-$CONH_2$ | H | 2-$OCF_3$ | H | |
| 1.962 | 5'-$CONH_2$ | H | 2-$SCF_3$ | H | |
| 1.963 | 5'-$CONH_2$ | H | 2-$S(O)CF_3$ | H | |
| 1.964 | 5'-$CONH_2$ | H | 2-$S(O)_2CF_3$ | H | |
| 1.965 | 5'-$CONH_2$ | H | H | 4-$NH_2$ | |
| 1.966 | 5'-$CONH_2$ | H | H | 4-COOH | |
| 1.967 | 5'-$CONH_2$ | H | H | 4-$CONH_2$ | |
| 1.968 | 5'-$CONH_2$ | H | H | 4-$CSNH_2$ | |
| 1.969 | 5'-$CONH_2$ | H | H | 4-$NHCONH_2$ | |
| 1.970 | 5'-$CONH_2$ | H | H | 4-$NHCSNH_2$ | |
| 1.971 | 5'-$CONH_2$ | H | H | 4-$OCSNH_2$ | |
| 1.972 | 5'-$CONH_2$ | H | H | 3-$OC(F_2)O$-4 | |
| 1.973 | 5'-$CONH_2$ | H | H | 3-$SC(F_2)S$-4 | |
| 1.974 | 5'-$CONH_2$ | H | 2-F | 4-$NH_2$ | |
| 1.975 | 5'-$CONH_2$ | H | 2-Cl | 4-COOH | |
| 1.976 | 5'-$CONH_2$ | H | 2-CN | 4-$CONH_2$ | |
| 1.977 | 5'-$CONH_2$ | H | 2-$CH_3$ | 4-$CSNH_2$ | |
| 1.978 | 5'-$CONH_2$ | H | 2-$CF_3$ | 4-$NHCONH_2$ | |
| 1.979 | 5'-$CONH_2$ | H | 2-$OCF_3$ | 4-$NHCSNH_2$ | |
| 1.980 | 5'-$CONH_2$ | H | 2-$SCF_3$ | 4-$OCSNH_2$ | |
| 1.981 | 5'-$CONH_2$ | 2'-CN | H | H | |
| 1.982 | 5'-$CONH_2$ | 2'-CN | 4-F | H | |
| 1.983 | 5'-$CONH_2$ | 2'-CN | 4-Cl | H | |
| 1.984 | 5'-$CONH_2$ | 2'-CN | 4-CN | H | |
| 1.985 | 5'-$CONH_2$ | 2'-CN | 4-$CH_3$ | H | |
| 1.986 | 5'-$CONH_2$ | 2'-CN | 4-$CF_3$ | H | |
| 1.987 | 5'-$CONH_2$ | 2'-CN | 4-$OCF_3$ | H | |
| 1.988 | 5'-$CONH_2$ | 2'-CN | 4-$SCF_3$ | H | |
| 1.989 | 5'-$CONH_2$ | 2'-CN | 4-$S(O)CF_3$ | H | |
| 1.990 | 5'-$CONH_2$ | 2'-CN | 4-$S(O)_2CF_3$ | H | |
| 1.991 | 5'-$CONH_2$ | 2'-CN | 2-F | H | |
| 1.992 | 5'-$CONH_2$ | 2'-CN | 2-Cl | H | |
| 1.993 | 5'-$CONH_2$ | 2'-CN | 2-CN | H | |
| 1.994 | 5'-$CONH_2$ | 2'-CN | 2-$CH_3$ | H | |
| 1.995 | 5'-$CONH_2$ | 2'-CN | 2-$CF_3$ | H | |
| 1.996 | 5'-$CONH_2$ | 2'-CN | 2-$OCF_3$ | H | |
| 1.997 | 5'-$CONH_2$ | 2'-CN | 2-$SCF_3$ | H | |
| 1.998 | 5'-$CONH_2$ | 2'-CN | 2-$S(O)CF_3$ | H | |
| 1.999 | 5'-$CONH_2$ | 2'-CN | 2-$S(O)_2CF_3$ | H | |
| 1.1000 | 5'-$CONH_2$ | 2'-CN | H | 4-$NH_2$ | |
| 1.1001 | 5'-$CONH_2$ | 2'-CN | H | 4-COOH | |
| 1.1002 | 5'-$CONH_2$ | 2'-CN | H | 4-$CONH_2$ | |
| 1.1003 | 5'-$CONH_2$ | 2'-CN | H | 4-$CSNH_2$ | |
| 1.1004 | 5'-$CONH_2$ | 2'-CN | H | 4-$NHCONH_2$ | |
| 1.1005 | 5'-$CONH_2$ | 2'-CN | H | 4-$NHCSNH_2$ | |
| 1.1006 | 5'-$CONH_2$ | 2'-CN | H | 4-$OCSNH_2$ | |

TABLE 1-continued

| No. | R₇ | R₈ | R₉ | R₁₀ | Phys. data |
|---|---|---|---|---|---|
| 1.1007 | 5'-CONH₂ | 2'-CN | H | 3-OC(F₂)O-4 | |
| 1.1008 | 5'-CONH₂ | 2'-CN | H | 3-SC(F₂)S-4 | |
| 1.1009 | 5'-CONH₂ | 2'-CN | 2-F | 4-NH₂ | |
| 1.1010 | 5'-CONH₂ | 2'-CN | 2-Cl | 4-COOH | |
| 1.1011 | 5'-CONH₂ | 2'-CN | 2-CN | 4-CONH₂ | |
| 1.1012 | 5'-CONH₂ | 2'-CN | 2-CH₃ | 4-CSNH₂ | |
| 1.1013 | 5'-CONH₂ | 2'-CN | 2-CF₃ | 4-NHCONH₂ | |
| 1.1014 | 5'-CONH₂ | 2'-CN | 2-OCF₃ | 4-NHCSNH₂ | |
| 1.1015 | 5'-CONH₂ | 2'-CN | 2-SCF₃ | 4-OCSNH₂ | |
| 1.1016 | 5'-CONH₂ | 2'-CH₃ | H | H | |
| 1.1017 | 5'-CONH₂ | 2'-CH₃ | 4-F | H | |
| 1.1018 | 5'-CONH₂ | 2'-CH₃ | 4-Cl | H | |
| 1.1019 | 5'-CONH₂ | 2'-CH₃ | 4-CN | H | |
| 1.1020 | 5'-CONH₂ | 2'-CH₃ | 4-CH₃ | H | |
| 1.1021 | 5'-CONH₂ | 2'-CH₃ | 4-CF₃ | H | |
| 1.1022 | 5'-CONH₂ | 2'-CH₃ | 4-OCF₃ | H | |
| 1.1023 | 5'-CONH₂ | 2'-CH₃ | 4-SCF₃ | H | |
| 1.1024 | 5'-CONH₂ | 2'-CH₃ | 4-S(O)CF₃ | H | |
| 1.1025 | 5'-CONH₂ | 2'-CH₃ | 4-S(O)₂CF₃ | H | |
| 1.1026 | 5'-CONH₂ | 2'-CH₃ | 2-F | H | |
| 1.1027 | 5'-CONH₂ | 2'-CH₃ | 2-Cl | H | |
| 1.1028 | 5'-CONH₂ | 2'-CH₃ | 2-CN | H | |
| 1.1029 | 5'-CONH₂ | 2'-CH₃ | 2-CH₃ | H | |
| 1.1030 | 5'-CONH₂ | 2'-CH₃ | 2-CF₃ | H | |
| 1.1031 | 5'-CONH₂ | 2'-CH₃ | 2-OCF₃ | H | |
| 1.1032 | 5'-CONH₂ | 2'-CH₃ | 2-SCF₃ | H | |
| 1.1033 | 5'-CONH₂ | 2'-CH₃ | 2-S(O)CF₃ | H | |
| 1.1034 | 5'-CONH₂ | 2'-CH₃ | 2-S(O)₂CF₃ | H | |
| 1.1035 | 5'-CONH₂ | 2'-CH₃ | H | 4-NH₂ | |
| 1.1036 | 5'-CONH₂ | 2'-CH₃ | H | 4-COOH | |
| 1.1037 | 5'-CONH₂ | 2'-CH₃ | H | 4-CONH₂ | |
| 1.1038 | 5'-CONH₂ | 2'-CH₃ | H | 4-CSNH₂ | |
| 1.1039 | 5'-CONH₂ | 2'-CH₃ | H | 4-NHCONH₂ | |
| 1.1040 | 5'-CONH₂ | 2'-CH₃ | H | 4-NHCSNH₂ | |
| 1.1041 | 5'-CONH₂ | 2'-CH₃ | H | 4-OCSNH₂ | |
| 1.1042 | 5'-CONH₂ | 2'-CH₃ | H | 3-OC(F₂)O-4 | |
| 1.1043 | 5'-CONH₂ | 2'-CH₃ | H | 3-SC(F₂)S-4 | |
| 1.1044 | 5'-CONH₂ | 2'-CH₃ | 2-F | 4-NH₂ | |
| 1.1045 | 5'-CONH₂ | 2'-CH₃ | 2-Cl | 4-COOH | |
| 1.1046 | 5'-CONH₂ | 2'-CH₃ | 2-CN | 4-CONH₂ | |
| 1.1047 | 5'-CONH₂ | 2'-CH₃ | 2-CH₃ | 4-CSNH₂ | |
| 1.1048 | 5'-CONH₂ | 2'-CH₃ | 2-CF₃ | 4-NHCONH₂ | |
| 1.1049 | 5'-CONH₂ | 2'-CH₃ | 2-OCF₃ | 4-NHCSNH₂ | |
| 1.1050 | 5'-CONH₂ | 2'-CH₃ | 2-SCF₃ | 4-OCSNH₂ | |
| 1.1051 | 5'-CONH₂ | 2'-CF₃ | H | H | |
| 1.1052 | 5'-CONH₂ | 2'-CF₃ | 4-F | H | |
| 1.1053 | 5'-CONH₂ | 2'-CF₃ | 4-Cl | H | |
| 1.1054 | 5'-CONH₂ | 2'-CF₃ | 4-CN | H | |
| 1.1055 | 5'-CONH₂ | 2'-CF₃ | 4-CH₃ | H | |
| 1.1056 | 5'-CONH₂ | 2'-CF₃ | 4-CF₃ | H | |
| 1.1057 | 5'-CONH₂ | 2'-CF₃ | 4-OCF₃ | H | m.p. 169-73° |
| 1.1058 | 5'-CONH₂ | 2'-CF₃ | 4-SCF₃ | H | m.p. 161-5° |
| 1.1059 | 5'-CONH₂ | 2'-CF₃ | 4-S(O)CF₃ | H | |
| 1.1060 | 5'-CONH₂ | 2'-CF₃ | 4-S(O)₂CF₃ | H | |
| 1.1061 | 5'-CONH₂ | 2'-CF₃ | 2-F | H | |
| 1.1062 | 5'-CONH₂ | 2'-CF₃ | 2-Cl | H | |
| 1.1063 | 5'-CONH₂ | 2'-CF₃ | 2-CN | H | |
| 1.1064 | 5'-CONH₂ | 2'-CF₃ | 2-CH₃ | H | |
| 1.1065 | 5'-CONH₂ | 2'-CF₃ | 2-CF₃ | H | |
| 1.1066 | 5'-CONH₂ | 2'-CF₃ | 2-OCF₃ | H | |
| 1.1067 | 5'-CONH₂ | 2'-CF₃ | 2-SCF₃ | H | |
| 1.1068 | 5'-CONH₂ | 2'-CF₃ | 2-S(O)CF₃ | H | |
| 1.1069 | 5'-CONH₂ | 2'-CF₃ | 2-S(O)₂CF₃ | H | |
| 1.1070 | 5'-CONH₂ | 2'-CF₃ | H | 4-NH₂ | |
| 1.1071 | 5'-CONH₂ | 2'-CF₃ | H | 4-COOH | |
| 1.1072 | 5'-CONH₂ | 2'-CF₃ | H | 4-CONH₂ | |

TABLE 1-continued

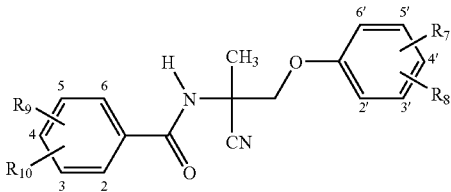

| No. | $R_7$ | $R_8$ | $R_9$ | $R_{10}$ | Phys. data |
|---|---|---|---|---|---|
| 1.1073 | 5'-CONH$_2$ | 2'-CF$_3$ | H | 4-CSNH$_2$ | |
| 1.1074 | 5'-CONH$_2$ | 2'-CF$_3$ | H | 4-NHCONH$_2$ | |
| 1.1075 | 5'-CONH$_2$ | 2'-CF$_3$ | H | 4-NHCSNH$_2$ | |
| 1.1076 | 5'-CONH$_2$ | 2'-CF$_3$ | H | 4-OCSNH$_2$ | |
| 1.1077 | 5'-CONH$_2$ | 2'-CF$_3$ | H | 3-OC(F$_2$)O-4 | |
| 1.1078 | 5'-CONH$_2$ | 2'-CF$_3$ | H | 3-SC(F$_2$)S-4 | |
| 1.1079 | 5'-CONH$_2$ | 2'-CF$_3$ | 2-F | 4-NH$_2$ | |
| 1.1080 | 5'-CONH$_2$ | 2'-CF$_3$ | 2-Cl | 4-COOH | |
| 1.1081 | 5'-CONH$_2$ | 2'-CF$_3$ | 2-CN | 4-CONH$_2$ | |
| 1.1082 | 5'-CONH$_2$ | 2'-CF$_3$ | 2-CH$_3$ | 4-CSNH$_2$ | |
| 1.1083 | 5'-CONH$_2$ | 2'-CF$_3$ | 2-CF$_3$ | 4-NHCONH$_2$ | |
| 1.1084 | 5'-CONH$_2$ | 2'-CF$_3$ | 2-OCF$_3$ | 4-NHCSNH$_2$ | |
| 1.1085 | 5'-CONH$_2$ | 2'-CF$_3$ | 2-SCF$_3$ | 4-OCSNH$_2$ | |
| 1.1086 | 5'-CONH$_2$ | 2'-OCF$_3$ | H | H | |
| 1.1087 | 5'-CONH$_2$ | 2'-OCF$_3$ | 4-F | H | |
| 1.1088 | 5'-CONH$_2$ | 2'-OCF$_3$ | 4-Cl | H | |
| 1.1089 | 5'-CONH$_2$ | 2'-OCF$_3$ | 4-CN | H | |
| 1.1090 | 5'-CONH$_2$ | 2'-OCF$_3$ | 4-CH$_3$ | H | |
| 1.1091 | 5'-CONH$_2$ | 2'-OCF$_3$ | 4-CF$_3$ | H | |
| 1.1092 | 5'-CONH$_2$ | 2'-OCF$_3$ | 4-OCF$_3$ | H | |
| 1.1093 | 5'-CONH$_2$ | 2'-OCF$_3$ | 4-SCF$_3$ | H | |
| 1.1094 | 5'-CONH$_2$ | 2'-OCF$_3$ | 4-S(O)CF$_3$ | H | |
| 1.1095 | 5'-CONH$_2$ | 2'-OCF$_3$ | 4-S(O)$_2$CF$_3$ | H | |
| 1.1096 | 5'-CONH$_2$ | 2'-OCF$_3$ | 2-F | H | |
| 1.1097 | 5'-CONH$_2$ | 2'-OCF$_3$ | 2-Cl | H | |
| 1.1098 | 5'-CONH$_2$ | 2'-OCF$_3$ | 2-CN | H | |
| 1.1099 | 5'-CONH$_2$ | 2'-OCF$_3$ | 2-CH$_3$ | H | |
| 1.1100 | 5'-CONH$_2$ | 2'-OCF$_3$ | 2-CF$_3$ | H | |
| 1.1101 | 5'-CONH$_2$ | 2'-OCF$_3$ | 2-OCF$_3$ | H | |
| 1.1102 | 5'-CONH$_2$ | 2'-OCF$_3$ | 2-SCF$_3$ | H | |
| 1.1103 | 5'-CONH$_2$ | 2'-OCF$_3$ | 2-S(O)CF$_3$ | H | |
| 1.1104 | 5'-CONH$_2$ | 2'-OCF$_3$ | 2-S(O)$_2$CF$_3$ | H | |
| 1.1105 | 5'-CONH$_2$ | 2'-OCF$_3$ | H | 4-NH$_2$ | |
| 1.1106 | 5'-CONH$_2$ | 2'-OCF$_3$ | H | 4-COOH | |
| 1.1107 | 5'-CONH$_2$ | 2'-OCF$_3$ | H | 4-CONH$_2$ | |
| 1.1108 | 5'-CONH$_2$ | 2'-OCF$_3$ | H | 4-CSNH$_2$ | |
| 1.1109 | 5'-CONH$_2$ | 2'-OCF$_3$ | H | 4-NHCONH$_2$ | |
| 1.1110 | 5'-CONH$_2$ | 2'-OCF$_3$ | H | 4-NHCSNH$_2$ | |
| 1.1111 | 5'-CONH$_2$ | 2'-OCF$_3$ | H | 4-OCSNH$_2$ | |
| 1.1112 | 5'-CONH$_2$ | 2'-OCF$_3$ | H | 3-OC(F$_2$)O-4 | |
| 1.1113 | 5'-CONH$_2$ | 2'-OCF$_3$ | H | 3-SC(F$_2$)S-4 | |
| 1.1114 | 5'-CONH$_2$ | 2'-OCF$_3$ | 2-F | 4-NH$_2$ | |
| 1.1115 | 5'-CONH$_2$ | 2'-OCF$_3$ | 2-Cl | 4-COOH | |
| 1.1116 | 5'-CONH$_2$ | 2'-OCF$_3$ | 2-CN | 4-CONH$_2$ | |
| 1.1117 | 5'-CONH$_2$ | 2'-OCF$_3$ | 2-CH$_3$ | 4-CSNH$_2$ | |
| 1.1118 | 5'-CONH$_2$ | 2'-OCF$_3$ | 2-CF$_3$ | 4-NHCONH$_2$ | |
| 1.1119 | 5'-CONH$_2$ | 2'-OCF$_3$ | 2-OCF$_3$ | 4-NHCSNH$_2$ | |
| 1.1120 | 5'-CONH$_2$ | 2'-OCF$_3$ | 2-SCF$_3$ | 4-OCSNH$_2$ | |
| 1.1121 | 5'-CONH$_2$ | 2'-C$_6$H$_5$ | H | H | |
| 1.1122 | 5'-CONH$_2$ | 2'-C$_6$H$_5$ | 4-F | H | |
| 1.1123 | 5'-CONH$_2$ | 2'-C$_6$H$_5$ | 4-Cl | H | |
| 1.1124 | 5'-CONH$_2$ | 2'-C$_6$H$_5$ | 4-CN | H | |
| 1.1125 | 5'-CONH$_2$ | 2'-C$_6$H$_5$ | 4-CH$_3$ | H | |
| 1.1126 | 5'-CONH$_2$ | 2'-C$_6$H$_5$ | 4-CF$_3$ | H | |
| 1.1127 | 5'-CONH$_2$ | 2'-C$_6$H$_5$ | 4-OCF$_3$ | H | |
| 1.1128 | 5'-CONH$_2$ | 2'-C$_6$H$_5$ | 4-SCF$_3$ | H | |
| 1.1129 | 5'-CONH$_2$ | 2'-C$_6$H$_5$ | 4-S(O)CF$_3$ | H | |
| 1.1130 | 5'-CONH$_2$ | 2'-C$_6$H$_5$ | 4-S(O)$_2$CF$_3$ | H | |
| 1.1131 | 5'-CONH$_2$ | 2'-C$_6$H$_5$ | 2-F | H | |
| 1.1132 | 5'-CONH$_2$ | 2'-C$_6$H$_5$ | 2-Cl | H | |
| 1.1133 | 5'-CONH$_2$ | 2'-C$_6$H$_5$ | 2-CN | H | |
| 1.1134 | 5'-CONH$_2$ | 2'-C$_6$H$_5$ | 2-CH$_3$ | H | |
| 1.1135 | 5'-CONH$_2$ | 2'-C$_6$H$_5$ | 2-CF$_3$ | H | |
| 1.1136 | 5'-CONH$_2$ | 2'-C$_6$H$_5$ | 2-OCF$_3$ | H | |
| 1.1137 | 5'-CONH$_2$ | 2'-C$_6$H$_5$ | 2-SCF$_3$ | H | |
| 1.1138 | 5'-CONH$_2$ | 2'-C$_6$H$_5$ | 2-S(O)CF$_3$ | H | |

TABLE 1-continued

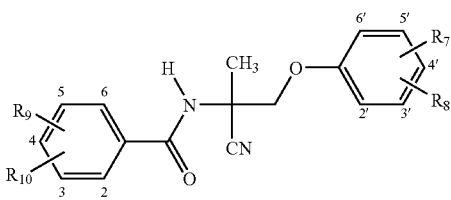

| No. | $R_7$ | $R_8$ | $R_9$ | $R_{10}$ | Phys. data |
|---|---|---|---|---|---|
| 1.1139 | 5'-CONH$_2$ | 2'-C$_6$H$_5$ | 2-S(O)$_2$CF$_3$ | H | |
| 1.1140 | 5'-CONH$_2$ | 2'-C$_6$H$_5$ | H | 4-NH$_2$ | |
| 1.1141 | 5'-CONH$_2$ | 2'-C$_6$H$_5$ | H | 4-COOH | |
| 1.1142 | 5'-CONH$_2$ | 2'-C$_6$H$_5$ | H | 4-CONH$_2$ | |
| 1.1143 | 5'-CONH$_2$ | 2'-C$_6$H$_5$ | H | 4-CSNH$_2$ | |
| 1.1144 | 5'-CONH$_2$ | 2'-C$_6$H$_5$ | H | 4-NHCONH$_2$ | |
| 1.1145 | 5'-CONH$_2$ | 2'-C$_6$H$_5$ | H | 4-NHCSNH$_2$ | |
| 1.1146 | 5'-CONH$_2$ | 2'-C$_6$H$_5$ | H | 4-OCSNH$_2$ | |
| 1.1147 | 5'-CONH$_2$ | 2'-C$_6$H$_5$ | H | 3-OC(F$_2$)O-4 | |
| 1.1148 | 5'-CONH$_2$ | 2'-C$_6$H$_5$ | H | 3-SC(F$_2$)S-4 | |
| 1.1149 | 5'-CONH$_2$ | 2'-C$_6$H$_5$ | 2-F | 4-NH$_2$ | |
| 1.1150 | 5'-CONH$_2$ | 2'-C$_6$H$_5$ | 2-Cl | 4-COOH | |
| 1.1151 | 5'-CONH$_2$ | 2'-C$_6$H$_5$ | 2-CN | 4-CONH$_2$ | |
| 1.1152 | 5'-CONH$_2$ | 2'-C$_6$H$_5$ | 2-CH$_3$ | 4-CSNH$_2$ | |
| 1.1153 | 5'-CONH$_2$ | 2'-C$_6$H$_5$ | 2-CF$_3$ | 4-NHCONH$_2$ | |
| 1.1154 | 5'-CONH$_2$ | 2'-C$_6$H$_5$ | 2-OCF$_3$ | 4-NHCSNH$_2$ | |
| 1.1155 | 5'-CONH$_2$ | 2'-C$_6$H$_5$ | 2-SCF$_3$ | 4-OCSNH$_2$ | |
| 1.1156 | 5'-CONH$_2$ | 2'-(C$_6$H$_4$-4-Cl) | H | H | |
| 1.1157 | 5'-CONH$_2$ | 2'-(C$_6$H$_4$-4-Cl) | 4-F | H | |
| 1.1158 | 5'-CONH$_2$ | 2'-(C$_6$H$_4$-4-Cl) | 4-Cl | H | |
| 1.1159 | 5'-CONH$_2$ | 2'-(C$_6$H$_4$-4-Cl) | 4-CN | H | |
| 1.1160 | 5'-CONH$_2$ | 2'-(C$_6$H$_4$-4-Cl) | 4-CH$_3$ | H | |
| 1.1161 | 5'-CONH$_2$ | 2'-(C$_6$H$_4$-4-Cl) | 4-CF$_3$ | H | |
| 1.1162 | 5'-CONH$_2$ | 2'-(C$_6$H$_4$-4-Cl) | 4-OCF$_3$ | H | |
| 1.1163 | 5'-CONH$_2$ | 2'-(C$_6$H$_4$-4-Cl) | 4-SCF$_3$ | H | |
| 1.1164 | 5'-CONH$_2$ | 2'-(C$_6$H$_4$-4-Cl) | 4-S(O)CF$_3$ | H | |
| 1.1165 | 5'-CONH$_2$ | 2'-(C$_6$H$_4$-4-Cl) | 4-S(O)$_2$CF$_3$ | H | |
| 1.1166 | 5'-CONH$_2$ | 2'-(C$_6$H$_4$-4-Cl) | 2-F | H | |
| 1.1167 | 5'-CONH$_2$ | 2'-(C$_6$H$_4$-4-Cl) | 2-Cl | H | |
| 1.1168 | 5'-CONH$_2$ | 2'-(C$_6$H$_4$-4-Cl) | 2-CN | H | |
| 1.1169 | 5'-CONH$_2$ | 2'-(C$_6$H$_4$-4-Cl) | 2-CH$_3$ | H | |
| 1.1170 | 5'-CONH$_2$ | 2'-(C$_6$H$_4$-4-Cl) | 2-CF$_3$ | H | |
| 1.1171 | 5'-CONH$_2$ | 2'-(C$_6$H$_4$-4-Cl) | 2-OCF$_3$ | H | |
| 1.1172 | 5'-CONH$_2$ | 2'-(C$_6$H$_4$-4-Cl) | 2-SCF$_3$ | H | |
| 1.1173 | 5'-CONH$_2$ | 2'-(C$_6$H$_4$-4-Cl) | 2-S(O)CF$_3$ | H | |
| 1.1174 | 5'-CONH$_2$ | 2'-(C$_6$H$_4$-4-Cl) | 2-S(O)$_2$CF$_3$ | H | |
| 1.1175 | 5'-CONH$_2$ | 2'-(C$_6$H$_4$-4-Cl) | H | 4-NH$_2$ | |
| 1.1176 | 5'-CONH$_2$ | 2'-(C$_6$H$_4$-4-Cl) | H | 4-COOH | |
| 1.1177 | 5'-CONH$_2$ | 2'-(C$_6$H$_4$-4-Cl) | H | 4-CONH$_2$ | |
| 1.1178 | 5'-CONH$_2$ | 2'-(C$_6$H$_4$-4-Cl) | H | 4-CSNH$_2$ | |
| 1.1179 | 5'-CONH$_2$ | 2'-(C$_6$H$_4$-4-Cl) | H | 4-NHCONH$_2$ | |
| 1.1180 | 5'-CONH$_2$ | 2'-(C$_6$H$_4$-4-Cl) | H | 4-NHCSNH$_2$ | |
| 1.1181 | 5'-CONH$_2$ | 2'-(C$_6$H$_4$-4-Cl) | H | 4-OCSNH$_2$ | |
| 1.1182 | 5'-CONH$_2$ | 2'-(C$_6$H$_4$-4-Cl) | H | 3-OC(F$_2$)O-4 | |
| 1.1183 | 5'-CONH$_2$ | 2'-(C$_6$H$_4$-4-Cl) | H | 3-SC(F$_2$)S-4 | |
| 1.1184 | 5'-CONH$_2$ | 2'-(C$_6$H$_4$-4-Cl) | 2-F | 4-NH$_2$ | |
| 1.1185 | 5'-CONH$_2$ | 2'-(C$_6$H$_4$-4-Cl) | 2-Cl | 4-COOH | |
| 1.1186 | 5'-CONH$_2$ | 2'-(C$_6$H$_4$-4-Cl) | 2-CN | 4-CONH$_2$ | |
| 1.1187 | 5'-CONH$_2$ | 2'-(C$_6$H$_4$-4-Cl) | 2-CH$_3$ | 4-CSNH$_2$ | |
| 1.1188 | 5'-CONH$_2$ | 2'-(C$_6$H$_4$-4-Cl) | 2-CF$_3$ | 4-NHCONH$_2$ | |
| 1.1189 | 5'-CONH$_2$ | 2'-(C$_6$H$_4$-4-Cl) | 2-OCF$_3$ | 4-NHCSNH$_2$ | |
| 1.1190 | 5'-CONH$_2$ | 2'-(C$_6$H$_4$-4-Cl) | 2-SCF$_3$ | 4-OCSNH$_2$ | |
| 1.1191 | 5'-CONH$_2$ | 2'-(C$_6$H$_3$-2,4-Cl$_2$) | H | H | |
| 1.1192 | 5'-CONH$_2$ | 2'-(C$_6$H$_3$-2,4-Cl$_2$) | 4-F | H | |
| 1.1193 | 5'-CONH$_2$ | 2'-(C$_6$H$_3$-2,4-Cl$_2$) | 4-Cl | H | |
| 1.1194 | 5'-CONH$_2$ | 2'-(C$_6$H$_3$-2,4-Cl$_2$) | 4-CN | H | |
| 1.1195 | 5'-CONH$_2$ | 2'-(C$_6$H$_3$-2,4-Cl$_2$) | 4-CH$_3$ | H | |
| 1.1196 | 5'-CONH$_2$ | 2'-(C$_6$H$_3$-2,4-Cl$_2$) | 4-CF$_3$ | H | |
| 1.1197 | 5'-CONH$_2$ | 2'-(C$_6$H$_3$-2,4-Cl$_2$) | 4-OCF$_3$ | H | |
| 1.1198 | 5'-CONH$_2$ | 2'-(C$_6$H$_3$-2,4-Cl$_2$) | 4-SCF$_3$ | H | |
| 1.1199 | 5'-CONH$_2$ | 2'-(C$_6$H$_3$-2,4-Cl$_2$) | 4-S(O)CF$_3$ | H | |
| 1.1200 | 5'-CONH$_2$ | 2'-(C$_6$H$_3$-2,4-Cl$_2$) | 4-S(O)$_2$CF$_3$ | H | |
| 1.1201 | 5'-CONH$_2$ | 2'-(C$_6$H$_3$-2,4-Cl$_2$) | 2-F | H | |
| 1.1202 | 5'-CONH$_2$ | 2'-(C$_6$H$_3$-2,4-Cl$_2$) | 2-Cl | H | |
| 1.1203 | 5'-CONH$_2$ | 2'-(C$_6$H$_3$-2,4-Cl$_2$) | 2-CN | H | |
| 1.1204 | 5'-CONH$_2$ | 2'-(C$_6$H$_3$-2,4-Cl$_2$) | 2-CH$_3$ | H | |

TABLE 1-continued

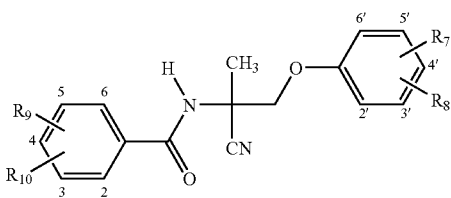

| No. | $R_7$ | $R_8$ | $R_9$ | $R_{10}$ | Phys. data |
|---|---|---|---|---|---|
| 1.1205 | 5'-CONH$_2$ | 2'-(C$_6$H$_3$-2,4-Cl$_2$) | 2-CF$_3$ | H | |
| 1.1206 | 5'-CONH$_2$ | 2'-(C$_6$H$_3$-2,4-Cl$_2$) | 2-OCF$_3$ | H | |
| 1.1207 | 5'-CONH$_2$ | 2'-(C$_6$H$_3$-2,4-Cl$_2$) | 2-SCF$_3$ | H | |
| 1.1208 | 5'-CONH$_2$ | 2'-(C$_6$H$_3$-2,4-Cl$_2$) | 2-S(O)CF$_3$ | H | |
| 1.1209 | 5'-CONH$_2$ | 2'-(C$_6$H$_3$-2,4-Cl$_2$) | 2-S(O)$_2$CF$_3$ | H | |
| 1.1210 | 5'-CONH$_2$ | 2'-(C$_6$H$_3$-2,4-Cl$_2$) | H | 4-NH$_2$ | |
| 1.1211 | 5'-CONH$_2$ | 2'-(C$_6$H$_3$-2,4-Cl$_2$) | H | 4-COOH | |
| 1.1212 | 5'-CONH$_2$ | 2'-(C$_6$H$_3$-2,4-Cl$_2$) | H | 4-CONH$_2$ | |
| 1.1213 | 5'-CONH$_2$ | 2'-(C$_6$H$_3$-2,4-Cl$_2$) | H | 4-CSNH$_2$ | |
| 1.1214 | 5'-CONH$_2$ | 2'-(C$_6$H$_3$-2,4-Cl$_2$) | H | 4-NHCONH$_2$ | |
| 1.1215 | 5'-CONH$_2$ | 2'-(C$_6$H$_3$-2,4-Cl$_2$) | H | 4-NHCSNH$_2$ | |
| 1.1216 | 5'-CONH$_2$ | 2'-(C$_6$H$_3$-2,4-Cl$_2$) | H | 4-OCSNH$_2$ | |
| 1.1217 | 5'-CONH$_2$ | 2'-(C$_6$H$_3$-2,4-Cl$_2$) | H | 3-OC(F$_2$)O-4 | |
| 1.1218 | 5'-CONH$_2$ | 2'-(C$_6$H$_3$-2,4-Cl$_2$) | H | 3-SC(F$_2$)S-4 | |
| 1.1219 | 5'-CONH$_2$ | 2'-(C$_6$H$_3$-2,4-Cl$_2$) | 2-F | 4-NH$_2$ | |
| 1.1220 | 5'-CONH$_2$ | 2'-(C$_6$H$_3$-2,4-Cl$_2$) | 2-Cl | 4-COOH | |
| 1.1221 | 5'-CONH$_2$ | 2'-(C$_6$H$_3$-2,4-Cl$_2$) | 2-CN | 4-CONH$_2$ | |
| 1.1222 | 5'-CONH$_2$ | 2'-(C$_6$H$_3$-2,4-Cl$_2$) | 2-CH$_3$ | 4-CSNH$_2$ | |
| 1.1223 | 5'-CONH$_2$ | 2'-(C$_6$H$_3$-2,4-Cl$_2$) | 2-CF$_3$ | 4-NHCONH$_2$ | |
| 1.1224 | 5'-CONH$_2$ | 2'-(C$_6$H$_3$-2,4-Cl$_2$) | 2-OCF$_3$ | 4-NHCSNH$_2$ | |
| 1.1225 | 5'-CONH$_2$ | 2'-(C$_6$H$_3$-2,4-Cl$_2$) | 2-SCF$_3$ | 4-OCSNH$_2$ | |
| 1.1226 | 5'-CONH$_2$ | 2'-OC$_6$H$_5$ | H | H | |
| 1.1227 | 5'-CONH$_2$ | 2'-OC$_6$H$_5$ | 4-F | H | |
| 1.1228 | 5'-CONH$_2$ | 2'-OC$_6$H$_5$ | 4-Cl | H | |
| 1.1229 | 5'-CONH$_2$ | 2'-OC$_6$H$_5$ | 4-CN | H | |
| 1.1230 | 5'-CONH$_2$ | 2'-OC$_6$H$_5$ | 4-CH$_3$ | H | |
| 1.1231 | 5'-CONH$_2$ | 2'-OC$_6$H$_5$ | 4-CF$_3$ | H | |
| 1.1232 | 5'-CONH$_2$ | 2'-OC$_6$H$_5$ | 4-OCF$_3$ | H | |
| 1.1233 | 5'-CONH$_2$ | 2'-OC$_6$H$_5$ | 4-SCF$_3$ | H | |
| 1.1234 | 5'-CONH$_2$ | 2'-OC$_6$H$_5$ | 4-S(O)CF$_3$ | H | |
| 1.1235 | 5'-CONH$_2$ | 2'-OC$_6$H$_5$ | 4-S(O)$_2$CF$_3$ | H | |
| 1.1236 | 5'-CONH$_2$ | 2'-OC$_6$H$_5$ | 2-F | H | |
| 1.1237 | 5'-CONH$_2$ | 2'-OC$_6$H$_5$ | 2-Cl | H | |
| 1.1238 | 5'-CONH$_2$ | 2'-OC$_6$H$_5$ | 2-CN | H | |
| 1.1239 | 5'-CONH$_2$ | 2'-OC$_6$H$_5$ | 2-CH$_3$ | H | |
| 1.1240 | 5'-CONH$_2$ | 2'-OC$_6$H$_5$ | 2-CF$_3$ | H | |
| 1.1241 | 5'-CONH$_2$ | 2'-OC$_6$H$_5$ | 2-OCF$_3$ | H | |
| 1.1242 | 5'-CONH$_2$ | 2'-OC$_6$H$_5$ | 2-SCF$_3$ | H | |
| 1.1243 | 5'-CONH$_2$ | 2'-OC$_6$H$_5$ | 2-S(O)CF$_3$ | H | |
| 1.1244 | 5'-CONH$_2$ | 2'-OC$_6$H$_5$ | 2-S(O)$_2$CF$_3$ | H | |
| 1.1245 | 5'-CONH$_2$ | 2'-OC$_6$H$_5$ | H | 4-NH$_2$ | |
| 1.1246 | 5'-CONH$_2$ | 2'-OC$_6$H$_5$ | H | 4-COOH | |
| 1.1247 | 5'-CONH$_2$ | 2'-OC$_6$H$_5$ | H | 4-CONH$_2$ | |
| 1.1248 | 5'-CONH$_2$ | 2'-OC$_6$H$_5$ | H | 4-CSNH$_2$ | |
| 1.1249 | 5'-CONH$_2$ | 2'-OC$_6$H$_5$ | H | 4-NHCONH$_2$ | |
| 1.1250 | 5'-CONH$_2$ | 2'-OC$_6$H$_5$ | H | 4-NHCSNH$_2$ | |
| 1.1251 | 5'-CONH$_2$ | 2'-OC$_6$H$_5$ | H | 4-OCSNH$_2$ | |
| 1.1252 | 5'-CONH$_2$ | 2'-OC$_6$H$_5$ | H | 3-OC(F$_2$)O-4 | |
| 1.1253 | 5'-CONH$_2$ | 2'-OC$_6$H$_5$ | H | 3-SC(F$_2$)S-4 | |
| 1.1254 | 5'-CONH$_2$ | 2'-OC$_6$H$_5$ | 2-F | 4-NH$_2$ | |
| 1.1255 | 5'-CONH$_2$ | 2'-OC$_6$H$_5$ | 2-Cl | 4-COOH | |
| 1.1256 | 5'-CONH$_2$ | 2'-OC$_6$H$_5$ | 2-CN | 4-CONH$_2$ | |
| 1.1257 | 5'-CONH$_2$ | 2'-OC$_6$H$_5$ | 2-CH$_3$ | 4-CSNH$_2$ | |
| 1.1258 | 5'-CONH$_2$ | 2'-OC$_6$H$_5$ | 2-CF$_3$ | 4-NHCONH$_2$ | |
| 1.1259 | 5'-CONH$_2$ | 2'-OC$_6$H$_5$ | 2-OCF$_3$ | 4-NHCSNH$_2$ | |
| 1.1260 | 5'-CONH$_2$ | 2'-OC$_6$H$_5$ | 2-SCF$_3$ | 4-OCSNH$_2$ | |
| 1.1261 | 5'-CONH$_2$ | 2'-(OC$_6$H$_4$-4-Cl) | H | H | |
| 1.1262 | 5'-CONH$_2$ | 2'-(OC$_6$H$_4$-4-Cl) | 4-F | H | |
| 1.1263 | 5'-CONH$_2$ | 2'-(OC$_6$H$_4$-4-Cl) | 4-Cl | H | |
| 1.1264 | 5'-CONH$_2$ | 2'-(OC$_6$H$_4$-4-Cl) | 4-CN | H | |
| 1.1265 | 5'-CONH$_2$ | 2'-(OC$_6$H$_4$-4-Cl) | 4-CH$_3$ | H | |
| 1.1266 | 5'-CONH$_2$ | 2'-(OC$_6$H$_4$-4-Cl) | 4-CF$_3$ | H | |
| 1.1267 | 5'-CONH$_2$ | 2'-(OC$_6$H$_4$-4-Cl) | 4-OCF$_3$ | H | |
| 1.1268 | 5'-CONH$_2$ | 2'-(OC$_6$H$_4$-4-Cl) | 4-SCF$_3$ | H | |
| 1.1269 | 5'-CONH$_2$ | 2'-(OC$_6$H$_4$-4-Cl) | 4-S(O)CF$_3$ | H | |
| 1.1270 | 5'-CONH$_2$ | 2'-(OC$_6$H$_4$-4-Cl) | 4-S(O)$_2$CF$_3$ | H | |

TABLE 1-continued

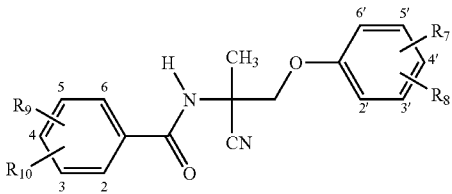

| No. | R$_7$ | R$_8$ | R$_9$ | R$_{10}$ | Phys. data |
|---|---|---|---|---|---|
| 1.1271 | 5'-CONH$_2$ | 2'-(OC$_6$H$_4$-4-Cl) | 2-F | H | |
| 1.1272 | 5'-CONH$_2$ | 2'-(OC$_6$H$_4$-4-Cl) | 2-Cl | H | |
| 1.1273 | 5'-CONH$_2$ | 2'-(OC$_6$H$_4$-4-Cl) | 2-CN | H | |
| 1.1274 | 5'-CONH$_2$ | 2'-(OC$_6$H$_4$-4-Cl) | 2-CH$_3$ | H | |
| 1.1275 | 5'-CONH$_2$ | 2'-(OC$_6$H$_4$-4-Cl) | 2-CF$_3$ | H | |
| 1.1276 | 5'-CONH$_2$ | 2'-(OC$_6$H$_4$-4-Cl) | 2-OCF$_3$ | H | |
| 1.1277 | 5'-CONH$_2$ | 2'-(OC$_6$H$_4$-4-Cl) | 2-SCF$_3$ | H | |
| 1.1278 | 5'-CONH$_2$ | 2'-(OC$_6$H$_4$-4-Cl) | 2-S(O)CF$_3$ | H | |
| 1.1279 | 5'-CONH$_2$ | 2'-(OC$_6$H$_4$-4-Cl) | 2-S(O)$_2$CF$_3$ | H | |
| 1.1280 | 5'-CONH$_2$ | 2'-(OC$_6$H$_4$-4-Cl) | H | 4-NH$_2$ | |
| 1.1281 | 5'-CONH$_2$ | 2'-(OC$_6$H$_4$-4-Cl) | H | 4-COOH | |
| 1.1282 | 5'-CONH$_2$ | 2'-(OC$_6$H$_4$-4-Cl) | H | 4-CONH$_2$ | |
| 1.1283 | 5'-CONH$_2$ | 2'-(OC$_6$H$_4$-4-Cl) | H | 4-CSNH$_2$ | |
| 1.1284 | 5'-CONH$_2$ | 2'-(OC$_6$H$_4$-4-Cl) | H | 4-NHCONH$_2$ | |
| 1.1285 | 5'-CONH$_2$ | 2'-(OC$_6$H$_4$-4-Cl) | H | 4-NHCSNH$_2$ | |
| 1.1286 | 5'-CONH$_2$ | 2'-(OC$_6$H$_4$-4-Cl) | H | 4-OCSNH$_2$ | |
| 1.1287 | 5'-CONH$_2$ | 2'-(OC$_6$H$_4$-4-Cl) | H | 3-OC(F$_2$)O-4 | |
| 1.1288 | 5'-CONH$_2$ | 2'-(OC$_6$H$_4$-4-Cl) | H | 3-SC(F$_2$)S-4 | |
| 1.1289 | 5'-CONH$_2$ | 2'-(OC$_6$H$_4$-4-Cl) | 2-F | 4-NH$_2$ | |
| 1.1290 | 5'-CONH$_2$ | 2'-(OC$_6$H$_4$-4-Cl) | 2-Cl | 4-COOH | |
| 1.1291 | 5'-CONH$_2$ | 2'-(OC$_6$H$_4$-4-Cl) | 2-CN | 4-CONH$_2$ | |
| 1.1292 | 5'-CONH$_2$ | 2'-(OC$_6$H$_4$-4-Cl) | 2-CH$_3$ | 4-CSNH$_2$ | |
| 1.1293 | 5'-CONH$_2$ | 2'-(OC$_6$H$_4$-4-Cl) | 2-CF$_3$ | 4-NHCONH$_2$ | |
| 1.1294 | 5'-CONH$_2$ | 2'-(OC$_6$H$_4$-4-Cl) | 2-OCF$_3$ | 4-NHCSNH$_2$ | |
| 1.1295 | 5'-CONH$_2$ | 2'-(OC$_6$H$_4$-4-Cl) | 2-SCF$_3$ | 4-OCSNH$_2$ | |
| 1.1296 | 5'-CONH$_2$ | 2'-(OC$_6$H$_3$-2,4-Cl$_2$) | H | H | |
| 1.1297 | 5'-CONH$_2$ | 2'-(OC$_6$H$_3$-2,4-Cl$_2$) | 4-F | H | |
| 1.1298 | 5'-CONH$_2$ | 2'-(OC$_6$H$_3$-2,4-Cl$_2$) | 4-Cl | H | |
| 1.1299 | 5'-CONH$_2$ | 2'-(OC$_6$H$_3$-2,4-Cl$_2$) | 4-CN | H | |
| 1.1300 | 5'-CONH$_2$ | 2'-(OC$_6$H$_3$-2,4-Cl$_2$) | 4-CH$_3$ | H | |
| 1.1301 | 5'-CONH$_2$ | 2'-(OC$_6$H$_3$-2,4-Cl$_2$) | 4-CF$_3$ | H | |
| 1.1302 | 5'-CONH$_2$ | 2'-(OC$_6$H$_3$-2,4-Cl$_2$) | 4-OCF$_3$ | H | |
| 1.1303 | 5'-CONH$_2$ | 2'-(OC$_6$H$_3$-2,4-Cl$_2$) | 4-SCF$_3$ | H | |
| 1.1304 | 5'-CONH$_2$ | 2'-(OC$_6$H$_3$-2,4-Cl$_2$) | 4-S(O)CF$_3$ | H | |
| 1.1305 | 5'-CONH$_2$ | 2'-(OC$_6$H$_3$-2,4-Cl$_2$) | 4-S(O)$_2$CF$_3$ | H | |
| 1.1306 | 5'-CONH$_2$ | 2'-(OC$_6$H$_3$-2,4-Cl$_2$) | 2-F | H | |
| 1.1307 | 5'-CONH$_2$ | 2'-(OC$_6$H$_3$-2,4-Cl$_2$) | 2-Cl | H | |
| 1.1308 | 5'-CONH$_2$ | 2'-(OC$_6$H$_3$-2,4-Cl$_2$) | 2-CN | H | |
| 1.1309 | 5'-CONH$_2$ | 2'-(OC$_6$H$_3$-2,4-Cl$_2$) | 2-CH$_3$ | H | |
| 1.1310 | 5'-CONH$_2$ | 2'-(OC$_6$H$_3$-2,4-Cl$_2$) | 2-CF$_3$ | H | |
| 1.1311 | 5'-CONH$_2$ | 2'-(OC$_6$H$_3$-2,4-Cl$_2$) | 2-OCF$_3$ | H | |
| 1.1312 | 5'-CONH$_2$ | 2'-(OC$_6$H$_3$-2,4-Cl$_2$) | 2-SCF$_3$ | H | |
| 1.1313 | 5'-CONH$_2$ | 2'-(OC$_6$H$_3$-2,4-Cl$_2$) | 2-S(O)CF$_3$ | H | |
| 1.1314 | 5'-CONH$_2$ | 2'-(OC$_6$H$_3$-2,4-Cl$_2$) | 2-S(O)$_2$CF$_3$ | H | |
| 1.1315 | 5'-CONH$_2$ | 2'-(OC$_6$H$_3$-2,4-Cl$_2$) | H | 4-NH$_2$ | |
| 1.1316 | 5'-CONH$_2$ | 2'-(OC$_6$H$_3$-2,4-Cl$_2$) | H | 4-COOH | |
| 1.1317 | 5'-CONH$_2$ | 2'-(OC$_6$H$_3$-2,4-Cl$_2$) | H | 4-CONH$_2$ | |
| 1.1318 | 5'-CONH$_2$ | 2'-(OC$_6$H$_3$-2,4-Cl$_2$) | H | 4-CSNH$_2$ | |
| 1.1319 | 5'-CONH$_2$ | 2'-(OC$_6$H$_3$-2,4-Cl$_2$) | H | 4-NHCONH$_2$ | |
| 1.1320 | 5'-CONH$_2$ | 2'-(OC$_6$H$_3$-2,4-Cl$_2$) | H | 4-NHCSNH$_2$ | |
| 1.1321 | 5'-CONH$_2$ | 2'-(OC$_6$H$_3$-2,4-Cl$_2$) | H | 4-OCSNH$_2$ | |
| 1.1322 | 5'-CONH$_2$ | 2'-(OC$_6$H$_3$-2,4-Cl$_2$) | H | 3-OC(F$_2$)O-4 | |
| 1.1323 | 5'-CONH$_2$ | 2'-(OC$_6$H$_3$-2,4-Cl$_2$) | H | 3-SC(F$_2$)S-4 | |
| 1.1324 | 5'-CONH$_2$ | 2'-(OC$_6$H$_3$-2,4-Cl$_2$) | 2-F | 4-NH$_2$ | |
| 1.1325 | 5'-CONH$_2$ | 2'-(OC$_6$H$_3$-2,4-Cl$_2$) | 2-Cl | 4-COOH | |
| 1.1326 | 5'-CONH$_2$ | 2'-(OC$_6$H$_3$-2,4-Cl$_2$) | 2-CN | 4-CONH$_2$ | |
| 1.1327 | 5'-CONH$_2$ | 2'-(OC$_6$H$_3$-2,4-Cl$_2$) | 2-CH$_3$ | 4-CSNH$_2$ | |
| 1.1328 | 5'-CONH$_2$ | 2'-(OC$_6$H$_3$-2,4-Cl$_2$) | 2-CF$_3$ | 4-NHCONH$_2$ | |
| 1.1329 | 5'-CONH$_2$ | 2'-(OC$_6$H$_3$-2,4-Cl$_2$) | 2-OCF$_3$ | 4-NHCSNH$_2$ | |
| 1.1330 | 5'-CONH$_2$ | 2'-(OC$_6$H$_3$-2,4-Cl$_2$) | 2-SCF$_3$ | 4-OCSNH$_2$ | |

BIOLOGICAL EXAMPLES

1. In Vivo Test Against *Trichostrongylus colubriformis* and *Haemonchus contortus* in Mongolian gerbils (*Meriones unquiculatus*) by Peroral Administration Six- to eight-week-old Mongolian gerbils are infected, using manufactured feed, with in each case approximately 2 000 larvae of the 3rd stage of *T. colubriformis* and *H. contortus*. Six days after infecting, the gerbils are lightly anaesthetized with $N_2O$ and are treated by peroral administration with the test compounds, dissolved in a mixture of 2 parts of DMSO and 1 part of polyethylene glycol (PEG 300), with amounts of 100, 32 and 10-0.1 mg/kg. On day 9 (3 days after treating), when most of the *H. contortus* larvae still existing are in the late 4th stage and most of the *T. colubriformis* are immature adults, the gerbils are sacrificed in order to count the worms. The activity is calculated in % reduction in the number of worms in each gerbil by comparison with the geometric mean of the number of worms from 8 infected and untreated gerbils.

In this test, a large decrease in the nematode infestation is obtained with compounds of the formula I, in particular from Table 1. Namely, compounds 1.392 and 1.1058 reduced the number of nematode worms by more than 95%.

The following test methods can be employed in investigating the insecticidal and/or acaricidal action of the compounds of the formula I on animals and plants.

2. Action Against $L_1$ Larvae of *Lucilia sericata*

1 ml of an aqueous suspension of the active substance to be tested is thus mixed at approximately 50° C. with 3 ml of a special medium for raising larvae, so that a homogenate with an active ingredient content of either 250 or 125 ppm is formed. Approximately 30 *Lucilia* larvae ($L_1$) are introduced into each test tube sample. After 4 days, the mortality rate is determined.

3. Acaricidal Action Against *Boophilus microplus* (Biarra Strain)

An adhesive tape is attached horizontally to a PVC plate such that 10 female *Boophilus microplus* ticks (Biarra strain) which have sucked themselves full of blood can be adhesively attached to the tape via their backs in a row, next to one another. Each tick is injected, using an injection needle, with 1 µl of a liquid which is a 1:1 mixture of polyethylene glycol and acetone and in which a certain amount of active ingredient of alternatively 1, 0.1 or 0.01 µg per tick is dissolved. Control animals receive an injection not comprising an active ingredient. After the treatment, the animals are kept in an insectarium under standard conditions at approximately 28° C. and 80% relative humidity until egg laying has occurred and the larvae have hatched from the eggs of the control animals. The activity of a test substance is determined using the $IR_{90}$, i.e. that dose of active ingredient is ascertained at which, after 30 days, 9 out of 10 female ticks (=90%) lay eggs which are not able to hatch.

4. In Vitro Activity Against Fed *Boophilus microplus* Females (Biarra):

4×10 fed female ticks of the OP-resistant Biarra strain are attached to an adhesive tape and are covered for 1 h with a wad of cotton wool which has been impregnated with an emulsion or suspension of the test compound in concentrations in each case of 500, 125, 31 and 8 ppm. The mortality, egg laying and larval hatching are evaluated 28 days later.

An indication of the activity of the test compounds is the number of the females which quickly die, before laying eggs,
survive for some time, without laying eggs,
lay eggs in which no embryos develop,
lay eggs in which embryos develop but from which no larvae hatch, and
lay eggs in which embryos develop and from which larvae hatch normally in 26 to 27 days.

5. In Vitro Activity Against Nymphs of *Amblyomma hebraeum*

About 5 hungry nymphs are placed in a polystyrene test tube comprising 2 ml of the test compound in solution, suspension or emulsion.

After immersing for 10 minutes and shaking for 2×10 seconds on a vortex mixer, the test tubes are plugged with a thick wad of cotton wool and are inverted. As soon as all the liquid has been soaked up by the wad of cotton wool, the wad is pushed halfway into the still inverted test tube, so that most of the liquid is squeezed out of the wad of cotton and flows into a Petri dish placed underneath.

The test tubes are now, until evaluation, stored at ambient temperature in a room lit by daylight. After 14 days, the test tubes are immersed in a beaker of boiling water. If, in reaction to the heat, the ticks begin to move, the test substance is inactive at the test concentration; otherwise, the ticks are considered to be dead and the test substance is considered to be active at the test concentration. All substances are tested in a concentration range from 0.1 to 100 ppm.

6. Action Against *Dermanyssus gallinae*

2 to 3 ml of a solution comprising 10 ppm of active ingredient and approximately 200 mites (*Dermanyssus gallinae*) at various development stages are placed in a glass vessel open at the top. The vessel is subsequently plugged with a wad of cotton wool, shaken for 10 minutes, until the mites have been completely wetted, and then briefly inverted, so that the remaining test solution can be absorbed by the cotton wool. After 3 days, the mortality of the mites is ascertained by counting the dead individuals and is given in percent.

7. Action Against *Musca domestica*

A sugar cube is treated with a solution of the test substance such that the concentration of test substance in the sugar, after drying overnight, is 250 ppm. This treated cube is placed with a wet wad of cotton wool and 10 adult *Musca domestica* of an OP-resistant strain on an aluminium dish, is covered with a beaker and is incubated at 25° C. The mortality rate is determined after 24 hours.

What is claimed is:

1. A compound

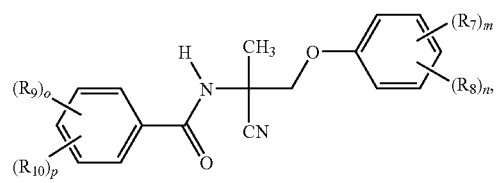

wherein
each of $R_7$ and $R_{10}$ are, independently of each other, carboxy or aminocarbonyl; $R_8$ is halogen, cyano, $C_1$-$C_6$alkyl, halo-$C_1$-$C_6$alkyl, $C_1$-$C_6$alkoxy, halo-$C_1$-$C_6$alkoxy, unsubstituted or one- or poly-substituted phenyl, or unsubstituted or one- or poly-substituted phenoxy, whereby the substituents in each case are independent of each other and are halogen;

$R_9$ is halogen, cyano, $C_1$-$C_6$alkyl, halo-$C_1$-$C_6$alkyl, $C_1$-$C_6$alkoxy, halo-$C_1$-$C_6$alkoxy, $C_3$-$C_6$cycloalkylthio, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, or halo-$C_1$-$C_6$alkylsulfonyl;

each of m, n, o, and p, are, independent of each other, 0 or 1;

with the proviso that m and p are not both 0 at the same time, or a salt thereof.

2. The compound of claim 1, wherein $R_8$ is halo-$C_1$-$C_6$alkyl, or unsubstituted or one- or poly-substituted phenoxy, whereby the substituents are independent of each other and are halogen.

3. The compound of claim 1, wherein $R_9$ is halo-$C_1$-$C_6$alkyl, halo-$C_1$-$C_6$alkoxy, halo-$C_1$-$C_6$alkylthio, halo-$C_1$-$C_6$alkylsulfinyl, or halo-$C_1$-$C_6$alkylsulfonyl.

4. The compound of claim 2, wherein $R_9$ is halo-$C_1$-$C_6$alkyl, halo-$C_1$-$C_6$alkoxy, halo-$C_1$-$C_6$alkylthio, halo-$C_1$-$C_6$alkylsulfinyl, or halo-$C_1$-$C_6$alkylsulfonyl.

5. A compound

4-[2-cyano-2-(4-trifluoromethoxybenzoylamino)-1-propoxy]-3-trifluoromethylbenzamide, or a salt thereof.

6. A composition for controlling parasites comprising a compound of claim 1 as active ingredient and one or more carrier or dispersant.

7. A composition for controlling parasites comprising a compound of claim 5 as active ingredient and one or more carrier or dispersant.

* * * * *

UNITED STATES PATENT AND TRADEMARK OFFICE
CERTIFICATE OF CORRECTION

PATENT NO. : 7,642,379 B2  
APPLICATION NO. : 11/596961  
DATED : January 5, 2010  
INVENTOR(S) : Gauvry et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Fourth Day of January, 2011

David J. Kappos
*Director of the United States Patent and Trademark Office*